US008003619B2

(12) United States Patent
Hartmann et al.

(10) Patent No.: US 8,003,619 B2
(45) Date of Patent: Aug. 23, 2011

(54) METHOD OF STIMULATING AN IMMUNE RESPONSE AND INHIBITING EXPRESSION OF A GENE USING AN OLIGONUCLEOTIDE

(75) Inventors: Gunther Hartmann, Alfter (DE); Antonin de Fougerolles, Brookline, MA (US); Veit Hornung, Pullach (DE); Stefan Endres, Munich (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 83 days.

(21) Appl. No.: 11/298,850

(22) Filed: Dec. 9, 2005

(65) Prior Publication Data

US 2006/0217330 A1   Sep. 28, 2006

Related U.S. Application Data

(60) Provisional application No. 60/634,849, filed on Dec. 9, 2004.

(51) Int. Cl.
*C12N 15/11* (2006.01)
(52) U.S. Cl. .................................................. 514/44 A
(58) Field of Classification Search ................ 514/44 A, 514/44 R
See application file for complete search history.

(56) References Cited

U.S. PATENT DOCUMENTS

| 5,366,878 | A | 11/1994 | Pederson et al. |
|---|---|---|---|
| 5,635,377 | A | 6/1997 | Pederson et al. |
| 5,652,355 | A | 7/1997 | Metelev et al. |
| 6,143,881 | A | 11/2000 | Metelev et al. |
| 6,180,613 | B1 | 1/2001 | Kaplitt et al. |
| 6,235,310 | B1 | 5/2001 | Wang et al. |
| 6,346,614 | B1 | 2/2002 | Metelev et al. |
| 6,586,524 | B2 | 7/2003 | Sagara |
| 2001/0007666 | A1 | 7/2001 | Hoffman et al. |
| 2003/0077829 | A1 | 4/2003 | MacLachlan |
| 2003/0130186 | A1 | 7/2003 | Vargeese et al. |
| 2004/0180848 | A1 | 9/2004 | Fesik et al. |
| 2004/0259097 | A1* | 12/2004 | De Backer et al. ................ 435/6 |
| 2005/0159376 | A1* | 7/2005 | McSwiggen et al. ........... 514/44 |

FOREIGN PATENT DOCUMENTS

| WO | WO 96/10390 | 4/1996 |
|---|---|---|
| WO | WO 96/10391 | 4/1996 |
| WO | WO 96/10392 | 4/1996 |
| WO | WO 00/03683 | 1/2000 |
| WO | WO-01/93902 A2 | 12/2001 |
| WO | WO 2005/087541 | 11/2002 |
| WO | WO-03/070910 A2 | 8/2003 |
| WO | WO-03/070918 A2 | 8/2003 |
| WO | WO-03/074654 A2 | 9/2003 |
| WO | WO-2004/004743 A1 | 1/2004 |
| WO | WO 2004/013280 | 2/2004 |
| WO | WO-2004/036621 A2 | 4/2004 |
| WO | WO-2004/090134 A1 | 10/2004 |

OTHER PUBLICATIONS

Caplen et al. Ann. N.Y. Acad. Sci. 2003, 1002:56-62.*
Kuramoto et al. (Jpn. J. Cancer Res. 1992, vol. 83, pp. 1128-1131).*
Ahlquist et al., "RNA-Dependent RNA polymerases, Viruses, and RNA Silencing," *Science* 296: 1270-1273 (2002).
Alexopoulou et al., "Recognition of Double-Stranded RNA and Activation of NF-κB by Toll-Like Receptor 3," *Nature* 413: 732-738 (2001).
Asselin-Paturel et al., "Mouse Type I IFN-Producing Cells are Immature APC's with Plasmacytoid Morphology," *Nat. Immunol.* 2: 1144-50 (2001).
Baenziger, J. And Fiete, D., "Galactose and N-Acetylgalactosamine-Specific Endocytosis of Glycopeptides by Isolated Rat Hepatocytes," *Cell* 22:611-620 (1980).
Bannai et al., "Effect of Injection of Antisense Oligodeoxynucleotides of GAD Isozymes into Rat Ventromedial Hypothalamus on Food Intake and Locomotor Activity," *Brain Research* 784: 305-315 (1998).
Bannai et al., "Water-Absorbent Polymer as a Carrier for a Discrete Deposit of Antisense Oligodeoxynucleotides in the Central Nervous System," *Brain Research* 3: 83-87 (1998).
Bauer et al., "Human TLR9 Confers Responsiveness to Bacterial DNA via Species-Specific CpG Motif Recognition," *PNAS* 98: 9237-9242 (2001).
Bettinger et al., "Size Reduction of Galactosylated PEI/DNA Complexes Imporives Lectin-Mediated Gene Transfer into Hepatocytes," *Bioconjugate Chem.* 10: 558-561 (1990).
Bitko et al. "Phenotypic Silencing of Cytoplasmic Genes Using Sequence-Specific Double-Stranded Short Interfereing RNA and Its Application in the Reverse Genetics of Wild Type Negative-Strand RNA Viruses" *BMC Microbiology* 1: 1-11 (2001).
Bridge et al. "Induction of an Interferon Response by RNAi Vectors in Mammalian Cells" *Nature Genetics* 34(3): 263-264 (2003).
Broaddus et al., "Distribution and Stability of Antisense Phosphorothioate Oligonucleotides in Rodent Brain Following Direct Intraparenchymal Controlled-Rate Infusion," *J Neurosurg.* 88: 734-742 (1998).
Choi et al. "Effect of Poly(ethylene glycol) Grafting on Polyethylenimine as a Gene Transfer Vector in vitro" *Bull. Korean Chem. Soc.* 22(1): 46-52 (2001).
Connolly et al. "Binding and Endocytosis of Cluster Glycosides by Rabbit Hepatocytes" *The Journal of Biological Chemistry* 257(2): 939-945 (1982).
Davidson, B., "Hepatic Diseases—Hitting the Target with Inhibitory RNAs," The Nw England Journal of Medicine, 349: 2357-2359 (2003). Diebold et al. "Innate Antiviral Responses by Means of TLR7-Mediated Recognition of Single-Stranded RNA" *Science*, 303: 1529-1531 (2004).
Diebold et al. "Mannose Polyethylenimine Conjugates for Targeted DNA Delivery into Dendritic Cells" *The Journal of Biological Chemistry*, 274(27): 19087-19094 (1999).
Dittmer et al., "Treatement of Infectious Diseases with Immunostimulatory Oligodeoxynucleotides Containing CpG Motifs," *Current Opinion in Microbiology* 6: 472-477 (2003).
Edwards et al., "Toll-Like Receptor Expression in Murine DG Subsets: Lack of TLR7 Expresion by CD8α⁺DC Correlates with Unresponsiveness to Imidazoquinolines," *Eur. J. Immunol.* 33: 827-833 (2003).
Elbashir et al. "Duplexes of 21-Nucleotide RNAs Mediate RNA Interference in Cultured Mammalian Cells" *Nature*, 411: 494-498 (2001).
Elbashir et al. "RNA Interference is Mediated by 21- and 22-Nucleotide RNAs" *Genes & Development*, 15: 188-200 (2001).
Elbashir et al. "Functional Anatomy of siRNAs for Mediating Efficient RNAi in *Drosphila melanogaster* Embryo Lysate" *The EMBO Journal* 20(23): 6877-6888 (2001).

(Continued)

*Primary Examiner* — Jon E Angell
(74) *Attorney, Agent, or Firm* — Fenwick & West LLP

(57) ABSTRACT

This invention provides oligonucleotide agents that modulate an immune response by stimulating IFN production and methods of using such agents for therapeutic treatments of mammals.

22 Claims, 9 Drawing Sheets

OTHER PUBLICATIONS

Furgeson et al., "Modified Linear Polyethylenimine-Cholesterol Conjugates for DNA Complexation," *Bioconjugate Chem.* 14: 840-847 (2003).

Godbey et al., "Poly(ethylenimine) and its Role in Gene Delivery," Journal of Controlled Release 60: 149-160 (1999).

Godbey et al. Tracking the Intracellular Path of Poly(ethylenimine)/DNA Complexes for Gene Delivery: *Proc. Natl. Acad. Sci. USA* 96: 5177-5181 (1999).

Haley, B. And Zamore, P., "Kinetic Analysis of the RNAi Enzyme Complex," *Nature Structural & Molecular Biology* 11(7): 599-606 (2004).

Halpern et al., "Bacterial DNA Induces Murine Interferon-γ Production by Stimulation of Interleukin-12 and Tumor Necrosis Factor-α," *Cellular Immunology* 167:72-78 (1996).

Hammond et al. "An RNA-Directed Nuclease Mediates Post-Transcriptional Gene Silencing in *Drosphila* Cells" *Nature* 404: 293-296(2000).

Hannon, G., "RNA Interference," *Nature* 418: 244-251 (2002).

Hartmann et al. "Delineation of a CpG Phosphorothioate Oligodeoxynucleotide for Activating Primate Immune Responses in Vitro and in Vivo" *The Journal of Immunology*, pp. 1617-1624 (2000).

Hartmann et al. "Mechanism and Function of a Newly Identified CpG DNA Motif in Human Primary B Cells" *The Journal of Immunology*, pp. 944-953 (2000).

Heckelsmiller et al., "Combined Dendritic Cell- and CpG Oligonucleotide-Based Immune Therapy Curses Large Murine Tumors that Resist Chemotherapy," *Eur. J. Immunol.* 32: 3235-3245 (2002).

Heckelsmiller et al. "Peritumoral CpG DNA Elicits a Coordinated Response of CD8 T Cells and Innate Effectors to Cure Established Tumors in a Murine Colon Carcinoma Model" *The Journal of Immunology*, pp. 3892-3899 (2002).

Heidel et al. "Lack of Interferon Response in Animals to Nakes siRNAs" *Nature Biotechnology* 22(12): 1579-1582 (2004).

Heil et al. "Species-Specific Recognition of Single-Stranded RNA via Toll-like 7 and 8" *Science*, 303: 1526-1529 (2004).

Heil et al., "The Toll-Like Receptor 4 (TLR7)-Specific Stim,ulus Loxoribine Uncovers a Strong Relationship within the TLR7, 8 and 9 Subfamily," *Eur. J. Immunol.* 33: 2987-2997 (2003).

Hoebe et al. "Upregulation of Costimulatory Molecules Induced by Lipopolysaccharide and Double-Stranded RNA Occurs by Trif-Dependent and Trif-Independent Pathways" *Nature Immunology*, 4(12): 1223-1229(2003).

Hornung et al. "Quantitative Expression of Toll-Like Receptor 1-10 mRNA in Cellular Subsets of Human Peripheral Mononuclear Cells and Sensitivity to CpG Oligodeoxynucleotides" *The Journal of Immunology*, pp. 4532-4537, (2002).

Ishiwata et al. "Physical-Chemistry Characteristics and Biodistribution of Poly(ethylene glycol)-Coated Liposomes Using Ploy(oxyethylene) Cholesteryl Ether" *Chemical and Pharmaceutical Bulletin*, 43(6): 1005-1011 (1995).

Jackson et al., "Expression Profiling Reveals Off-Target Gene Regulation by RNAi," *Nature Biotechnology* 32(6): 635-638 (2003).

Jackson et al., "Noise Amidst the Silence: Off-Target Effects of siRNAs?" Trends in Genetics 20(11): 521-524 (2004).

Kariko et al., "Exogenous siRNA Mediates Sequence-Independent Gene Suppression by Signaling Through Toll-Like Receptor 3," *Cell Tissues Organs* 177: 132-138 (2004).

Kariko et al. "Small Interfering RNAs Mediate Sequence-Independent Gene Suppression and Induce Immune Activation by Signaling through Toll-Like Receptor 3[1]" *The Journal of Immunology* pp. 6545-6549 (2004).

Karle et al., "Differential Changes in Induced Seizures After Hippocampal Treatement of Rats with an Antisense Oligodeoxynucleotide to the $GABA_A$ Receptor γ2 Subunit," *European Journal of Pharmacology* 340: 153-160 (1997).

Katze et al. "Functional Expression and RNA Binding Analysis of the Interferon-Induced, Double-Stranded RNA-Activated, 68,000-$M_r$ Protein Kinase in a Cell-Free System" *Molecular and Cellular Biology* 11(11): 5497-5505 (1991).

Kim et al., "Interferon Induction by siRNAs and ssRNAs Synthesized by Phage Polymerase," Nature Biotechnology 22(3): 321-325 (2004).

Klein et al., "Inhibition of Hepatitis B Virus Replication in Vivo by Nucleosied Analogues and siRNA," *Gastroenterology* 125: 9-18 (2003).

Klinman et al. "CpG Motifs Present in Bacterial DNA Rapidly Induce Lymphocytes to Secrete Interleukin 6, Interleukin 12, and Interferon γ" *Proc. Natl. Acad. Sci. USA* 93: 2879-2883 (1996).

Kreig et al., "CpG Motifs in Bacterial DNA Trigger Direct B-Cell Activation," *Nature* 374: 546-549 (1995).

Krug et al. "Herpes Simplex Virus Type 1 Activates Murine Natural Interferon-Producing Cells Through Toll-Like Receptor 9" *Blood* 103(4): 1433-1437 (2004).

Krug et al. "CpG-A Oligonucleotides Induce a Monocyte-Derived Dendritic Cell-Like Phenotype That Preferentially Activates CD8 T Cells" *The Journal of Immunology*, pp. 3465-3477 (2003).

Krug et al., "Identification of CpG Oligonucleotide Sequences with High Induction of IFN-α/β in Plasmacytoid Dendritic Cells," *Eur. J. Immunol.* 31: 2154-2163 (2001).

Krug et al., "Toll-Like Receptor Expression Reveals CpG DNA as a Unique Microbial Stimulus for Plasmacytoid Dendritic Cells Which Synergizes with CD40 Ligand to Induce High Amounts of IL-12," *Eur. J. Immunol.* 31: 3026-3037 (2001).

Kunath et al., "The Structure of PEG-Modified Poly(Ethylene Imines) Influences Biodistribution and Pharmacokinetics of Their Complexes with NF-κB Decoy in Mice," *Pharmaceutical Research* 19(6): 810-817 (2002).

Lasic et al. "Liposomes Revisited" *Science*, 267(2502): 1257-1276 (1995).

Lasic et al., "The 'Stealth' Liposome: A Prototypical Biomaterial" *Chemical Reviews* 95(8): 2601-2628 (1995).

Latz et al. "TLR9 Signals After Translocating from thr ER to CpG DNA in the Lysosome" *Nature Immunology* 5(2):190-198 (2004).

Lee et al. "Molecular Basis for the Immunostimulatory Activity of Guanine Nucleoside Analogs: Activation of Toll-Like Receptor 7" *PNAS* 100(11): 6646-6651 (2003).

Lee et aL "Preparation of Cluster Glycosides of N-Acetylgalactosamine That Have Subnanomolar Binding Constants Towards the Mammalian Hepatic Gal/GalNAc-Specific Receptor" *Gycoconjugate J* 4: 314-328 (1987).

Liang et al. "Activation of Human B Cells by Phosphorothioate Oligodeoxynucleotides" *J. Clin. Invest.* 98(5): 1119-1129 (1996).

Limbach et al. "Summary: The Modified Nucleosides of RNA" *Nucleic Acids Research* 22(12): 2183-2196 (1994).

Liu et al. "Cationic Liposome-Mediated Intravenous Gene Delivery" *The Journal of Biological Chemistry* 270(42): 24864-24870 (1995).

Lund et al. "Toll-Like Receptor 9-Mediated Recognition of Herpes Simplex Virus-2 by Plasmacytoid Dendritic Cells" *J. Exp. Med.* 198(3): 513-520 (2003).

Lund et al. "Recognition of Single Stranded RNA Viruses by Toll-Like Receptor 7" *PNAS* 101(15): 5598-5603 (2004).

Manche et al. "Interactions Between Double-Stranded RNA Regulators and the Protein Kinase DAI" *Molecular and Cellular Biology*, 12(11): 5328-5248 (1992).

Matsumoto et al. "Subcellular Localization of Toll-Like Receptor 3 in Human Dendritic Cells" *The Journal of Immunology*, pp. 3154-3162 (2003).

Messina et al., "Stimulation of In Vitro Murine Lymphocyte Proliferation by Bacterial DNA," *The Journal of Immunology*, 147: 1759-1764 (1991).

Meurs et al. "Constitutive Expression of Human Double-Stranded RNA-Activated p68 Kinase in Murine Cells Mediates Phosphorylation of Eukaryotic Initiation Factor 2 and Partial Resistance to Encephalomyocarditis Virus Growth" *Jounal of Virology* 66(10): 5805-5814 (1992).

Moss, E. and Taylor, J., "Small-Interfering RNA's in the Radar of the Interferon System," *Nature Cell Biology* 5(9): 771-772 (2003).

Ogris et al "DNA/polyethylenimine Transfection Particles: Influence of Ligands, Polymer Size, and PEGlation on Internalization and Gene Expression" *AAPS PharmSci*, 3(3): 1-11 (2001); [http://www.pharmsci.org].

Oku et al. "Real-Time Analysis of Liposomeal Trafficking in Tumor-Bearing Mice by Use of Positron Emission Tomography" *Biochimica et Biophysica Acta* 1238: 86-90 (1995).
Pebemard, S. and Iggo, R., "Determinant of Interferon-Stimulated Gene Induction by RNAi Vectors," *Differentiation* 71: 103-111 (2004).
Petersen et al., "Polyethylenimine-*Graft*-Poly(wthylene glycol) Copolymers: influence of Coploymer Block Structure on DNA Complexation and Biological Activities as Gene Delivery System," *Bioconjugate Chem.* 13:845-854 (2002).
Plasterek et al., "RNA Silencing: The Genome's Immune System," *Science* 296: 1263-1265 (2002).
Ponpipom et al., "Cell-Specific Ligands for Selective Drug Delivery to Tissue and Organs," *J. Med. Chem.* 24: 1388-1395 (1981).
Rajakumar et al., "Effects of Intrastriatal Infusion of D2 Receptor Antisense Oligonucleotide on Apomorphone-Induced Behaviors in the Rat," *Synapse* 26:199-208 (1997).
Rammensee et al., "MHC Ligands and Peptide Motifs: First Listing," *Immunogenetics* 41:178-228 (1995).
Rothenfusser er al., "CpG-A and CpG-B Oligonucleotides Differentially Enhance Human Peptide-Specific Primary and Memory CD8+ T-Cell Responses in vitro" *Blood* 103(6): 2162-2169 (2004).
Rothenfusser et al., "Distinct CpG Oligonucleotide Sequences Activate Human γδ T Cells Via Interferon $-\alpha/\beta$," *Eur. J. Immunol.* 31: 3235-3534 (2001).
Sato et al., "Immunostimulatory DNA Sequences Necessary for Effective Intradermal Gene Immunization," *Science* 273: 352-354 (1996).
Simantov et al., "Dpoamine-Induced Apoptosis in Human Neuronal Cells: Inhibition by Cucleic Acids Antisense to the Dopamine Transported," *Neuroscience* 74(1): 39-50 (1996).
Sledz et al. "Activation of the Interferon System by Short-Interfering RNAs" *Nature Cell Biology* 5(9): 834-839 (2003).
Sommer et al., "The Spread and Uptake Pattern of Intracerebrally Administered Oligonucleotides in Nerve and Clial Cell Populations of the Rat Brain," *Antisense & Nucleic Acid Drug Development* 8: 75-85 (1998).
Takeda et al., "Toll-Like Receptors," *Annu. Rev. Immunol.* 21: 335-376 (2003).
Thomas et al. "Enhancing Polyethylenimine's Delivery of Plasmid DNA into Mammalian Cells" *PNAS* 99(23): 14640-14645 (2002).
Tokunaga et al., "Antitumor Activity of Deoxyribonucleic Acid Fraction From *Mycobacterium bovis* BCG. I. Isolation, Physochemical Charecterization, and Antitumor Activity," *JNCI* 72(4): 955-962 (1984).
Tokunaga et al., "Synthetic Oligonucleotides with Particular Base Sequences from the cDNA Encoding Proteins of *Mycobacterium bovis* BCG Induce Interferons and Activate Natural Killer Cells," *Microbiol. Immunol.* 36: 55-66 (1992).
Tuschl, T., "RNA Interference and Small Interfering RNAs," *Chembiochem.* 2: 239-245 (2001).
Tuschl, T. and Brokhardt, A., "Small Interfering RNAs: A Revolutionary Tool for the Analysis of Gene Function and Gene Therapy" *Molecular Interventions* 2(3): 158-167 (2002).

Wagner et al., "Immunostimulatory DNA Sequences Help to Eradictae Intracellular Pathogens," *Springer Semin. Immunopathol.* 22: 147-152 (2000).
Wagner, H., "Interactions Between Bacterial CpG-DNA and TLR9 Bridge Innate and Adaptive Immunity," *Current Opinions in Microbiology*, 5: 62-69 (2002).
Weiner, WJ., "CpG DNA in Cancer Immunotherapy," *Curr Top Microbiol Immunol* 247, 157-170 (2000).
Williams, Bryan RG., "PKR; A Sentinel Kinase for Cellular Stress" *Oncogene* 18: 6112-6120 (1999).
Williams, Bryan RG., "Signal Integration via PKR," *Science STKE* 89:1-11 (2001).
Wu et al. "Receptor-Mediated in Vitro Gene Transformation by a Soluble DNA Carrier System" *The Journal of Biological Chemistry* 262(10): 44229-4432 (1987).
Wu-Pong, S., "Nucleic Acid Drug Delivery, Part 2: Delivery to the Brain," *BioPharm*, 12(1), 32-38 (1999).
Yamamoto et al. "In vitro Augmentation of Natural Killer Cell Activity and Production of Interferon-α/β and -γ with Deoxyribonucleic Acid Fraction from *Mycobacterium bovis* BCG" *Jpn. J. Cancer Res.* 79: 866-873 (1988).
Yamamoto et al., "Unique Palindromic Sequences in Synthetic Oligonucleotides are Required to Induce INF and Augment INF-Mediated Natural Killer Activity," *The Journal of Imunology* 148: 4072-4076 (1992).
Zamore et al., "Ancient Pathways Programmed by Small RNAs," *Science* 296: 1265-1269 (2002).
Zamore et al. "RNAi: Double-Stranded RNA Directs the ATP-Dependent Cleavage of mRNA at 21 to 23 Nucleotide Intervals" *Cell* 101:25-33 (2000).
Zhao et al., "Pattern and Kinetics of Cytokine Production Following Administration of Phosphorothioate Oligonucleotides in Mice," *Anitsense & Nucleic Acid Drug Development* 7: 495-502 (1997).
Zheng et al. "Activation of the Protein Kinase PKR by Short Double-Stranded RNAs with Single-Stranded Tails" *RNA* 10:1934-1945 (2004).
U.S. Appl. No. 60/362,016, filed Mar. 6, 2002 105 pages.
PCT International Search Report and Written Opinion, PCT Jul. 14, 2008, PCT/US2005/044662, 11 Pages.
Examiner's First Report on Australia Patent Application No. 2005313883, Feb. 22, 2010, 2 Pages.
European Search Report for European Patent Application No. EP 05853546.9, Jul. 26, 2010, 13 Pages.
Hannoush, R. N., et al., "Diversity-oriented solid-phase synthesis and biological evaluation of oligonucleotide hairpins as HIV-1 RT RNase H inhibitors," Nucleic Acids Research, 2004, p. 6164-6175, vol. 32, No. 21.
Hornung, V., et al., "Sequence-specific potent induction of IFN-α by short interfering RNA in plasmacytoid dendritic cells through TLR7," Nature Medicine, Mar. 2005, pp. 263-270, vol. 11, No. 3.
Ru, K., et al., "Growth inhibition and antimetastatic effect of antisense poly-DNP-RNA on human breast cancer cells," Oncol Res. 1999, pp. 505-512, vol. 11, Nos. 11-12.

* cited by examiner

METHOD OF STIMULATING AN IMMUNE RESPONSE AND INHIBITING EXPRESSION OF A GENE USING AN OLIGONUCLEOTIDE

RELATED APPLICATIONS

This application claims the benefit of U.S. Provisional Application No. 60/634,849, filed Dec. 9, 2004, which is incorporated herein by reference in its entirety.

TECHNICAL FIELD

This invention relates to the field of immunotherapy and drug discovery by providing sequence specific oligoribonucleotide agents that are capable of inducing an immune response in a subject as well as a method for avoiding sequence specific immune responses to RNAi agents.

BACKGROUND

Double-stranded RNA molecules (dsRNA) can block gene expression by virtue of a highly conserved regulatory mechanism known as RNA interference (RNAi). Briefly, the RNA III Dicer enzyme processes dsRNA into small interfering RNA (also sometimes called short interfering RNA or siRNA) of approximately 22 nucleotides. One strand of the siRNA (the "antisense strand") then serves as a guide sequence to induce cleavage of messenger RNAs (mRNAs) including a nucleotide sequence which is at least partially complementary to the sequence of the antisense strand by an RNA-induced silencing complex RISC. The antisense strand is not cleaved or otherwise degraded in this process, and the RISC including the antisense strand can subsequently affect the cleavage of further mRNAs.

The process of posttranscriptional dsRNA-dependent gene silencing is commonly referred to as RNA interference (RNAi) (Tuschl, T. *Chembiochem* 2, 239-45 (2001), Zamore, P. D. *Science* 296, 1265-9 (2002), Hannon, G. J. *Nature* 418, 244-51 (2002)). It has been proposed that eukaryotes utilize RNAi to protect their genomes against invading foreign genetic elements such as viruses. The formation of dsRNA during viral replication is interpreted by the cell as a signal for unwanted gene activity (Ahlquist, P. *Science* 296, 1270-3 (2002), Plasterk, R. H. *Science* 296, 1263-5 (2002)). Dicer RNase III rapidly processes dsRNA to small dsRNA fragments of distinct size and structure, the small interfering RNAs (siRNAs), which direct the sequence-specific degradation of the single-stranded mRNAs of the invading genes (Elbashir, S. M. et al. *Nature* 411, 494-8 (2001), Elbashir, S. M., et al. *Genes Dev* 15, 188-200 (2001), Hammond, S. M., et al. *Nature* 404, 293-6 (2000), Zamore, P. D., et al. *Cell* 101, 25-33 (2000)). Such siRNA duplexes have 2-3 nt 3' overhanging ends and contain 5' phosphate and free 3' hydroxyl termini (Elbashir, S. M., et al. *Embo J* 20, 6877-88 (2001)). Cellular delivery of synthetic siRNA duplexes or introduction of siRNA by plasmids or viral vectors is now widely used to disrupt the activity of cellular genes homologous in sequence to the introduced dsRNA.

An understanding of how siRNAs interact with mammalian systems is important for refining this gene silencing technology and for developing gene-specific therapeutic agents (Tuschl, T. et al. *Mol Interv* 2, 158-67 (2002)). For the recognition of long dsRNA two different detection modes are known, the serine threonine kinase PKR (Williams, B. R. *Sci Signal Transduction Knowledge Enviroment* 89, RE2 (2001), Meurs, E. F. et al. *Virol* 66, 5805-14 (1992), Katze, M. G. et al. *Mol Cell Biol* 11, 5497-505 (1991)) and TLR3 (Alexopoulou, L., et al. *Nature* 413, 732-8 (2001)). While PKR is located in the cytosol, TLR3 is present in the endosomal compartment (Matsumoto, M. et al. *J Immunol* 171, 3154-62 (2003)). TLR3 is a member of the Toll-like receptor family that has evolved to detect pathogen-specific molecules (Takeda, K., et al. *Annu Rev Immunol* 21, 335-76 (2003)).

PKR possesses two dsRNA-binding domains, one of which has high affinity for dsRNA, while the other shows considerably lower affinity. Full activation of the PKR-mediated response requires simultaneous binding of dsRNA to both domains, which may be facilitated by long dsRNAs, e.g. dsRNAs exceeding 50-80 nucleotide pairs in length, and seems to require dimerization (Manche, L., et al., *Mol Cell Biol*, 12, 5238-48 (1992); Williams, B. G., *Oncogene*, 18, 6112-20 (1999)). High concentrations of dsRNAs, including dsRNAs of less than 50 nucleotide pairs, or of other ligands for the dsRNA binding site (e.g. Alu RNAs) inhibit the activation of PKR. Early investigations seemed to prove that siRNA duplexes are short enough to bypass general dsRNA-induced unspecific effects in vertebrate cells (Bitko, V. et al. *BMC Microbiol*, 1, 34 (2001)). A number of more recent publications, however, indicates that a large array of genes is differentially regulated upon the introduction of short dsRNAs, including genes involved in the interferon pathway and specifically the activation of PKR, even if not to a similar extent as compared to the effect of long dsRNAs (Jackson, A. L. and Linsley, P. S., *Trends Genet*, 20, 521-4 (2004); Jackson, A. L., et al., *Nat Biotechnol*, 21, 635-7 (2003); Moss, E. G., and Taylor, J. M., *Nat Cell Biol*, 5, 771-2 (2003); Bridge, A. J., et al., *Nat Genet*, 34, 263-4 (2003); Sledz, C. A., et al., *Nat Cell Biol*, 5, 834-9 (2003); Heidel, J. D., et al., *Nat Biotechnol*, 22, 1579-81 (2004); Kim, D. H., et al., *Nat Biotechnol*, 22, 321-5 (2004); Zheng, X., and Bevilacqua, P. C., *RNA*, 10, 1934-45 (2004); Pebernard, S., and Iggo, R., *Differentiation*, 72, 103-11 (2004)). Which genes are up- or downregulated seems to be at least partly siRNA-sequence specific, and the mechanism, or mechanisms, underlying this regulation remain(s) to be elucidated.

A second characteristic feature of viral nucleic acids used by the immune system to recognize viral infection are CpG motifs found in viral DNA, which are detected via TLR9 (Lund, J., et al. *J Exp Med* 198, 513-520 (2003), Krug, A. et al. *Blood* 103, 1433-7 (2004)). CpG motifs are unmethylated CG dinucleotides with certain flanking bases. The frequency of CpG motifs is suppressed in vertebrates, allowing the vertebrate immune system to detect microbial DNA based on such CpG motifs (Krieg, A. M. et al. *Nature* 374, 546-9 (1995), Bauer, S. et al. *Proc Natl Acad Sci USA* 98, 9237-42 (2001), Wagner, H. *Curr Opin Microbiol* 5, 62-9 (2002)). Like TLR3, TLR9 is located in the endosomal compartment where it directly binds to CpG motifs (Latz, E. et al. *Nat Immunol* 5, 190-8 (2004)).

In addition to long dsRNA and CpG DNA, two recent publications suggest a third mechanism by which viral nucleic acids are recognized. These studies demonstrate that single-stranded RNA (ssRNA) of ssRNA viruses is detected via TLR7 (mouse and human) and TLR8 (only human) (Diebold, S. S., *Science* 303, 1529-31 (2004), Heil, F. et al. *Science* 303, 1526-9 (2004)). Guanine analogues have been identified earlier as specific ligands for TLR7 and TLR8 (Lee, J. et al. *Proc Natl Acad Sci USA* 100, 6646-51 (2003), Heil, F. et al. *Eur J Immunol* 33, 2987-97 (2003)). Like TLR9 (receptor for CpG DNA)(Latz, E. et al. *Nat Immunol* 5, 190-8 (2004)), TLR7 and TLR8 are located in the endosomal membrane.

Detection of viral nucleic acids leads to the production of type I IFN (IFN-α and IFN-β). The major producer of type I IFN in humans is the plasmacytoid dendritic cell (also called interferon producing cell, IPC). The plasmacytoid dendritic cell (PDC) is a highly specialized subset of dendritic cells that is thought to function as a sentinel for viral infection and that is responsible for the vast amount of type I IFN during viral infection (Asselin-Paturel, C. et al. *Nat Immunol* 2, 1144-50 (2001)). There is increasing evidence that PDC preferentially use nucleic acid-based molecular patterns to detect viral infection. TLR expression of human and mouse PDC is limited to TLR7 and TLR9 (Krug, A. et al. *Eur J Immunol* 31, 3026-37 (2001), Hornung, V. et al. *J Immunol* 168, 4531-7 (2002), Edwards, A. D. et al. *Eur J Immunol* 33, 827-33 (2003)).

Tokunaga et al, J. Natl. Cancer Inst. 72:955-962 (1984); Messina et al., J. Immunol. 147: 1759-1764 (1991); Krieg et al., Nature 374: 546-549 (1995); Sato et al, Science 273: 352-354 (1996), teach that the presence of CpG dinucleotides in certain sequence contexts in bacterial and synthetic oligodeoxyribonucleotides (CpG DNAs) are known to activate vertebrate innate immune reaction, T-cells and B cells.

Yamamoto et al., Jpn. J. Cancer Res. 79: 866-873 (1988); Halpern et al., Cell Immunol., 167: 72-78 (1996); Klinman et al., Proc. Natl. Acad. Sci. U.S.A. 93: 2879-2883 (1996); Zhao et al., Antisense Nucleic Acid Drug Dev. 7: 495-502 (1997) teach that the activation of immune cells by CpG DNA induces secretion of a number of cytokines, including IFN-.gamma., IL-12, TNF-.alpha., and IL-6, and stimulates expression of costimulatory surface molecules.

Krieg et al., supra; Yamamoto et al, J. Immunol. 148; 4072-4076 (1992); Tokunaga et al., Microbiol. Immunol. 36: 55-66 (1992); Liang et al., J. Clin. Invest. 98: 1119-1129 (1996); Hartmann et al., J. Immunol. 164: 1617-1624 (2000), teach that the presence of a CpG dinucleotide and the sequences flanking the dinucleotide play a critical role in determining the immunostimulatory activity of DNA, that CpG dinucleotides in palindromic or non-palindromic hexameric sequences ($P_1 . P_2CGP_3P_4$) are required for immune stimulation, and further, that PuPuCGPyPy and PuTCG motifs optimally activate murine and human immune systems, respectively.

While these findings demonstrate that oligonucleotides are useful as immune stimulating agents, some problems with such use still exist. For example, long oligonucleotides are expensive to make and species specificity of flanking sequences limits the breadth of utility of any given oligonucleotide. There is, therefore, a need for less expensive immunostimulatory agents, and preferably immunostimulatory agents that have cross-species efficacy as well as a need to identify additional sequence specific motifs.

SUMMARY

The invention is based, at least in part, on the discovery that a particular sequence motif in a single or double stranded RNA molecule is effective at stimulating an immune response via IFN induction, particularly in cells expressing TLR7, such as plasmacytoid dendritic cells (PDC). Based on this discovery, the present invention provides immunostimulatory oligonucleotide agents that can be used to stimulate IFN production in a mammal as well as methods of selectively designing single stranded antisense agents and double stranded iRNA agents so as to induce a wanted immune response or to avoid inducing an unwanted immune response.

The invention provides therapeutic compositions comprising a single stranded or double stranded oligonucleotide as immunostimulatory agents as well as a method of using such composition for immunotherapy applications. The invention specifically provides methods and compositions for enhancing the immune response used for immunotherapy applications such as, but not limited to, treatment of cancer, autoimmune disorders, asthma, respiratory allergies, food allergies, and bacteria, parasitic, and viral infections in adult and pediatric human and veterinary applications. The invention further provides methods for making such compounds. In addition, compounds of the invention are useful as adjuvants in combination with DNA vaccines, antibodies, and allergens; and in combination with other immunostimulatory agents, chemotherapeutic agents, iRNA agents and/or antisense oligonucleotides.

The oligonucleotide agents of the present invention will comprise, consist of or consist essentially of the nucleotide sequence

5'-GUCCUUCAA-3'. (SEQ ID NO: 1)

In other embodiments, the oligonucleotide will consist of, consist essentially of or comprise 4 or more, 5 or more, 6 or more, 7 or more or 8 or more contiguous nucleotides from SEQ ID NO:1, preferably taken from the 5' end of this sequence, e.g. 5'-GUCC-3' (SEQ ID NO:2), 5'-GUCCU-3' (SEQ ID NO:3), 5'-GUCCUU-3' (SEQ ID NO:4), 5'-GUCCUUC-3' (SEQ ID NO:5), or 5'-GUCCUUCA-3' (SEQ ID NO:6).

Specifically, in one aspect, the invention provides a method of stimulating an immune response in a mammal comprising the step of administering to said mammal an oligonucleotide agent consisting of, consisting essentially of, or comprising a sequence of 4 or more, 5 or more, 6 or more, 7 or more or 8 or more contiguous nucleotides from SEQ ID NO:1, preferably taken from the 5' end of this sequence. Said oligonucleotide agent may consist of, consist essentially of, or comprise SEQ ID NO:1, or a sequence that differs by not more than 1 or not more than 2 nucleotides from SEQ ID NO:1. Said sequence may be chosen from the group of: SEQ ID NO:2, SEQ ID NO:3, SEQ ID NO:4, SEQ ID NO:5, and SEQ ID NO:6. The oligonucleotide may be an iRNA agent, or it may be a single stranded RNA agent.

In a second aspect, the invention provides a method of making an oligonucleotide agent so as to avoid stimulating an immune response in a mammal, comprising the step of eliminating from a potential agent pool any agent that comprises a sequence of 4 or more, or more, 6 or more, 7 or more or 8 or more contiguous nucleotides from SEQ ID NO:1, preferably taken from the 5' end of this sequence, or a sequence that differs from SEQ ID NO:1 by not more than one or not more than 2 nucleotides. The oligonucleotide may be an iRNA agent, or it may be a single stranded RNA agent.

In a third aspect, the instant invention provides an isolated oligonucleotide agent consisting of, consisting essentially of, or comprising a sequence of 4 or more, 5 or more, 6 or more, 7 or more or 8 or more contiguous nucleotides from SEQ ID NO:1, preferably taken from the 5' end of this sequence. The oligonucleotide agent may consist of, consist essentially of, or comprise SEQ ID NO:1, or a sequence that differs by not more than 1 or not more than 2 nucleotides from SEQ ID NO:1. Said sequence may be chosen from the group of: SEQ ID NO:2, SEQ ID NO:3, SEQ ID NO:4, SEQ ID NO:5, and SEQ ID NO:6. The oligonucleotide may be an iRNA agent, or it may be a single stranded RNA agent. It may further comprise at least one 2'-fluoro-modified nucleotide, wherein the 2'-fluoro-modified nucleotide is not part of a sequence of 4 or more contiguous nucleotides from SEQ ID NO:1. Where the oligonucleotide agent is an iRNA agent, it may be specific for (e.g. one strand is at least partially complementary to) any one of the genes of Table 8.

In a fourth aspect, the present invention provides a method of making an oligonucleotide agent so as to induce an immune response in a mammal, comprising the step of adding to a potential agent pool any agent that comprises 4 or more, 5 or more, 6 or more, 7 or more, or 8 or more contiguous nucleotides of SEQ ID NO:1, or a sequence that differs from SEQ ID NO:1 by not more than one or not more than 2 nucleotides. The oligonucleotide may be an iRNA agent, or it may be a single stranded RNA agent.

In a fifth aspect, the invention provides a method of concomitantly inhibiting the expression of a gene and inducing an immune response in a mammal, comprising administering to said mammal an iRNA agent comprising a sequence of 4 or more, 5 or more, 6 or more, 7 or more, or 8 or more contiguous nucleotides of SEQ ID NO:1, preferably taken from the 5' end of this sequence, or a sequence that differs from SEQ ID NO:1 by not more than one or not more than 2 nucleotides. Said sequence may be chosen from the group of: SEQ ID NO:2, SEQ ID NO:3, SEQ ID NO:4, SEQ ID NO:5, and SEQ ID NO:6. Said gene may be any one of the genes of Table 8.

In a sixth aspect, the present invention provides a method of evaluating an iRNA agent comprising:
providing a candidate iRNA agent;
reviewing the candidate iRNA agent to determine if it includes SEQ ID NO:1 or a sequence that differs from SEQ ID NO:1 by 1 or 2 nucleotides.

Said method may further comprise modifying the iRNA agent to remove the sequence of SEQ ID NO:1 or the sequence that differs from SEQ ID NO:1 by 1 or 2 nucleotides.

In a seventh aspect, the present invention provides a pharmaceutical composition comprising an oligonucleotide of the invention and a pharmaceutically acceptable carrier. Said pharmaceutical composition may be a vaccine.

In an eighth aspect, the present invention provides a method of making an oligonucleotide agent so as to avoid stimulating an immune response in a mammal, wherein said oligonucleotides comprises a sequence of 4 or more, 5 or more, 6 or more, 7 or more or 8 or more contiguous nucleotides from SEQ ID NO:1, comprising providing the oligonucleotide agent in such manner that it contains at least 2, or at least 4,2'-O-methyl modified nucleotides. At least one, or at least two, of the 2'-O-methyl-modified nucleotides may be part of a sequence of 4 or more contiguous nucleotides from SEQ ID NO:1

BRIEF DESCRIPTION OF DRAWINGS

FIG. 1A: HEK 293 cells expressing a construct of human TLR9 with a C-terminal YFP-tag were transfected with four siRNAs complementary to different regions of human TLR9 mRNA. Transfection with siRNA targeting GFP mRNA and TLR2 (referred to as sirna2.1 in the figures) mRNA served as a positive or negative control. At 20 hours the median fluorescence intensity of YFP-tag expression was analyzed by flow cytometry. Results are shown as mean values±SEM (n=3). FIG. 1B: HEK 293 cells were incubated alone (lane 1), with lipofectamine (lane 2), with a 500 bp long dsRNA (10 µg/ml, lane 3), or were transfected with lipofectamine complexed with a 500 bp long dsRNA (lane 4), complexed with four different siRNAs targeting the human TLR9 mRNA (TLR9.1, TLR9.2, TLR9.3 and TLR9.4; lane 5 to 8; TLR9.1, TLR9.2, TLR9.3 and TLR9.4 are referred to as sirna9.1, sirna9.2, sirna9.3, and sirna9.4, respectively, in the figures). After 24 hours supernatants were harvested and added to BL41 cells ($1\times10^6$ cells/condition). Addition of recombinant IFN-β (100 U/ml) served as a positive control (lane 9). After 30 min, BL41 cells were lysed and subjected to SDS-page to examine STAT1- and STAT2-phosphorylation. Supernatants were collected from quadruplicates. One representative experiment out of three is shown.

FIG. 2A: PDC were transfected with 200 ng of four different siRNAs (TLR9.1, TLR9.2, TLR9.3 and TLR9.4). The TLR9-ligand CpG-A (ODN 2216, grey bar) served as a positive control for IFN-α induction. Results represent the mean IFN-α production±SEM from eleven individual donors ($p<0.0001$ for TLR9.1 vs. TLR9.2, $p<0.0001$ for TLR9.1 vs. TLR9.3, $p<0.0001$ for TLR9.3 vs. TLR9.1 and $p<0.001$ for TLR9.3 vs. TLR9.4). FIG. 2B: PDC were transfected with decreasing amounts (200 ng, 100 ng, 50 ng, 25 ng) of TLR9.1, TLR9.2, TLR9.3 or TLR9.4. Results represent the mean IFN-α production±SEM from three individual donors. FIG. 2C: PDC were transfected with either siRNA9.2 duplex or the corresponding sense and anti-sense strands. Results from ten individual donors were summarized and are depicted as mean values±SEM. FIG. 2D (left panel): The FITC-modified version of the siRNA9.2 sense strand or the corresponding annealed siRNA-duplex were incubated with or without RNAse at 266 µg/ml. After three hours 4 µl of this preparation were analyzed on a 3% agarose-gel, whereas untreated samples were included as controls. FIG. 2D (right panel): Subsequently samples were purified via siRNA-purification-columns to remove RNase and 3 µl of this preparation was transfected into PDCs. After 36 h IFN-α -production was assessed by ELISA. Data from one of two representative experiments are depicted. FIG. 2E: The self-stabilizing single-stranded hairpin-version of siRNA-duplex 9.2 (see table 2) is compared to the siRNA9.2 duplex. Data from two independent experiments are presented as means±SEM.

FIG. 3A: PDC were transfected with the sense strand of TLR9.2 (RNA9.2s, the original sequence designated "n") and with fluorescein-tagged (5'F or 3'F) versions of RNA9.2s. * indicate $p<0.05$. FIG. 3B: PDC were transfected with the sense strand of TLR9.2, a 19-mer polyA-oligonucleotide, a panel of RNA9.2s derivatives in which base number 8 to 12 counting from the 5'end were replaced by adenosine (L8A to L12A), a panel of RNA9.2s derivatives in which one, two, three or six bases within the 9 bases counting from the 3'end (putative motif) were replaced by adenosine or uridine (in order to disrupt the putative 9mer motif), or two shortened versions of RNA9.2s (a 16mer and a 12mer both containing the putative 9mer motif of the 3'end of RNA9.2s) and a 19mer RNA oligonucleotide containing the putative 9mer motif two times within its sequence (DR). A detailed list of all sequences used is provided in Table 2. Results from four individual donors are depicted as mean values±SEM.

FIG. 4A: The sense strand of TLR9.2 (RNA9.2s) and its derivatives with and without LNA-modification of the 5' and the 3'end (n, 5'LNA, 3'LNA, 5'3'LNA) are compared (see Table 2). FIG. 4B: Different LNA-modified versions of the sense and the antisense strand of siRNA9.2 were annealed to duplexes and transfected into PDC. After 36 hours, IFN-α production was measured in the supernatants (black bars). Results from five individual donors are depicted as mean values±SEM. In addition, HEK 293 cells stably expressing a construct of human TLR9 with a C-terminal YFP-tag were transfected with the same type of siRNA9.2 derivatives. Transfection with siRNA-duplexes targeting GFP, TLR2 or TLR4 mRNA served as controls. 20 hours after transfection the median fluorescence intensity of YFP-tag expression was analyzed by flow cytometry (open bars). Data are depicted as percentage of TLR9-expression referring to siRNA2.1 as 100% and the unmodified siRNA9.2 as 0%. Results are shown as mean values±SEM (n=3).

FIG. 5A: Murine bone-marrow cultures (129Sv) were stimulated with siRNA TLR9.2 duplex, sense or anti-sense strand or a 19mer poly(A)-oligonucleotide complexed to polycationic peptide. ODN 1826 (6 µg/ml) and R848 (1H-Imidazo(4,5-c)quinoline-1-ethanol(ethoxymethyl)-Alpha; 0.5 µg/ml) served as positive controls. After 36 hours, supernatants were collected and IFN-α production was assessed by ELISA. Data are presented as mean values±SEM from triplicates of pooled bone-marrow cultures from three individual mice. FIG. 5B: 5 µg of siRNA TLR2.1, TLR9.2, or single strands TLR9.2a (sense strand) or TLR9.2 as (anti-sense strand) were complexed with DOTAP and administered via i.v. injection to 129Sv mice (3 mice per group). DOTAP without RNA was included as a control. After seven hours serum was collected and IFN-α production was assessed by ELISA. Data are presented as mean values±SEM. FIG. 5C: 41 hours after injection, spleen cells were isolated and CD8+ T cells and MDCs were identified in spleen cells by using anti-CD3, anti-CD8, anti-CD11b and anti-CD11c antibodies. CD69 or CD86-expression was assessed using an appropriate isotype control Ab. Results from three mice per group are presented as mean values±SEM. FIG. 5D: The siRNA TLR9.2, CpG ODN 1826 (both 5 µg) or HBS with or without DOTAP-complexation were administered via i.v. injection to 129P2/OlaHsd mice (3 mice per group). After eighteen hours, serum was collected and IFN-α production was assessed by ELISA (left panel). In addition, CD86 expression was analysed on splenic MDCs 41 hours after injection (right panel). Data are presented as mean values±SEM.

FIG. 6A: Murine bone-marrow cultures from wild-type (black bars) or TLR7−/− (open bars) C57BL/6 mice were incubated with siRNA TLR9.2, with the sense strand or the antisense strand of TLR9.2 or a 19mer poly(A) oligonucleotide complexed with polycationic peptide. CpG ODN 1826 (TLR9) and loxoribine (TLR7) were used at a concentration of 6 µg/ml or 0.5 µg/ml respectively. Supernatants were collected 36 h after stimulation and IFN-α-production was assessed by ELISA. Data are presented as mean values±SEM from triplicates of pooled bone-marrow cultures from two individual mice. FIG. 6B: 5 µg of siRNA TLR9.2 was complexed with DOTAP and injected i.v. into either wildtype (black bars) or TLR7−/−(open bars) C57BL/6 mice. Two mice per group were used. After 7 and 18 hours serum was collected and IFN-α production was assessed by ELISA. FIG. 6C: 41 hours after injection, spleen cells were isolated. CD8+ and CD4+ T cells were identified in spleen cells by using anti-CD3 and anti-CD8 antibodies. CD69-expression was assessed using an appropriate isotype control antibody (grey bar). One representative histogram is shown for CD8+ T cells. The expression of CD69 or CD86 was analyzed on PDC (CD11c$^+$, CD11b$^-$ and B220$^{++}$) and myeloid dendritic cells (MDC: CD11c$^{++}$, CD11b$^{++}$ and B220$^-$). Expression of CD69 and CD86 is presented as means±SEM.

DETAILED DESCRIPTION

Figure 1:
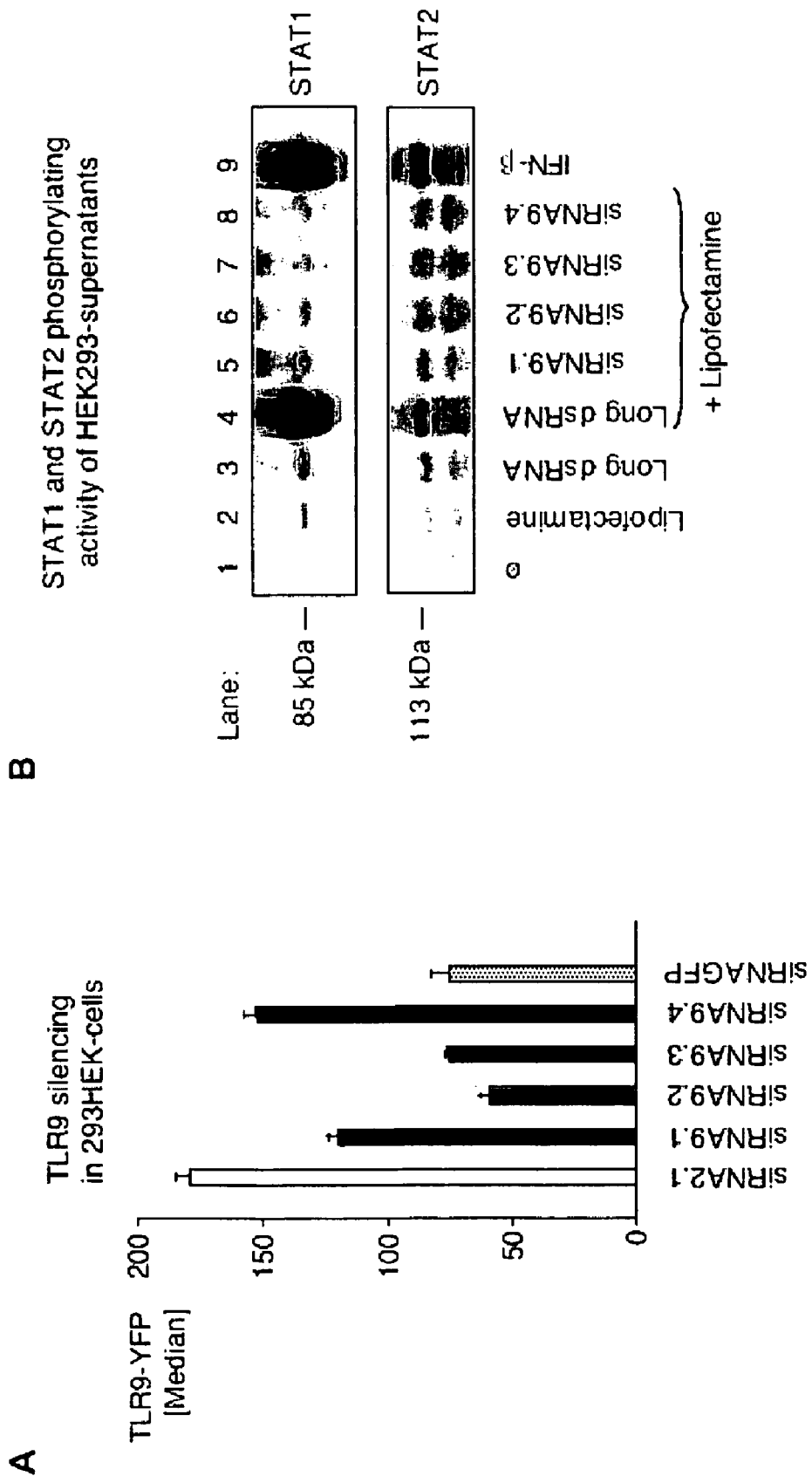
FIGS. 1A-1B: In HEK 293 cells siRNA can be used to inhibit TLR9 expression without inducing non-target-specific type I IFN-mediated STAT1- or STAT2-phosphorylating activity HEK 293 cells (50.000/well) were incubated with different RNA molecules and lipofectamine.

The invention is based, at least in part, on the discovery that a particular sequence motif in a single or double stranded RNA molecule is effective at stimulating an immune response via IFN induction, particularly in cells expressing TLR7, such as plasmacytoid dendritic cells (PDC). Based on this discovery, the present invention provides immunostimulatory oligonucleotide agents that can be used to stimulate IFN production in a mammal as well as methods of selectively designing single stranded antisense agents and double stranded iRNA agents so as to induce a wanted immune response or to avoid inducing an unwanted immune response.

Specifically, the present invention provides therapeutic compositions comprising a single stranded or double stranded oligonucleotide as an immunostimulatory agent as well as a method of using such composition for immunotherapy applications. The invention specifically provides methods and compositions for enhancing the immune response used for immunotherapy applications such as, but not limited to, treatment of cancer, autoimmune disorders, asthma, respiratory allergies, food allergies, and bacteria, parasitic, and viral infections in adult and pediatric human and veterinary applications. The invention further provides methods for making such compounds. In addition, compounds of the invention are useful as adjuvants in combination with DNA vaccines, antibodies, and allergens; and in combination with other immunostimulatory agents, chemotherapeutic agents, iRNA agents and/or antisense oligonucleotides.

The present invention provides oligonucleotide agents that comprise, consist of or consist essentially of the nucleotide sequence

5'-GUCCUUCAA-3'. (SEQ ID NO: 1)

In other embodiments, the oligonucleotide agent will consist of, consist essentially of or comprise 4 or more, 5 or more, 6 or more, 7 or more or 8 or more contiguous nucleotides from SEQ ID NO:1, preferably taken from the 5' end of this sequence, e.g. 5'-GUCC-3' (SEQ ID NO:2), 5'-GUCCU-3' (SEQ ID NO:3), 5'-GUCCUU-3' (SEQ ID NO:4), 5'-GUCCUUC-3' (SEQ ID NO:5), or 5'-GUCCUUCA-3' (SEQ ID NO:6).

As used herein, an oligonucleotide agent consists of SEQ ID NO:1 when it does not contain other nucleotides in the agent. As used herein, an oligonucleotide agent consists essentially of SEQ ID NO:1 when it contains no more than 1, 2, 3, or 4 other nucleotides in the agent. As used herein, an oligonucleotide agent comprises SEQ ID NO:1 when it contains other nucleotides in the agent. Preferably, such agents will contain no more than 21 other nucleotides and more preferably no more than from about 15 to about 10 other nucleotides in the agent where the agent does not comprise a double stranded structure. Oligonucleotide agents comprising a double stranded structure, e.g. iRNA agents, will contain no more than 21, 15 or 10 other nucleotides in a strand comprising SEQ ID NO:1, and preferably no more than 30, 24, or 19 nucleotides in a strand not comprising SEQ ID NO:1.

As used herein, the term "oligonucleotide" refers to a polynucleotide formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., $(R_p)$- or $(S_p)$-phosphorothioate, alkylphosphonate, or phosphotriester linkages).

The oligonucleotides of the invention can include naturally occurring nucleosides, modified nucleosides, or mixtures thereof, so long as they consist of, consist essentially of or comprise SEQ ID NO:1. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

As used herein, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

An "immunostimulatory" agent, or an agent that "stimulates an immune response" herein means an agent that stimulates in a cell in vitro or in an organism in vivo a response that is commonly understood to be part of the natural defenses of an organism against biological pathogens, e.g. the immune system. Such response can be, for example, without limitation, be the production of antibodies or cytokines, e.g. interferons, e.g. interferon alpha (IFN-α).

In another embodiment, the invention provides immunomodulatory oligonucleotide conjugates and oligonucleotide agent conjugates, for example comprising an immunomodulatory oligonucleotide or an oligonucleotide agent, as described above, and an antigen conjugated to the oligonucleotide agent at a position other than the accessible 5' end. In some embodiments, the non-nucleotidic linker comprises an antigen, which is conjugated to the oligonucleotide. In some other embodiments, the antigen is conjugated to the oligonucleotide at a position other than its 3' end. In some embodiments, the antigen produces a vaccine effect. Other oligonucleotide agent conjugates are further described below.

Where an oligonucleotide agent is conjugated to an antigen, the antigen is preferably selected from the group consisting of antigens associated with a pathogen, antigens associated with a cancer, antigens associated with an autoimmune disorder, and antigens associated with other diseases such as, but not limited to, veterinary or pediatric diseases. As used herein, the term "associated with" means that the antigen is present when the pathogen, cancer, auto-immune disorder, food allergy, respiratory allergy, asthma or other disease is present, but either is not present, or is present in reduced amounts, when the pathogen, cancer, auto-immune disorder, food allergy, respiratory allergy, or disease is absent.

The immunomodulatory oligonucleotide or oligonucleotide agent is covalently linked to the antigen, or it is otherwise operatively associated with the antigen. As used herein, the term "operatively associated with" refers to any association that maintains the activity of both oligonucleotide agent and antigen. Nonlimiting examples of such operative associations include being part of the same liposome or other such delivery vehicle or reagent. In embodiments wherein the oligonucleotide agent is covalently linked to the antigen, such covalent linkage preferably is at any position on the oligonucleotide agent other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In a preferred embodiment, the oligonucleotide or oligonucleotide agent is an iRNA agent, such as an antisense agent or siRNA agent. In that sense, oligonucleotide or oligonucleotide agent, as used herein, can also refer to a complex consisting of more than one, and preferably two, oligonucleotide molecules, which occur essentially only in direct association, e.g. by hybridizing to each other, under certain conditions, such as those found in the serum of mammals, e.g. humans, or in the cytoplasm of mammalian, and particularly human, cells. To be an oligonucleotide agent hereunder, at least one of the more than one oligonucleotide molecules forming the complex consists, consists essentially of, or comprises SEQ ID NO:1.

An iRNA agent, as used herein, is an agent capable of specifically interfering with the expression of a target gene, such as an antisense or siRNA agent. Typically, an iRNA agent comprises an oligonucleotide sequence which is complementary to a part of an mRNA encoded by the target gene. It interferes with the expression of the target gene by any mechanism, e.g. by blocking the translation of the mRNA, by initiating the degradation of the mRNA, e.g. via an RNA interference mechanism, or by blocking the transcription of the gene, e.g. via DNA methylation.

iRNA Agent Design

The present invention further provides methods of designing/selecting an iRNA agent, such as an antisense or siRNA agent, such that it will either induce an inflammatory response or avoid inducing an inflammatory response. Specifically, this method comprises the step of either including SEQ ID NO:1, or a fragment thereof in an oligonucleotide agent, such as an antisense or siRNA agent, when an IFN/inflammatory response is wanted or not including this sequence in the agent when an inflammatory response is not wanted.

Accordingly, the present invention provides, inter alia, iRNA agents comprising an antisense strand and, optionally, a sense strand, comprising a sequence of at least 15, 16, 17, 18, 19, 20, 21 or 23 nucleotides, wherein at least one of the sequences of the antisense and the optional sense strand comprises SEQ ID NO:1 when IFN production is wanted and wherein none of the antisense strand and the optional sense strand will contain this sequence when IFN production is to be avoided.

The antisense strand of an iRNA agent should be equal to or at least, 15, 16 17, 18, 19, 25, 29, 40, or 50 nucleotides in length. It should be equal to or less than 50, 40, or 30, nucleotides in length. Preferred ranges are 15-30, 17 to 25, 19 to 23, and 19 to 21 nucleotides in length.

The sense strand, if any, of an iRNA agent should be equal to or at least 15, 16 17, 18, 19, 25, 29, 40, or 50 nucleotides in length. It should be equal to or less than 50, 40, or 30 nucleotides in length. Preferred ranges are 15-30, 17 to 25, 19 to 23, and 19 to 21 nucleotides in length.

The double stranded portion, if any, of an iRNA agent should be equal to or at least, 15, 16 17, 18, 19, 20, 21, 22, 23, 24, 25, 29, 40, or 50 nucleotide pairs in length. It should be equal to or less than 50, 40, or 30 nucleotides pairs in length. Preferred ranges are 15-30, 17 to 25, 19 to 23, and 19 to 21 nucleotides pairs in length.

In designing iRNA agents according to the invention, it may be advantageous to first identify a region in an mRNA sequence of a target gene which is either complementary (for use in antisense oligonucleotides and siRNA antisense strands) or identical (for use in an siRNA sense strand) to 4 or more, 5 or more, 6 or more, 7 or more or 8 or more contiguous nucleotides from SEQ ID NO:1. The iRNA agent can then be chosen to comprise the sequence complementary or identical sequence to this region, plus a number of suitable additional nucleotides to confer target gene expression inhibitory activity. Therein, SEQ ID NO:1 may be comprised anywhere within the iRNA agent, e.g. in a 3'- or 5'-terminal region, or anywhere within, of either a sense or antisense strand of the iRNA agent.

However, where it is desired to inhibit a certain gene where its mRNA does not comprise a region of complete complementarity or identity to SEQ ID NO:1, an iRNA agent comprising mismatches to the target gene mRNA may also be used. Since mismatches are most tolerated in the terminal regions of either strand of, for example, an siRNA, the mismatches will best be introduced in these terminal regions. For example, the 3'-most or 5'-most 4, 5, 6, 7, 8 or 9 nucleotides of the sense strand or the 3'-most 4, 5, 6, 7, 8 or 9 nucleotides of the antisense strand of an siRNA may be chosen from SEQ ID NO:1, wherein not more than 1, not more than 2, or not more than 3 nucleotides represent a mismatch to the target mRNA, and the remaining nucleotides are chosen fully identical or complementary to the target mRNA. The nucleotides in positions 2-9 (counting 5'→3') of the antisense strand, however, are believed to be critical for target mRNA recognition (Haley, B., and Zamore, P. D., *Nat Struct Mol Biol*, 11, 599-606 (2004)). Therefore, it is preferred that in this region (sometimes referred to as the "seed region") there is perfect complementarity to the target mRNA.

In such embodiment, said target gene can be essentially any gene the sequence of which enables the design of a fully matched or partly mismatched iRNA agent as described above. The gene may, for example be a mammalian gene, e.g. a human gene. For example, without limitation, such a gene may be an oncogene, a gene involved in an immune response, a gene involved in metabolism, or a gene encoding a growth factor, a transcription factor, or a receptor. Table 7 contains a non-limiting list of names of exemplary gene transcripts, as obtained from BLAST searching databases of human mRNA sequences, which may be inhibited in this fashion, as they comprise a sequence identical or complementary to SEQ ID NO:1. Alternatively, the target gene may be a gene from an organism that is pathogenic to animals, preferably mammals, more preferably humans, such as a bacterium or a virus.

iRNA Agent Chemistry iRNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Enhanced Nuclease Resistance

For increased nuclease resistance and/or binding affinity to a target mRNA, an oligonucleotide agent can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'-$OCH_3$, 2'-O-allyl, 2'-C-allyl, and 2'-fluoro.

To maximize nuclease resistance, the 2' modifications can be used in combination with one or more phosphate linker modifications (e.g., phosphorothioate).

The inclusion of furanose sugars in the oligonucleotide backbone can also decrease endonucleolytic cleavage. An oligonucleotide agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

Tethered Ligands

The properties of an oligonucleotide agent, including its pharmacological properties, can be influenced and tailored, for example, by the introduction of ligands, e.g. tethered ligands. An oligonucleotide agent comprising a tethered ligand may also be referred to herein as a conjugate or bioconjugate.

A wide variety of entities, e.g., ligands, can be tethered to an oligonucleotide agent, e.g., to the carrier of a ligand-conjugated monomer subunit. Examples are described below in the context of a ligand-conjugated monomer subunit but that is only preferred, entities can be coupled at other points to an oligonucleotide agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_nNH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an oligonucleotide agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases.

General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one embodiment, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In another embodiment, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another embodiment, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Preferred ligands confer to the agent the ability to bind to a cell, preferably to a cell of a specific cell type most relevant to the disease state in question. For example, the asialoglycoprotein receptor (ASGPr) (Wu and Wu, 1987, J. Biol. Chem. 262, 4429-4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligosaccharide chain, for example, triatennary structures are bound with greater affinity than biatenarry or monoatennary chains (Baenziger and Fiete, 1980, Cell, 22, 611-620; Connolly et al., 1982, J. Biol. Chem., 257, 939-945). Lee and Lee, 1987, Glycoconjugate J., 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, J. Med. Chem., 24, 1388-1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavailability, pharmacodynamics, and pharmacokinetic parameters can be modulated through the use of nucleic acid bioconjugates of the invention. Non-limiting examples of such bioconjugates are described in Vargeese et al., U.S. Ser. No. 10/201,394, filed Aug. 13, 2001; and Matulic-Adamic et al., U.S. Ser. No. 60/362,016, filed Mar. 6, 2002.

5'-Phosphate Modifications

In other embodiments, oligonucleotide agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

Formulation

The oligonucleotide agents described herein can be formulated for administration to a subject, preferably for systemic administration, e.g. parenteral or oral administration, including, without limitation, intravenous, intramuscular, intraperitoneal, rectal, intradermal, subcutaneous, or percutaneous administration, or for the targeted delivery to tissues, e.g. the lungs and nasal passage (respiratory tissues), e.g. via inhalation or intranasal administration, the liver, kidney, spleen, brain, spinal cord, eye, skin, gut, mucosa, placenta, or any other tissue or organ that is a preferred target for the effect of the oligonucleotide agent.

For ease of exposition, the formulations, compositions, and methods in this section are discussed largely with regard to unmodified oligonucleotide agents. It should be understood, however, that these formulations, compositions, and methods can be practiced with other oligonucleotide agents, e.g., modified oligonucleotide agents, and such practice is within the invention.

A formulated oligonucleotide agent composition can assume a variety of states. In some examples, the composition is at least partially crystalline, uniformly crystalline, and/or anhydrous (e.g., less than 80, 50, 30, 20, or 10% water). In another example, the oligonucleotide agent is in an aqueous phase, e.g., in a solution that includes water, this form being the preferred form for parenteral administration.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the oligonucleotide agent composition is formulated in a manner that is compatible with the intended method of administration.

An oligonucleotide agent preparation can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as $Mg^{2+}$), salts, nuclease inhibitors (e.g., a broad specificity nuclease inhibitor such as RNAsin) and so forth.

In one embodiment, the oligonucleotide agent preparation includes another oligonucleotide agent, e.g., an siRNA agent that can mediate RNAi with respect to a target gene. In such a use, a target gene is disrupted in a cell as well as the cell being stimulated to produce IFN using the oligonucleotide agent of the present invention. Such cotherapy is important in treating disorders such as cancers, and viral infections.

Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Patent Application Publication No. U.S. 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262.

In another embodiment, the nucleic acid molecules of the invention can also be formulated or complexed with polyethyleneimine and derivatives thereof, such as polyethyleneimine-polyethyleneglycol-N-acety-lgalactosamine (PEI-PEG-GAL) or polyethyleneimine-polyethyleneglycol-tri-N--acetylgalactosamine (PEI-PEG-triGAL) derivatives. In one embodiment, the nucleic acid molecules of the invention are formulated as described in U.S. Patent Application Publication No. 20030077829, incorporated by reference herein in its entirety.

In one embodiment, an oligonucleotide agent of the invention is complexed with membrane disruptive agents such as those described in U.S. Patent Application Publication No. 20010007666, incorporated by reference herein in its entirety including the drawings. In another embodiment, the membrane disruptive agent or agents and the oligonucleotide agent are also complexed with a cationic lipid or helper lipid molecule, such as those lipids described in U.S. Pat. No. 6,235,310, incorporated by reference herein in its entirety including the drawings.

In one embodiment, an oligonucleotide agent of the invention is complexed with delivery systems as described in U.S. Patent Application Publication No. 2003077829 and International PCT Publication Nos. WO 00/03683 and WO 02/087541, all incorporated by reference herein in their entirety including the drawings.

In one embodiment, the nucleic acid molecules of the invention are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the nucleic acid compositions of the invention can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight.

Aerosols of liquid particles comprising a nucleic acid composition of the invention can be produced by any suitable means, such as with a nebulizer (see for example U.S. Pat. No. 4,501,729). Nebulizers are commercially available devices which transform solutions or suspensions of an active ingredient into a therapeutic aerosol mist either by means of acceleration of a compressed gas, typically air or oxygen, through a narrow venturi orifice or by means of ultrasonic agitation. Suitable formulations for use in nebulizers comprise the active ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride or other suitable salts. Optional additives include preservatives if the formulation is not prepared sterile, for example, methyl hydroxybenzoate, anti-oxidants, flavorings, volatile oils, buffering agents and emulsifiers and other formulation surfactants. The aerosols of solid particles comprising the active composition and surfactant can likewise be produced with any solid particulate aerosol generator. Aerosol generators for administering solid particulate therapeutics to a subject produce particles which are respirable, as explained above, and generate a volume of aerosol containing a predetermined metered dose of a therapeutic composition at a rate suitable for human administration. One illustrative type of solid particulate aerosol generator is an insufflator. Suitable formulations for administration by insufflation include finely comminuted powders which can be delivered by means of an insufflator. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant.

The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, emulsifiers and other formulation surfactants, such as oleic acid or sorbitan trioleate, anti-oxidants and suitable flavoring agents. Other methods for pulmonary delivery are described in, for example U.S. Patent Application No. 20040037780, and U.S. Pat. Nos. 6,592,904; 6,582,728; 6,565,885.

In one embodiment, nucleic acid molecules of the invention are administered to the central nervous system (CNS) or peripheral nervous system (PNS). Experiments have demonstrated the efficient in vivo uptake of nucleic acids by neurons. As an example of local administration of nucleic acids to nerve cells, Sommer et al., 1998, Antisense Nuc. Acid Drug Dev., 8, 75, describe a study in which a 15mer phosphorothioate antisense nucleic acid molecule to c-fos is administered to rats via microinjection into the brain. Antisense molecules labeled with tetramethylrhodamine-isothiocyanate (TRITC) or fluorescein isothiocyanate (FITC) were taken up by exclusively by neurons thirty minutes post-injection. A diffuse cytoplasmic staining and nuclear staining was observed in these cells. As an example of systemic administration of nucleic acid to nerve cells, Epa et al., 2000, Antisense Nuc. Acid Drug Dev., 10, 469, describe an in vivo mouse study in which beta-cyclodextrin-adamantane-oligonucleotide conjugates were used to target the p75 neurotrophin receptor in neuronally differentiated PC12 cells. Following a two week course of IP administration, pronounced uptake of p75 neurotrophin receptor antisense was observed in dorsal root ganglion (DRG) cells. In addition, a marked and consistent down-regulation of p75 was observed in DRG neurons. Additional approaches to the targeting of nucleic acid to neurons are described in Broaddus et al., 1998, J. Neurosurg., 88(4), 734; Karle et al., 1997, Eur. J. Pharmocol., 340(2/3), 153; Bannai et al., 1998, Brain Research, 784(1,2), 304; Rajakumar et al., 1997, Synapse, 26(3), 199; Wu-pong et al., 1999, BioPharm, 12(1), 32; Bannai et al., 1998, Brain Res. Protoc., 3(1), 83; Simantov et al., 1996, Neuroscience, 74(1), 39. Nucleic acid molecules of the invention are therefore amenable to delivery to and uptake by cells in the CNS and/or PNS.

The delivery of nucleic acid molecules of the invention to the CNS is provided by a variety of different strategies. Traditional approaches to CNS delivery that can be used include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Other approaches can include the use of various transport and carrier systems, for example though the use of conjugates and biodegradable polymers. Furthermore, gene therapy approaches, for example as described in Kaplitt et al., U.S. Pat. No. 6,180,613 and Davidson, WO 04/013280, can be used to express nucleic acid molecules in the CNS.

In one embodiment, delivery systems of the invention include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in this invention include the following: (1) CellFectin, 1:1.5 (M/M) liposome formulation of the cationic lipid N,NI,NII,NIII-tetramethyl-N,NI,NII,NIII--tetrapalmity-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniummethylsulfate) (Boehringer Manheim); and (4) Lipofectamine, 3:1 (M/M) liposome formulation of the polycationic lipid DOSPA and the neutral lipid DOPE (GIBCO BRL).

In one embodiment, delivery systems of the invention include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

In one embodiment, oligonucleotide agents of the invention are formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002, Phramaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999., PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; and Sagara, U.S. Pat. No. 6,586,524, incorporated by reference herein.

The present invention therefore includes pharmaceutically acceptable formulations of the compounds described. These formulations include salts of the above compounds, e.g., acid addition salts, for example, salts of hydrochloric, hydrobromic, acetic acid, and benzene sulfonic acid.

The invention also features compositions comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Methods of Modulating an Immune Response Via IFN Production

The invention further provides a method for modulating an immune response in a vertebrate. The method comprises the step of administering to the vertebrate an immuno-stimulatory oligonucleotide of the invention.

As used herein, the term "vertebrate" includes, without limitation, a fish, bird, or mammal. As used herein, the term "mammal" includes, without limitation rats, mice, cats, dogs, horses, cattle, cows, pigs, rabbits, non-human primates, and humans.

As used herein, "modulating an immune response" means causing an increase in, or activation of one or more of B-cell induction, T-cell induction, cytokine induction, natural killer cell induction, specific cell surface marker expression, chemokine induction and activation of antigen presenting cells, such as dendritic cells, monocytes and macrophages. Particularly, such immune response will involve the production of IFN in cells expressing the TLR7 protein, such as PDC.

The present invention further provides a method for treating a vertebrate having a disease that can be ameliorated by inducing IFN production. The method according to this embodiment of the invention comprises administering to the vertebrate an oligonucleotide agent of the present invention, e.g. an agent consisting of, consisting essential of or comprising SEQ ID NO:1. In such a use, an oliognucloetide agent of the present invention is used to stimulate IFN production in a vertebrate to directly treat the condition or augment other therapies. There are well recognized clinical settings where selective activation of IFN production is wanted.

In another embodiment, the invention provides methods for therapeutically treating a patient having a disease or disorder, such methods comprising administering to the patient an immunomodulatory oligonucleotide, immunomodulatory oligonucleotide conjugate, oligonucleotide agent or oligonucleotide agent conjugate according to the invention. In various embodiments, the disease or disorder to be treated is cancer, an autoimmune disorder, airway inflammation, inflammatory disorders, allergy, asthma or a disease caused by a pathogen. Pathogens include bacteria, parasites, fungi, viruses, viroids and prions. Administration is carried out as described elsewhere herein.

As used herein, the term "allergy" includes, without limitation, food allergies and respiratory allergies. The term "airway inflammation" includes, without limitation, asthma.

As used herein, the term "autoimmune disorder" refers to disorders in which "self" proteins undergo attack by the immune system. Such term includes autoimmune asthma.

In any of the methods of the invention, the immunomodulatory oligonucleotide, immunomodulatory oligonucleotide conjugate, oligonucleotide agent or oligonucleotide agent conjugate can be administered in combination with any other agent useful for treating the disease or condition that does not diminish the immunostimulatory effect of the oligonucleotide agent. For example, in the treatment of cancer, it is contemplated that the immunomodulatory oligonucleotide, immunomodulatory oligonucleotide conjugate, oligonucleotide agent or oligonucleotide agent conjugate may be administered in combination with a chemotherapeutic compound Examples of cellular proliferative and/or differentiative disorders include cancer, e.g., a carcinoma, sarcoma, metastatic disorder or hematopoietic neoplastic disorder, such as a leukemia. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state or condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

The pharmaceutical compositions of the present invention can also be used to treat a variety of hematopoietic disorders. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, the invention relates to methods for treating viral diseases, including but not limited to hepatitis C, hepatitis B, herpes simplex virus (HSV), HIV-AIDS, poliovirus, and smallpox virus. Examples of (+) strand RNA viruses include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus). In a preferred embodiment, the virus is hepacivirus, the hepatitis C virus.

Pharmaceutical Compositions

In one embodiment, the invention relates to a pharmaceutical composition containing an oligonucleotide agent, as described in the preceding sections, and a pharmaceutically acceptable carrier, as described below. A pharmaceutical composition including the oligonucleotide agent is useful for treating a disease that can be ameliorated by inducing IFN production. In this embodiment of the invention, the oligonucleotide agent of the invention is formulated as described below. The pharmaceutical compositions of the present invention are administered in dosages sufficient to induce IFN production. Where the pharmaceutical composition comprises an iRNA agent, the dosage will also be sufficient to inhibit the expression or activity of the target gene. Compositions containing the oligonucleotide agent of the invention can be administered at surprisingly low dosages. A maximum dosage of 5 mg oligonucleotide agent per kilogram body weight per day may be sufficient to induce IFN production, and, where applicable, to inhibit or completely suppress the expression or activity of the target gene.

Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

In general, a suitable dose of the oligonucleotide agent will be in the range of 0.001 to 500 milligrams per kilogram body weight of the recipient per day (e.g., about 1 microgram per kilogram to about 500 milligrams per kilogram, about 100 micrograms per kilogram to about 100 milligrams per kilogram, about 1 milligrams per kilogram to about 75 milligrams per kilogram, about 10 micrograms per kilogram to about 50 milligrams per kilogram, or about 1 microgram per kilogram to about 50 micrograms per kilogram). The pharmaceutical composition may be administered once per day, or the oligonucleotide agent may be administered as two, three, four, five, six or more sub-doses at appropriate intervals throughout the day. In that case, the oligonucleotide agent contained in each sub-dose must be correspondingly smaller in order to achieve the total daily dosage. The dosage unit can also be compounded for delivery over several days, e.g., using a conventional sustained release formulation which provides sustained release of the oligonucleotide agent over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual oligonucleotide agent encompassed by the invention can be made using conventional methodologies or on the basis of in vivo testing using an appropriate animal model, as described elsewhere herein.

The pharmaceutical compositions encompassed by the invention may be administered by any means known in the art including, but not limited to oral or parenteral routes, including intravenous, intramuscular, intraperitoneal, subcutaneous, transdermal, airway (aerosol), ocular, rectal, vaginal and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

For oral administration, the oligonucleotide agent useful in the invention will generally be provided in the form of tablets or capsules, as a powder or granules, or as an aqueous solution or suspension. Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of oligonucleotide agent in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce oligonucleotide agents into cell cultures, surprisingly these methods and agents are not necessary for uptake of the oligonucleotide agent in vivo. The oligonucleotide agents of the present invention are particularly advantageous in that they do not require the use of an auxiliary agent to mediate uptake of the oligonucleotide agent into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The pharmaceutical compositions can also include encapsulated formulations to protect the oligonucleotide agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

A preferred pharmaceutical composition according to the present invention is a vaccine. A vaccine should contain an antigen besides the oligonucleotide according to the present invention. The potential of this antigen to raise a protection/immune response of the vaccinated individual is strongly increased by combining it with the oligonucleotides according to the present invention, especially due to their immunostimulatory activity.

A vaccine can contain a whole variety of different antigens. Examples of antigens are whole-killed organisms such as inactivated viruses or bacteria, fungi, protozoa or even cancer cells. Antigens may also consist of subfractions of these organisms/tissues, of proteins, or, in their most simple form, of peptides. Antigens can also be recognised by the immune system in form of glycosylated proteins or peptides and may also be or contain polysaccharides or lipids. Short peptides can be used since for example cytotoxic T cells (CTL) recognize antigens in form of short usually 8-11 amino acids long peptides in conjunction with major histocompatibility complex (MHC) (Rammensee et al., *Immunogenetics*, 41, 178-228 (1995)). B cells recognize longer peptides starting at around 15 amino acids (Harrow et al, Cold Spring Harbor: Cold Spring Harbor Laboratory, (1988)). By contrast to T cell epitopes, the three dimensional structure of B cell antigens may also be important for recognition by antibodies. In order to obtain sustained, antigen-specific immune responses, adjuvants are helpful to trigger immune cascades that involve all cells of the immune system necessary. Primarily, adjuvants are acting, but are not restricted in their mode of action, on so-called antigen presenting cells (APCs). These cells usually first encounter the antigen(s) followed by presentation of processed or unmodified antigen to immune effector. Intermediate cell types may also be involved. Only effector cells with the appropriate specificity are activated in a productive immune response. The adjuvant may also locally retain antigens and co-injected other factors. In addition the adjuvant may act as a chemoattractant for other immune cells or may act locally and/or systemically as a stimulating agent for the immune system.

The antigens to be used in the present compositions are not critical. Preferably, proteins or peptides derived from a viral or a bacterial pathogen or from fungi or parasites are used as such antigens (including derivatized antigens or glycosylated or lipidated antigens or polysaccharides or lipids). Another preferred source of antigens are tumor antigens. Preferred pathogens are selected from human immunodeficiency virus (HIV), hepatitis A and B viruses, hepatitis C virus (HCV), rous sarcoma virus (RSV), Epstein Barr virus (EBV) Influenza virus, Rotavirus, *Staphylococcus aureus*, *Chlamydia pneumonias*, *Chlamydia trachomatis*, *Mycobacterium tuberculosis*, *Streptococcus pneumonias*, *Bacillus anthracis*, *Vibrio cholerae*, *Plasmodium* sp. (*Pl. falciparum*, *Pl. vivax*, etc.), *Aspergillus* sp. or *Candida albicans*. Antigens may also be molecules expressed by cancer cells (tumor antigens). The derivation process may include the purification of a specific protein from the pathogen/cancer cells, the inactivation of the pathogen as well as the proteolytic or chemical derivatization or stabilisation of such a protein. In the same way also tumor antigens (cancer vaccines) or autoimmune antigens may be used in the pharmaceutical composition according to the present invention. With such compositions a tumor vaccination or a treatment for autoimmune diseases may be performed.

In the case of peptide antigens the use of peptide mimitopes/agonists/superagonists/antagonists or peptides changed in certain positions without affecting the immunologic properties or non-peptide mimitopes/agonists/superagonists/antagonists (reviewed in Sparbier and Walden, *Curr Opin Immunol*, 11, 214-218 (1999)) is included in the current invention. Peptide antigens may also contain elongations either at the carboxy or at the amino terminus of the peptide antigen facilitating interaction with the polycationic compound(s) or the immunostimulatory compound(s). For the treatment of autoimmune diseases peptide antagonists may be applied. Antigens may also be derivatized to include molecules enhancing antigen presentation and targeting of antigens to antigen presenting cells.

Toxicity and therapeutic efficacy of an oligonucleotide agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. oligonucleotide agents that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any oligonucleotide agent used in the method of the invention, the therapeutically effective dose can be estimated initially from cell culture assays. A dose may be formulated in animal models to achieve a circulating plasma concentration range of the oligonucleotide agent or of IFN, or, when appropriate, of the polypeptide product of a target sequence of an iRNA agent (e.g., achieving a decreased concentration of the polypeptide) that includes the IC50 (i.e., the concentration of the test oligonucleotide agent which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, oligonucleotide agents relating to the invention can be administered in combination with other known agents effective in treating viral infections and diseases. In any event, the administering physician can adjust the amount and timing of oligonucleotide agent administration on the basis of results observed using standard measures of efficacy known in the art or described herein.

A number of embodiments of the invention have been described. Nevertheless, it will be understood that various modifications may be made without departing from the spirit and scope of the invention. Other embodiments are in the claims.

EXAMPLES

Example 1

Isolation of Plasmacytoid Dendritic Cells

PBMC were obtained from whole blood of healthy individuals by Ficoll-Hypaque density gradient centrifugation (Biochrom, Berlin, Germany). PDC were isolated by MACS using the BDCA-4 dendritic cell isolation kit from Miltenyi Biotec. Briefly, PDC were labeled with anti-BDCA-4 Ab coupled to colloidal paramagnetic microbeads and passed through a magnetic separation column once (LS column; Miltenyi Biotec). The purity of isolated PDC (lineage-negative, MHC-II-positive, and CD123-positive cells) was between 75% and 100%. Contaminating cells were mainly T cells. Viability was >95% as determined by trypan blue exclusion.

Cell Culture

Isolated PDC were cultured in 96-well flat-bottom plates at a concentration of $5 \times 10^4$ cells in 150 µl OPTIMEM (Invitrogen, Karlsruhe, Germany) supplemented with 10 ng/ml IL-3 (R&D Systems, Wiesbaden, Germany). HEK 293 cells stably transfected with a construct containing the human TLR9 gene with a C-terminal yellow fluorescent protein (YFP) tag were kindly provided by D. Golenbock (Worcester, Mass.). HEK 293 cells were cultured in RPMI 1640 culture medium (Biochrom) supplemented with 10% (v/v) fetal calf serum (BioWhittaker, Walkersville, Md.), 1.5 mM L-glutamine, 100 U/ml penicillin, and 100 µg/ml streptomycin (all from Sigma-Aldrich, Munich, Germany). EBV-negative Burkitt's lymphoma cell line BL41 was grown in RPMI 1640 (PAA, Linz, Austria), supplemented with 10% (v/v) fetal calf serum (Biochrom), 2 mM L-glutamine, 0.1 mg/ml penicillin/streptomycin and 1% 1 mM pyruvate (all from PAA). Cells were incubated at 37° C. and 5% $CO_2$.

In Vitro Cell Stimulation, Transfection and Electroporation

CpG ODN were provided by Coley Pharmaceutical Group (Wellesley, Mass.) (underlined letters, phosphorothioate linkage 3' of the base; bold letters, CpG dinucleotides):

```
ODN 2216: 5'-GGGGGACGATCGTC
GGGGG+EEG-3'; SEQ ID NO: 7

ODN 1826: 5'-TCCATGACGTTCCTGACGTT-3'. SEQ ID NO: 89
```

R848 was purchased from Invivogen (Toulouse, France). R848 and ODN 2216 were added at a final concentration of 500 ng/ml and 3 µg/ml respectively. The siRNA sequences (see table 1) were synthesized and annealed by Dharmacon (Lafayette, Colo.). siRNA was transfected with lipofectamine 2000 (Invitrogen, Karlsruhe, Germany). If not indicated otherwise, 200 ng of nucleic acid were mixed with 25 µl of OPTIMEM. In a separate tube, 0.5 µl of lipofectamine was added to 25 µl of OPTIMEM and incubated for 5 min at room temperature. For complex formation, both solutions were mixed, incubated for an additional 20 min at room temperature, and added to cells (100 µl) in a 96-well plate (final volume 150 µl). Cells in transfection solution were incubated at 37° C. without additional washing.

For electroporation, 250.000 PDC were resuspended in 400 µl "isoosmolar electroporation-buffer" (Eppendorf, Hamburg, Germany) with or without siRNA (2.5 µg/ml) and pulsed once with at 100V for 50 µs (Multiporator, Eppendorf). After 5 minutes 800 µl complete medium was added and cells were incubated in 24-well flat bottom wells for additional 36 h.

Mouse Studies

For in vivo stimulation, 129P2/OlaHsd or 129Sv mice were anesthetized and 200 µl containing 5 µg CpG ODN 1826 or siRNA TLR9.2 with or without prior 1,2-dioleoyloxy-3-trimethylammonium-propane (DOTAP)-complexation (30 µl DOTAP (Boehringer Mannheim) were mixed with 5 µg of nucleic acids in 170 µl of Hepes-buffered saline (HBS)) were injected i.v. into the retro-orbital vein. Control mice received either HBS alone (control) or HBS and DOTAP (DOTAP). Whole blood samples were obtained by tail clippings at either 7 hours, 18 hours or 24 hours after injection. Serum was prepared from whole blood by coagulation for 30 min at 37° C. and subsequent centrifugation.

Detection of Cytokines

Because total IFN-α is comprised of 14 different isoforms, the quantity of IFN-α measured by ELISA depends on the specificity of the antibody used for the detection of these isoforms, and thus is not identical between different ELISA. For this study, the IFN-α kit by Bender MedSystems (Graz, Austria) (detection range 8-500 pg/ml) was used. This ELISA detects most of IFN-α isoforms, but not IFN-B and IFN-F. The human TNF-α ELISA (detection range 8 to 500 pg/ml) and the human IL-6 ELISA (detection range 5 to 300 pg/ml) were from BD PharMingen (Heidelberg, Germany). Murine IFN-α was determined using the mouse IFN-α ELISA kit from PBL Biomedical Laboratories (Piscataway, USA). All ELISA procedures were performed as recommended by the manufacturer.

Flow Cytometry

Flow cytometric data were acquired on a BD Biosciences FACSCalibur (Heidelberg, Germany) equipped with two lasers (excitation at 488 nm and 635 nm wavelength). In general, cells were stained for 20 min at 4° C. with the indicated specific antibodies and the appropriate isotype controls. Human PDC were identified by positive staining with anti-CD123 PE and anti-MHC II PerCP and negative staining with anti-lineage FITC. Costimulatory molecule expression was determined by using anti-CD86 APC (all BD PharMingen). For PDC survival, cells were harvested 36 h after stimulation and the absolute number of viable cells per 50 µl aspirated volume was determined by flow cytometry. Viability of PDC was determined by staining negative for TO-PRO-3 iodide (Molecular Probes, Eugene, Oreg.) and a morphology-based live gate. For phenotypic analysis of murine MDC ($CD11c^{++}$, $CD11b^{++}$ and $B220^-$) and PDC ($CD11c^+$, $CD11b^-$ and $B220^{++}$) freshly isolated spleen cells were stained with anti-CD86 FITC, anti-CD45R/B220 PE, anti-CD11b PerCP and anti-CD11c APC (all BD PharMingen). Activation of splenic NK cells and T cells was determined by anti-CD69 PE on anti-pan-NK FITC-positive cells (NK cells) and anti-CD3 APC-positive cells (T cells) (all BD PharMingen). Data were analyzed using CellQuest (BD Biosciences) or FlowJo software (version 2.5.1; Tree Star, Stanford, Calif.).

Western-Blot Analysis

The cells were washed once in phosphate-buffered saline (PBS) counted and lysed by resuspension in Laemmli sample buffer ($10^6$ cells/50 µl) followed by 10 sec of sonication. The samples were separated on SDS-polyacrylamide gels (10%) and transferred onto nitro-cellulose membranes (Hybond-ECL, Amersham). Following transfer, the membranes were stained in Ponceau Red to verify that equal amounts of protein were loaded. The membranes were then washed in TBST (tris 10 mM pH 8.0, NaCl 30 mM, 0.1% Tween) for 5 min and incubated for 30 min in TBST-MLK (TBST supplemented with 5% dried skimmed milk). After rinsing with water twice, specific antibodies (1:1000) in TBST-MLK were added for 1 h or overnight at 4° C. After rinsing twice with water and three washes of 5 min with TBST, the secondary antibodies conjugated with horseradish peroxidase (1:3000 in TBS-MLK) were added for 1.5 h, followed by 3 times rinsing with water, three washes of 5 min in TBST and 5 times rinsing with water. Bands were visualized on ECL films (Amersham) by enhanced chemiluminescence following the supplier's procedure (Amersham). Antibodies to the following proteins were used: phospho (tyrosine 701)-STAT1 (New-England Biolabs, Beverly, Mass.) and phospho (tyrosine 689)-STAT2 (Upstate, Waltham, Mass.).

Statistical Analysis

Data are expressed as means±SEM. Statistical significance of differences was determined by the paired two-tailed Student's t-test. Differences were considered statistically significant for p<0.05. Statistical analyses were performed using StatView 4.51 software (Abacus Concepts Inc., Calabasas, Calif.).

Specific siRNA-Mediated Inhibition of TLR9 Expression in HEK 293 Cells

The plasmacytoid dendritic cell (PDC) has been identified as the key sensor of CpG motifs. Selective inhibition of TLR9 in PDC with siRNA may allow analysis of the involvement of TLR9 in the recognition of viruses and of different types of CpG motif containing oligodesoxynucleotides (CpG ODN). We established siRNA-mediated downregulation of TLR9 in a HEK 293 cell line stably transfected with a construct containing the human TLR9 gene with a C-terminal yellow fluorescent protein (YFP) tag. Four siRNA molecules (TLR9.1, TLR9.2, TLR9.3, TLR9.4) targeting the human TLR9 mRNA were designed (Table 1). A standard BLAST-search ensured that these siRNA target sequences had no homologies with other human genes. siRNA targeting the human TLR2 mRNA was used as negative control, and a previously established siRNA targeting the C-terminal YFP tag of the TLR9 construct was used as a positive inhibition control (see Table 1). Adherent HEK 293cells were transfected with 200 ng siRNA using lipofectamine in 96-well plates. After 20 hours, 30 hours and 54 hours, HEK 293cells were harvested and expression of TLR9 was assessed by quantifying YFP fluorescence intensity by flow cytometry. At all three times points analyzed, two of the four TLR9-specific siRNA tested (TLR9.2 and TLR9.3) showed a strong inhibition of the TLR9-YFP fusion protein expression that was in the same range as the anti-YFP siRNA used as a positive inhibition control (TLR9 expression after 20 hours shown in FIG. 1A; 30 hours: TLR2.1: 151±10; TLR9.1: 71±10; TLR9.2: 43±2; TLR9.3: 48±2; TLR9.4: 119±5; GFP: 37±3; 54 hours: TLR2.1: 167±8, TLR9.1: 65±4; TLR9.2: 32±1; TLR9.3: 34±2; TLR9.4: 110±7; GFP: 24±1).

In order to exclude the possibility that downregulation of the target gene in HEK 293 cells is associated with non-target specific type I IFN induction, we analyzed the supernatants of HEK 293 cells for type I IFN activity. The induction of STAT1 and STAT2 phosphorylation in BL41 cells was used as a highly sensitive measure of type I IFN. No type I IFN activity was detected in the supernatants of HEK 293 cells transfected with the four different anti-TLR9 siRNA TLR9.1, TLR9.2, TLR9.3, TLR9.4 (FIG. 1B). As expected, 500 bp long dsRNA complexed with lipofectamine (but not without lipofectamine) induced similar STAT1 and STAT2 phosphorylating activity as obtained with the positive control recombinant IFN-β (FIG. 1B). These results demonstrated that two anti-TLR9 siRNA, TLR9.2 and TLR9.3, allow specific downregulation of TLR9 expression in HEK 293 cells, and that in this cell line, transfection with siRNA does not induce type I IFN as a non-target-specific effect.

Sequence Dependent Potent Induction of IFN-α by siRNA in Plasmacytoid Dendritic Cells Next we studied whether anti-TLR9 siRNA that inhibited TLR9 expression in HEK 293 cells desensitizes PDC for stimulation with a TLR9 ligand. Since the PDC is a major producer of type I IFN in the human immune system, the use of double-stranded (ds) RNA for selective target protein inhibition in PDC might be complicated by dsRNA-mediated non-target-specific type I IFN induction. To study this possibility, PDC from human peripheral blood were incubated with either poly(I:C), the prototype stimulus for dsRNA, or with a 500 basepairs (bp) long dsRNA molecule; both were complexed with lipofectamine for cytosolic delivery. The TLR9 ligand CpG-A ODN 2216 (Krug, A. et al. *Eur J Immunol* 31, 2154-63 (2001)) and the TLR7 ligand R848 served as positive controls. We found that both dsRNA molecules lacked the ability to induce IFN-α in PDC, while the positive controls CpG-A ODN 2216 and R848 showed a vigorous IFN-α response. These results suggested that dsRNA may be useful for selective knockdown of target genes in PDC.

Figure 2:
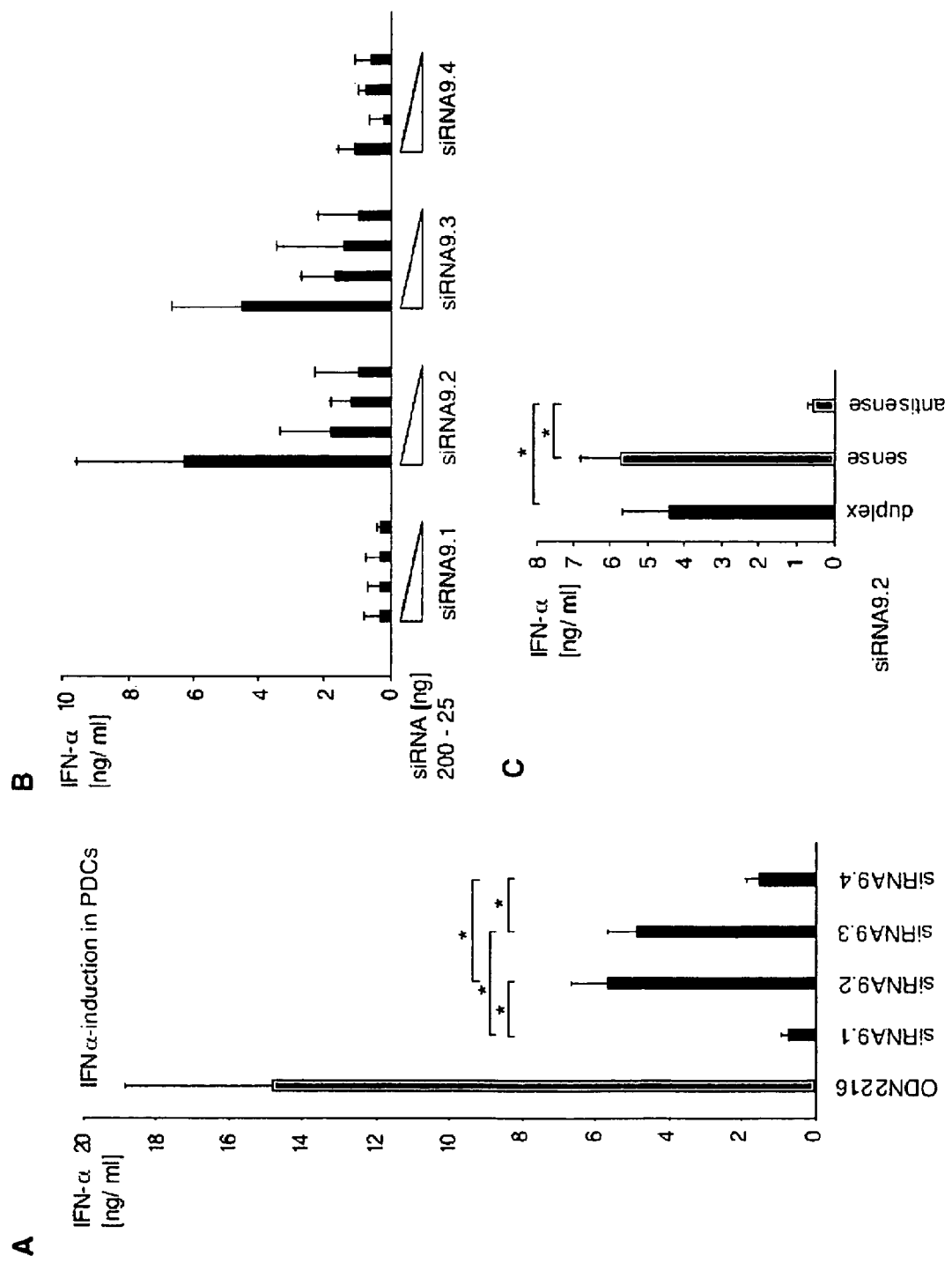
FIGS. 2A-2E: Sequence-dependent induction of IFN-α in plasmacytoid dendritic cells by siRNA is based on motif recognition on the single-strand level PDC (50.000/well) were transfected with different RNA oligonucleotides using lipofectamine (0.5 µl). After 36 hours, IFN-α production was measured in the supernatants.
Figure 2:
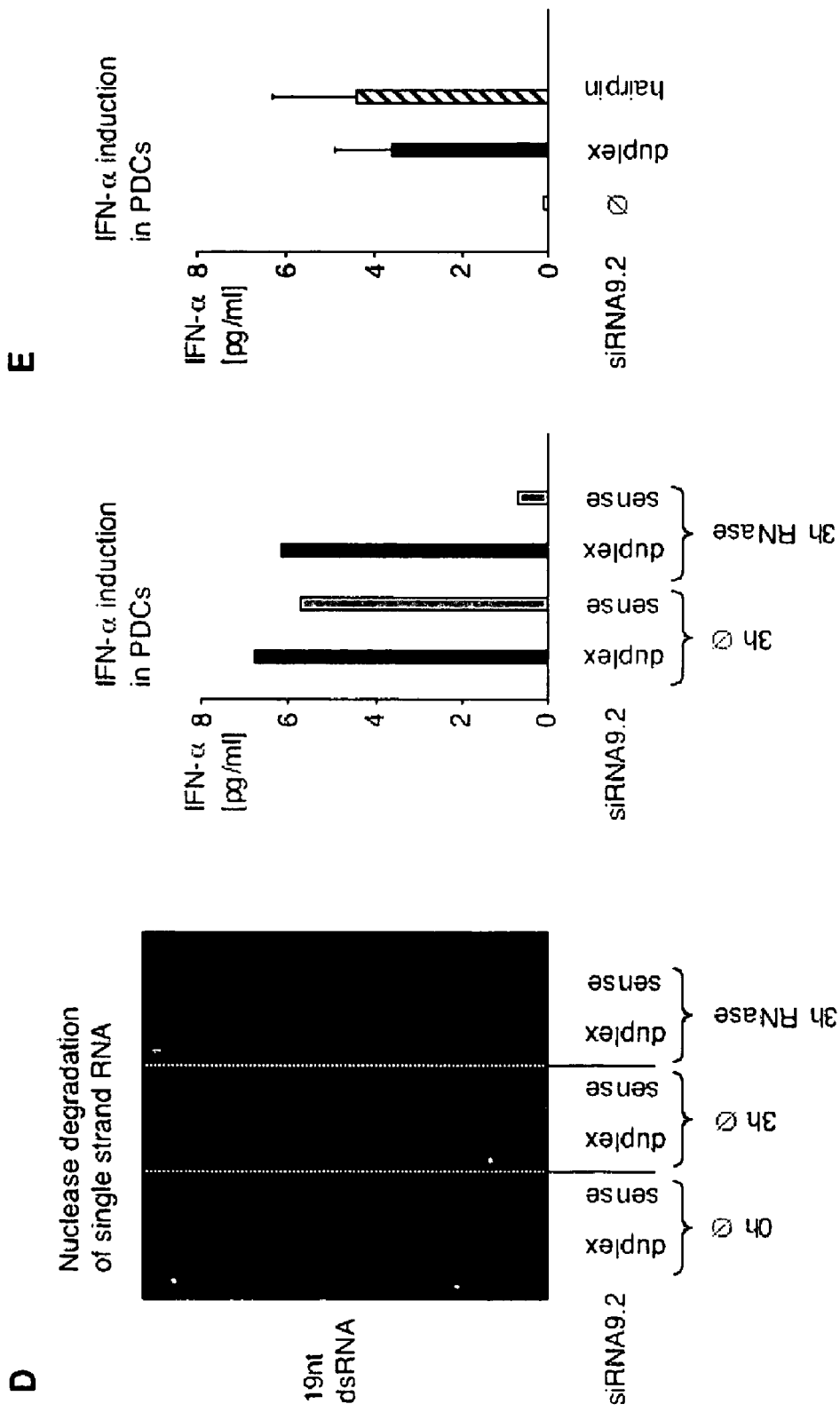

Surprisingly, transfection of the four anti-TLR9 siRNAs at 200 ng induced a consistent pattern of IFN-α production in PDC (FIG. 2A). TLR9.2 and TLR9.3 induced significantly more IFN-α production in PDC than TLR9.1 and TLR9.4 (FIG. 2A). To exclude that RNA degradation is responsible for the lower degree of interferon-induction by TLR9.1 and TLR9.4 (see FIG. 2A), we compared decreasing amounts of all four sequences. At 25 ng (12.5 nM) the two sequences TLR9.2 and TLR9.3 still induced higher levels of IFN-α than TLR9.1 at 200 ng (100 nM) (FIG. 2B), confirming the distinct activity of the four anti-TLR9 siRNA in inducing IFN-α in PDC. Distinct IFN-α inducing activity of TLR9.1 and TLR9.2 was also observed when siRNA was delivered into the cytosol of PDC by electroporation demonstrating that complex formation of siRNA with lipofectamine is not required for the IFN-α induction by siRNA; rather, the siRNA molecule itself seemed to be the active agent. No IFN-α induction by siRNA was observed in B cells or myeloid dendritic cells (data not shown).

Of note, among the four anti-TLR9 siRNAs tested, the two with the highest activity to downregulate TLR9 expression in HEK 293 cells were also the most potent sequences to induce IFN-α in PDC (compare FIG. 1A and FIG. 2A). Although unlikely, a target-specific effect (inhibition of TLR9) rather than non-target-specific immunostimulatory effect may be responsible for the IFN-α induction in PDC. To exclude this possibility we compared a panel of siRNAs targeting mRNA sequences that are expressed in PDC (TLR9) or not expressed in PDC (TLR2, TLR3, TLR4, see Table 1). Considerable differences in the potency of these siRNAs to induce IFN-α were seen, but no correlation was found between the potency to induce IFN-α and the presence or absence of the target mRNA in PDC (ODN 2216: x ADD VALUE±SEM; from low to high IFN-α induction: TLR4.1: 491±59; TLR9.1: 500±88; TLR9.4: 760±131; TLR4.2: 1208±267; TLR3.2: 1219±204; TLR2.1: 1535±235; TLR3.1: 2503±552; TLR9.3: 3592±283; TLR9.2: 4845±621: n=6). The possibility of differences in preparation quality or contaminants contributing to distinct IFN-α-inducing activity of siRNA was excluded by using siRNA sequences from different commercial sources that gave identical results (data not shown). These data indicated that IFN-α induction in PDC by siRNA is sequence-dependent and is not linked to the presence or absence of the target mRNA.

Identification of an IFN-α-Inducing RNA Sequence

It has been reported that guanosine- and uridine rich single-stranded RNA induces IFN-α in PDC. A mixture of guanosine and uridine monomers also showed immunostimulatory activity. Therefore we speculated that differences in the guanosine and uridine content of the siRNA in our study may be responsible for the different activity of siRNA to induce IFN-α in PDC. Since siRNA is double-stranded, the total content of guanosine and uridine in a 19mer siRNA is always 19. The number of uridines in the siRNAs tested ranged from 9 to 11 with no correlation between number of uridines and IFN-α inducing activity (see Table 1). Immunoactive siRNAs may still contain specific single strands (sense or anti-sense) with different guanosine- and uridine content. However, the total numbers of guanosines and uridines ranged between 7 and 12 in the single strands of the active siRNAs (TLR9.2 and TLR9.3) as well as in single strands of siRNAs with lower activity (TLR9.1, TLR9.4, TLR2.1, TLR4.1, TLR4.2, TLR3.1, TLR3.2); furthermore, the ratio of uridines to guanosines was not linked to the immunological activity (see Table 1). Therefore, a specific sequence rather than simply the content of guanosines and uridines seemed to be responsible for the immunological activity of TLR9.2 and TLR9.3.

In order to identify the immunostimulatory sequence, we compared the IFN-α inducing activity of the two single strands (sense and antisense) of TLR9.2 with the activity of the duplex. The sense strand of TLR9.2 was equally potent to induce IFN-α in PDC than the duplex, while the antisense strand of TLR9.2 showed only weak activity (FIG. 2C, left panel). IFN-α induction by poly(U) or by poly(A) ssRNA and by poly(U:A) dsRNA was low as compared to the sense strand of TLR9.2 siRNA (RNA9.2s: 4962±797; poly(U): 574±165; poly(A): 244±120; poly(U:A): 111±53; n=7; for poly(A) also see FIG. 3B second bar from left) further supporting the concept that the sense strand of TLR9.2 contains a specific immunostimulatory motif that is recognized by PDC.

Since siRNA is generated by annealing of the sense and the antisense strand, the immunostimulatory activity of TLR9.2 siRNA may be due to unbound sense strand in the siRNA preparation and not due to the duplex. To exclude this possibility, the sense strand and the duplex of TLR9.2 were exposed to single-strand RNAse. As expected, the sense strand was completely degraded by RNAse treatment (FIG. 2D, left panel), leading to the loss of immunological activity (FIG. 2D, right panel). In contrast, the duplex was not affected by RNAse treatment, and the activity to induce IFN-α was maintained (FIG. 2D). To further exclude a contribution of contaminating single-stranded RNA in the siRNA preparation we designed a single-stranded RNA that forms an energetically stable hairpin (similar to microRNA) in which the double-stranded region contains the complete duplex of TLR9.2 siRNA (Table 2). This hairpin was found to be as active in inducing IFN-α as the TLR9.2 siRNA duplex (FIG. 2E). These data demonstrated that immunostimulatory activity of siRNA cannot be prevented by eliminating single-stranded contaminants in siRNA preparations, and that immunostimulation is also relevant for the hairpin-based RNA interference (ie. microRNA).

Figure 3:
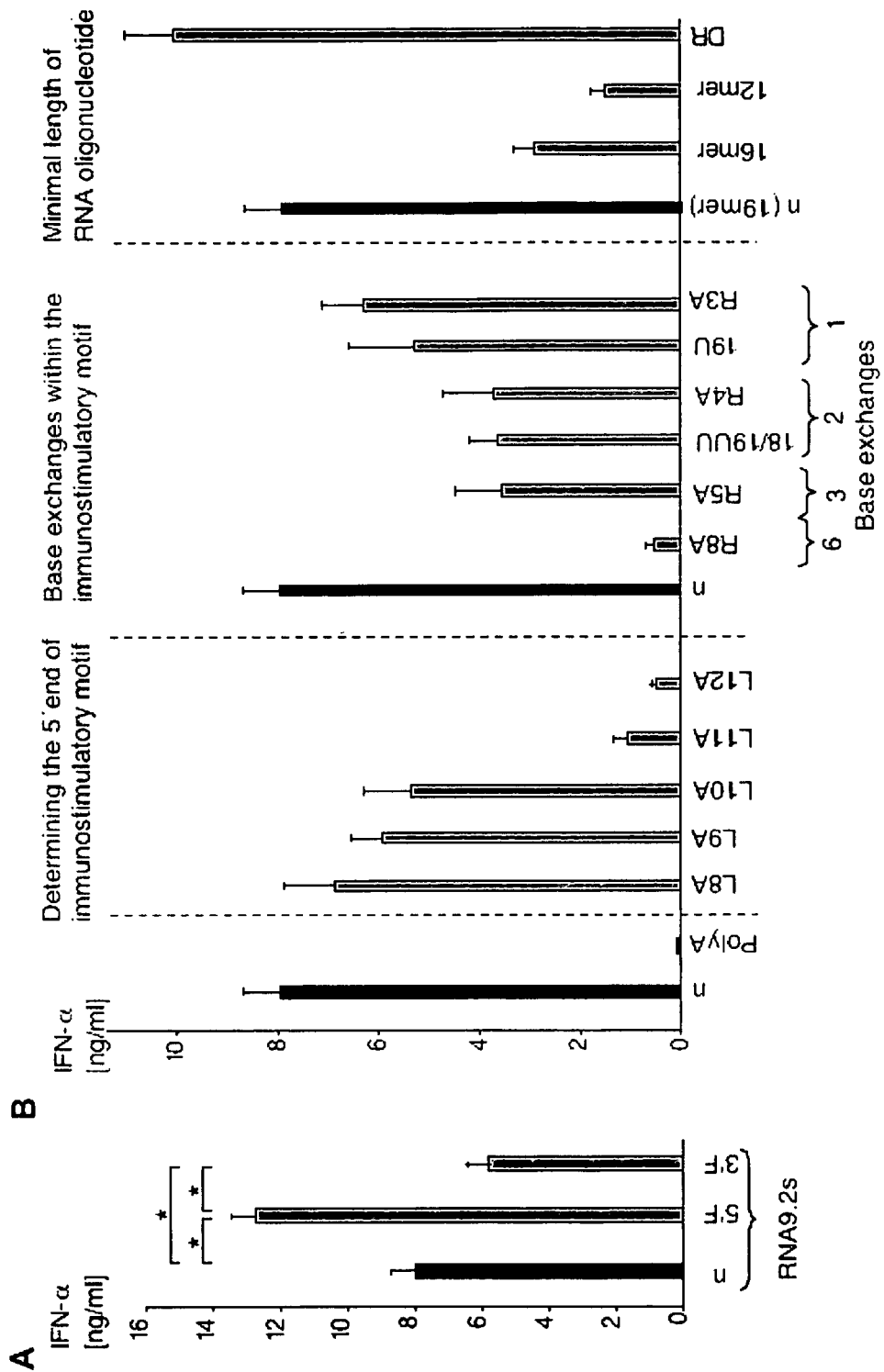
FIGS. 3A-3B: A sequence of 9 bases at the 3'end of the RNA9.2 sense strand is responsible for the immunostimulatory activity PDC were transfected with different RNA oligonucleotides. After 36 hours, IFN-α production was measured in the supernatant.

The sequences of TLR9.2 and TLR9.3 show an overlap of 13 bases (see Table 1). Since both siRNAs were potent inducers of IFN-α in PDC, we hypothesized that the sequence motif responsible for IFNα induction is located in the overlapping region of TLR9.2 and TLR9.3. Thus localization of the immunostimulatory motif pointed to the 13 bases at the 3'end of the sense strand of TLR9.2. This assumption was supported by decreased activity of the sense strand when a FITC molecule was linked to the 3'end but not the 5'end (FIG. 3A, compare 5° F. to 3° F.). The lack of immunological activity of poly(A) (FIG. 3A) allowed us to substitute bases in the sense strand of TLR9.2 with A in order to narrow the motif. Consistent with a localization of the immunostimulatory motif within the 13 bases of the 3'end of the sense strand of TLR9.2, substitution of 8 bases at the 3'end (R8A, R stands for right) but not at the 5'end (L8A, L stands for left) abolished the immunological activity of the sense strand (FIG. 3B). By further increasing the number of A from the 5'end (L8A to L12A), position 11 was identified to be essential for the motif at the 3'end, suggesting that the 9 bases at the 3'end (5'GUC-CUUCAA 3', SEQ ID NO:1) of the sense strand of TLR9.2 are responsible for its immunostimulatory activity. The exchange of increasing numbers of bases in this 9mer sequence resulted in a gradually decreasing immunological activity of the sense strand of TLR9.2 with a complete loss of activity when 6 bases were exchanged within the 9mer sequence (FIG. 3B; R8A). The minimal length of the RNA required for IFNα induction was found to be in the range of 19 bases, since both a 12mer and a 16mer containing the 9mer sequence showed a much lower activity (FIG. 3B). On the other hand, by placing the 9mer sequence twice in a 19mer RNA oligonucleotide (termed DR), the immunological activity was further increased as compared to the sense strand of TLR9.2, which only contains one immunostimulatory 9mer sequence (termed n; FIG. 3B).

Dissection of Immunostimulatory Activity and Silencing Activity of siRNA

Figure 4:
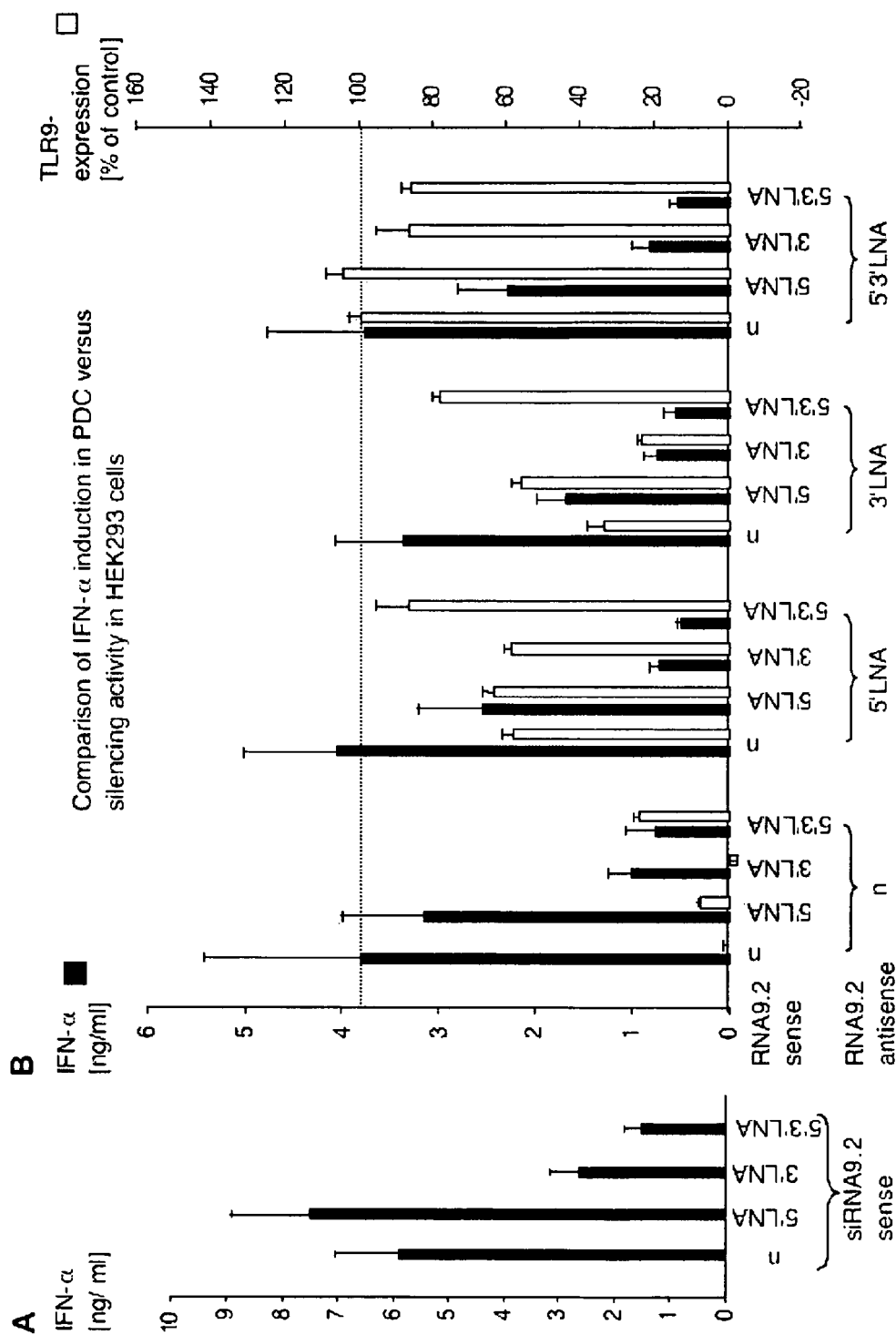
FIGS. 4A-4B: LNA-modifications of the sense and the anti-sense strand in siRNA TLR9.2 reveal IFN-α induction and silencing as two independent activities of siRNA PDC were transfected with different RNA oligonucleotides. After 36 hours, IFN-α production was measured in the supernatant.

According to the above studies, the immunostimulatory activity of TLR9.2 is localized in the sense strand and the silencing activity in the anti-sense strand of the duplex. Appropriate modifications of both single RNA strands of TLR9.2 may allow dissection of the immunostimulatory from the silencing activity and vice versa. The backbone modification, locked nucleic acids (LNA), has been used to change the properties of siRNA with regard to target inhibition. We were interested whether LNA modification of the sense and the anti-sense strand can be used to modulate not only the silencing but also the immunological activity of siRNA. First we examined the impact of 5' and 3' LNA on the immunological activity of the sense strand of TLR9.2 (see Table 2). Consistent with linking a FITC molecule to the 5' or the 3' end (see FIG. 3A), LNA modification at the 3' end but not at the 5'end strongly inhibited the activity of the sense strand to induce IFNα (FIG. 4A). Next, sense and anti-sense strand with different LNA modifications (LNA at 5'end, at 3'end, or at both 5' and 3' ends) or without LNA modification were annealed to generate a total of 16 different TLR9.2 siRNA derivatives. We assessed the activity of this panel of TLR9.2 duplexes to induce IFNα in PDC (FIG. 4B, black bars). Like for the sense strand alone (FIG. 4A), duplexes with LNA modification of the sense strand at the 3'end or at both the 3'end the 5'end strongly inhibited IFNα inducing activity, while LNA modification at the 5'end sense strand showed no major changes of the activity (FIG. 4B). LNA modifications of the anti-sense strand did not influence the immunostimulatory activity of an siRNA containing an unmodified sense strand (FIG. 4B).

Next we examined the influence of LNA-modifications on the silencing activity of TLR9.2 siRNA. Unlike for IFNα induction, LNA modification of the sense strand had almost no effect on the silencing activity of TLR9.2 siRNA (FIG. 4B, open bars). In contrast, LNA modification of the anti-sense strand strongly affected the silencing activity of the TLR9.2 siRNA. LNA modification of the 3'end of the anti-sense strand had less impact on the silencing activity than LNA modification of the 5'end of the anti-sense strand. Silencing activity was completely lost when both the 3' and the 5' ends were modified by LNA. Together these data indicated that it is possible to dissociate the two functional activities of siRNA by introducing LNA modifications to different regions of the sense and the anti-sense strand: the silencing activity can be maintained while minimizing the immunostimulatory component of siRNA (for example: LNA at the 3'end of the sense strand); the immunostimulatory activity can be maintained while abolishing the silencing activity of siRNA (i.e. LNA at the 3' and the 5'end of the anti-sense strand).

Immunostimulatory siRNA Induces Systemic Immune Responses in Mice In Vivo

Figure 5:
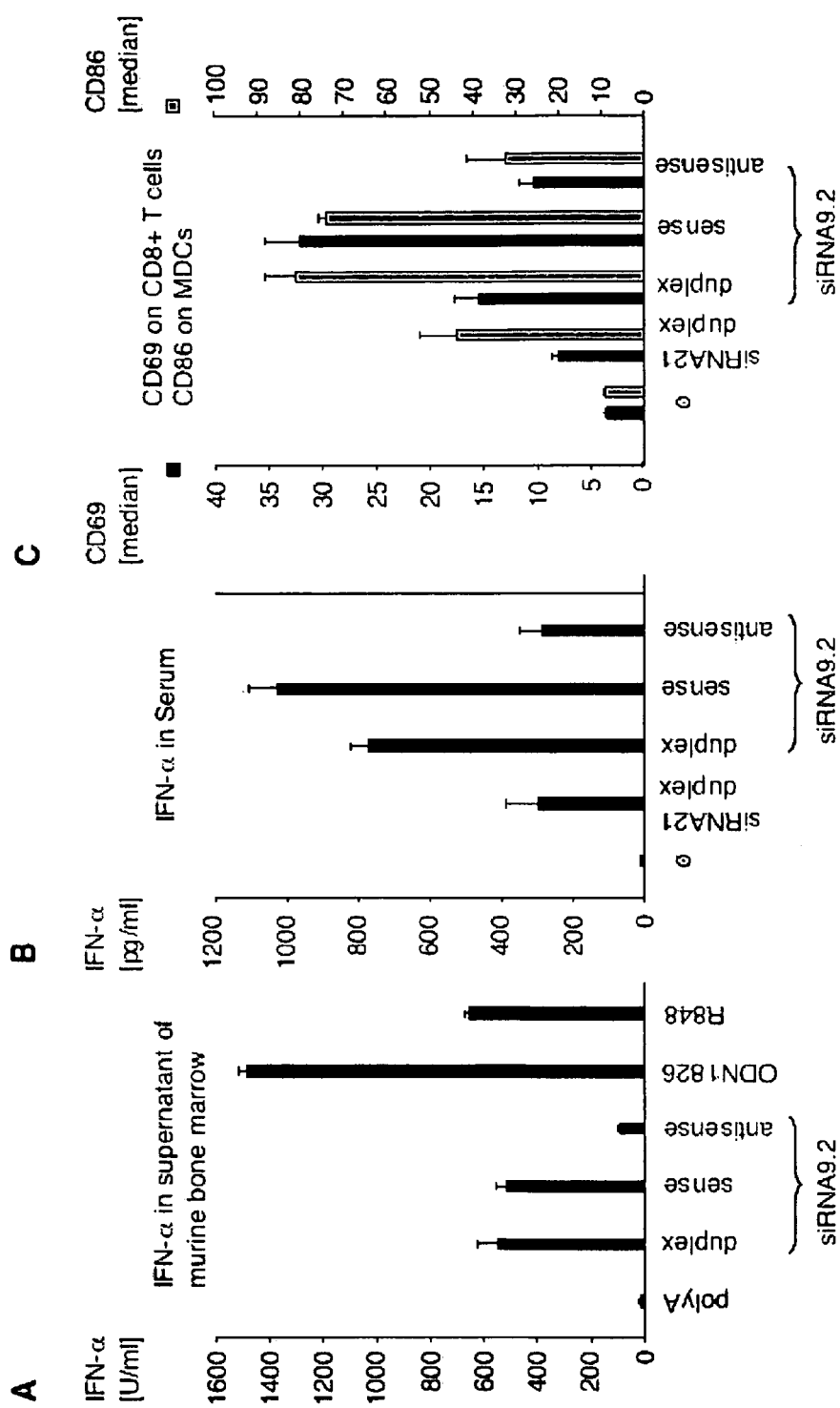
FIGS. 5A-5D: Sequence dependent induction of systemic immune responses by siRNA in mice in vivo.
Figure 5:
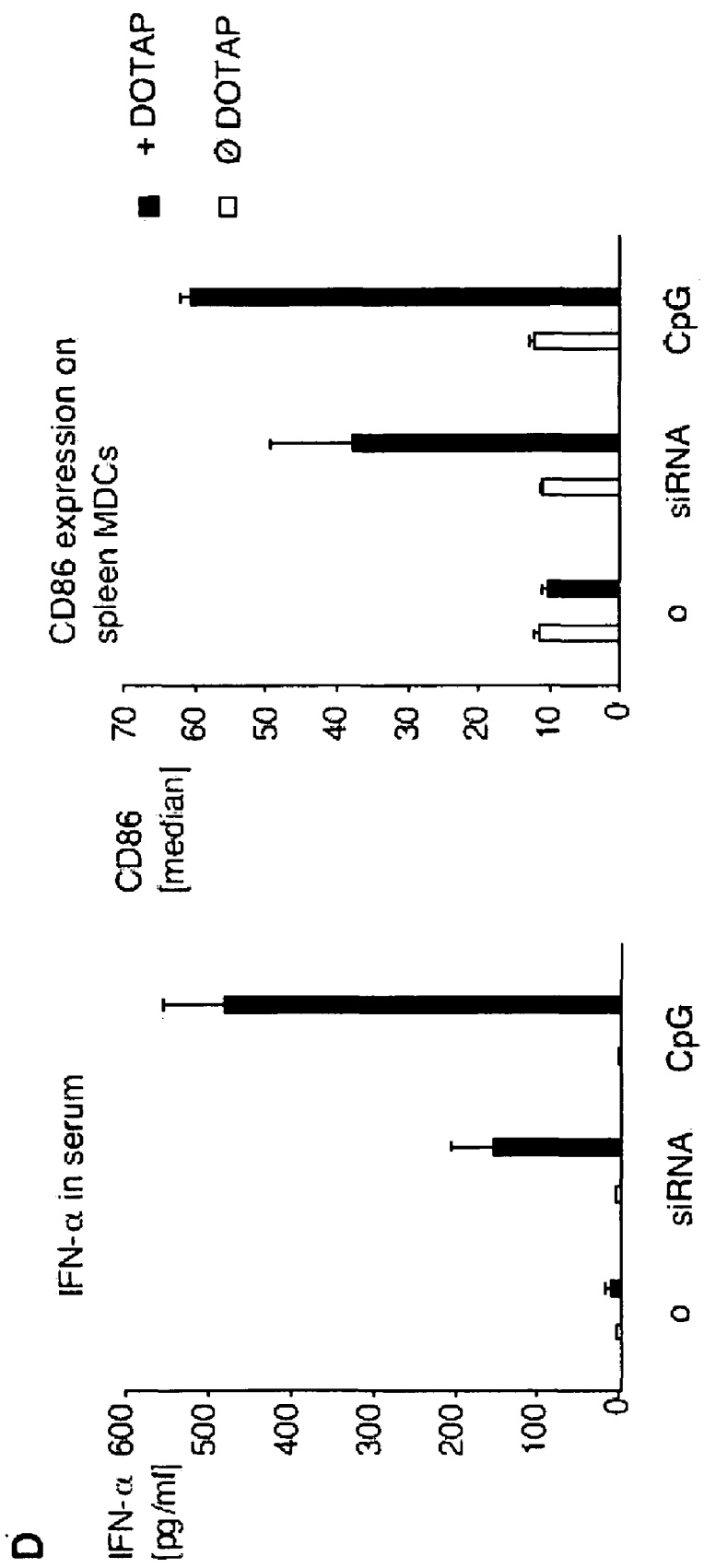

In order to study the systemic activity of siRNA in vivo, we first examined the in vitro immunostimulatory activity of siRNA sequences in the murine system. Similar to the human system, the TLR9.2 duplex and the sense strand were found to induce IFNα, while the anti-sense strand of TLR9.2 was much less active, and poly(A) was inactive (FIG. 5A).

Next, the immunological activity of the TLR9.2 duplex, the TLR9.2 sense strand, and the TLR9.2 anti-sense strand was assessed in vivo. TLR2.1 was included in this analysis as a siRNA that in the human system was less active than TLR9.2. Seven hours after i.v. injection into 129Sv mice, the concentration of IFN-α was measured in the serum of mice (FIG. 5B). In addition, activation of immune cell subsets in the spleen was assessed by flow cytometry after 43 hours (FIG. 5C). Consistent with the in vitro data, the TLR9.2 duplex and the TLR9.2 sense strand showed the highest activity to induce systemic levels of IFN-α and to activate CD4 and CD8 T cells and myeloid dendritic cells (FIG. 5C). No immunological activity was observed with either cationic liposomes (DOTAP) or siRNA alone. (FIG. 5D). Together, these results demonstrated that administration of siRNA in vivo elicits systemic immune responses detectable in both blood and spleen and that the immunological activity in mice shows similar sequence dependency as in the human system.

Immune Recognition of siRNA Requires TLR7

Figure 6:
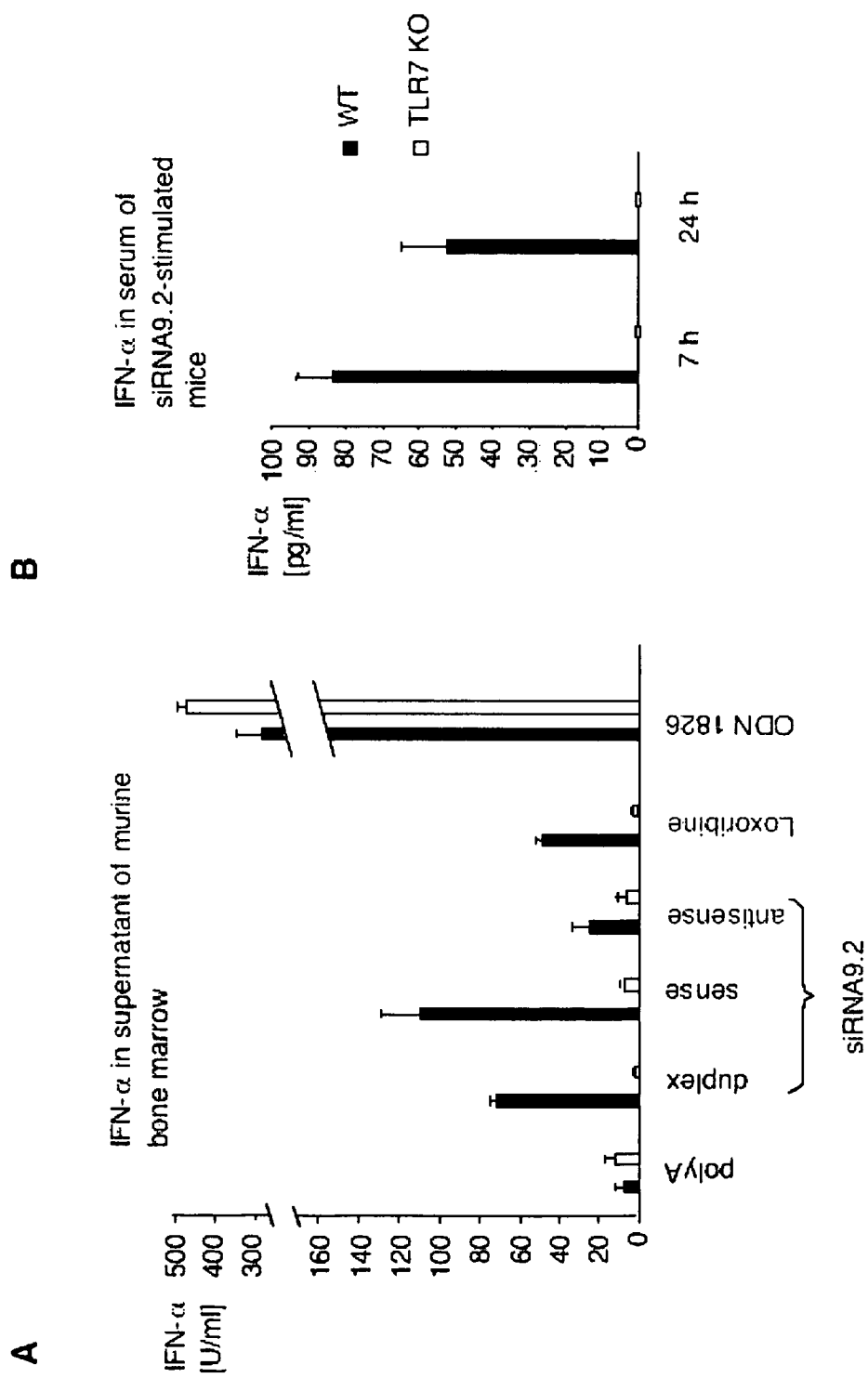
FIGS. 6A-6C: TLR7 is required for siRNA recognition
Figure 6:
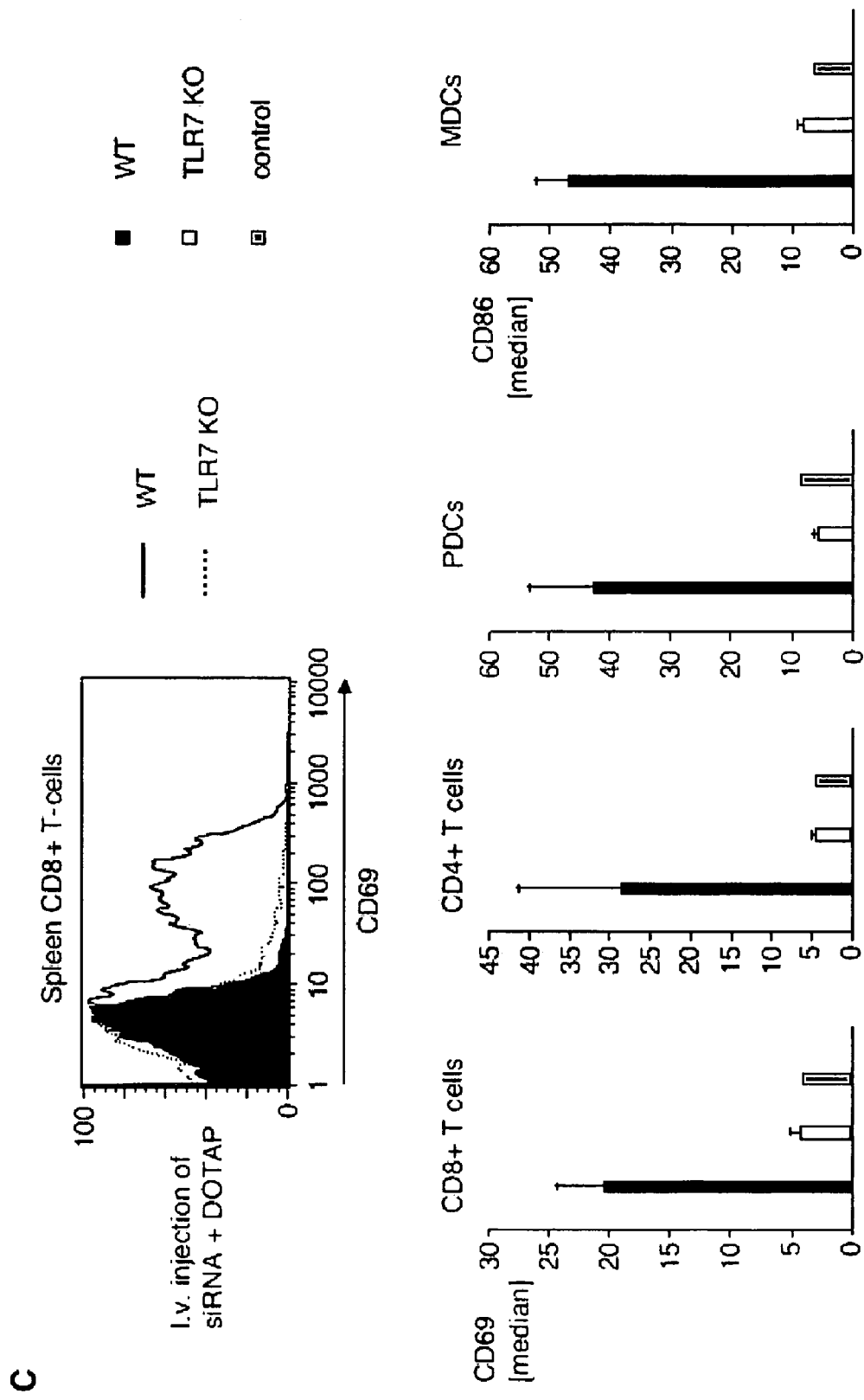

Conserved sequence dependent immune recognition of siRNA in mice and humans allowed the use of knockout mice in order to identify the responsible receptor. TLR7 and TLR9 are the only members of the TLR family that are expressed in PDC FIX REFERENCE {Krug, 2001 #5; Hornung, 2002 #37} and that are known to be linked to IFN-α production. So far, RNA sequence motifs specifically detected via TLR7 have not been identified. We hypothesized that TLR7 is involved in the recognition of the immunostimulatory sequence motif contained in TLR9.2 siRNA. Indeed we found that IFN-α induction in vitro by the TLR9.2 duplex and the TLR9.2 sense strand as well as by an established TLR7 ligand (loxoribine) was absent in bone marrow cells derived from TLR7-deficient mice (FIG. 6A). In contrast, IFN-α induction by the TLR9 ligand CpG ODN 1826 was not reduced in bone marrow cells derived from TLR7-deficient mice (FIG. 6A).

Additional in vivo mechanisms of immune recognition of siRNA might exist that are not detectable in vitro. As such, TLR9.2 siRNA was injected i.v. into TLR7-deficient mice and wild type control mice. In contrast to wild type mice, TLR7-deficient mice had no detectable IFN-α in serum after 7 h and 24 h (FIG. 6B). Furthermore, no activation of CD4 T cells, CD8 T cells, myeloid dendritic cells and PDC was found in spleen cells of TLR7-deficient mice, while strong activation of all four cell subsets was observed in wild type mice (FIG. 6C). Together these data indicated that TLR7 is required for immune recognition of TLR9.2 siRNA.

Discussion

One of the most significant advances in RNA interference technology was the observation that by reducing the length of the dsRNA molecules down to 22 bp, PKR-mediated nonspecific type I IFN induction can be abolished while sequence-specific downregulation of the target mRNA is maintained. In agreement with this concept we were able to establish siRNA-mediated sequence-specific downregulation of TLR9 in the human HEK293 cell line in the absence of an IFN response. However, when we attempted to apply this method to primary plasmacytoid dendritic cells (PDC) we made the surprising observation that the previously proposed length dependence of dsRNA recognition seemed to be reversed: while transfection of PDC with a 500 bp long dsRNA molecule or with poly(I:C) (mimicking long dsRNA) failed to induce IFN-α, some of the siRNA sequences tested showed a vigorous IFN-α response.

Based on the overlapping sequence of two siRNAs with potent IFN-α inducing activity we were able to identify an immunostimulatory single-stranded RNA sequence consisting of 9 bases (5'GUCCUUCAA 3', SEQ ID NO:1). By chemical backbone modification of different regions of both strands of the immunostimulatory siRNA, we were able to dissect immunostimulation and RNA silencing as two independent functional activities. The same type of sequence-specificity with regard to IFN-α induction by siRNA was seen in the mouse. In vitro immunostimulatory activity and in vivo systemic immune responses were abrogated in TLR7-deficient mice, demonstrating that sequence-specific immune recognition of siRNA is mediated via TLR7.

Our results provide evidence that the immunostimulatory activity of siRNA is not mediated by single-stranded RNA molecules left over in the siRNA preparation after an incomplete annealing process: i) treatment of the siRNA preparation with single-strand RNAse did not affect the immunological activity of siRNA, while the activity of the corresponding immunostimulatory single-strand RNA was abolished; ii) a single-strand RNA oligonucleotide designed to spontaneously form an energetically stable hairpin (in the form of microRNA) containing the complete duplex of the immunostimulatory siRNA was as active as the immunostimulatory siRNA. These data confirmed that recognition mechanisms responsible for the recognition of siRNA allow the detection of a single-strand RNA motif within the RNA duplex.

It is interesting to note that for the recognition of siRNA and the TLR9 ligand (CpG DNA), the detection of the immunostimulatory sequence motifs occurs on the single-strand level although both siRNA and microbial DNA are primarily double-stranded (viral or bacterial DNA genomes are usually double-strand). To date there is no information whether helicase activity is part of the recognition process. For both RNA and DNA, synthetic single-stranded oligonucleotides containing the appropriate sequence motifs can be used to elicit the corresponding type of immune responses. The minimal length of an immunostimulatory RNA oligonucleotide was approximately 19 bases. Similarly, the 6mer CpG motif needed to be part of a longer oligonucleotide to become an active TLR9 ligand (Hartmann, G. et al. *J Immunol* 2000, 164:944-53). Since poly A RNA showed no immunological activity, the addition of poly A could be used for elongation of an RNA oligonucleotide containing the 9mer stimulatory sequence up to the length of a 19mer. The insertion of two stimulatory 9mer sequences in a 19mer RNA oligonucleotide further increased the immunostimulatory activity. By analogy, poly(C) was used in previous studies for elongation of a CpG motif containing oligodesoxynucleotide, since poly(C) DNA (with and without phosphorothioate modification) lacked immunostimulatory activity (Hartmann, G. et al. *J Immunol* 2000, 164:944-53).

It has been reported that certain single-stranded RNA viruses such as vesicular stomatitis virus and influenza virus are recognized by immune cells via TLR7 (Lund, et al., Proc. Natl. Acad. Sci. USA 2004, 101:5598-603; Heil et al., Science 2004, 303:1526-9; Diebold, et al., Science 2004, 303: 1526-9), but specific sequence motifs responsible for viral RNA recognition have not been identified so far. Instead, poly(U) has been reported to be active, and it has been proposed that GU-rich sequences in viral RNA are responsible for immune recognition; furthermore, that a mixture of monomeric Gs and Us is immunostimulatory, indicating that RNA degradation products might be involved. There are several lines of evidence that the immunostimulatory activity of the RNA molecules in our study is not due to GU content. First, the total number of G and U of duplex RNA by definition is always identical with the length of the duplex (i.e. the GU count of a 19mer duplex is always 19). Second, a higher number of Gs or Us or the ratio of G to U in the one or the other of the two single strands of siRNA was not associated with the immunological activity of siRNA. Third, increasing the number of G in the immunostimulatory single strand RNA reduced rather than enhanced its immunological activity; and fourth, poly(U) was weak compared to the RNA oligonucleotide containing the immunostimulatory RNA sequence described in this study.

Although our results clearly demonstrate that immune recognition of siRNA by PDC is sequence-dependent and GU content-independent, the sequence described in this study may only be one of several different immunostimulatory RNA sequence motifs. Optimization of the sequence of this study and the identification of additional sequences will be the subject of a broader screen of sequences to identify the most potent immunostimulatory RNA motifs.

At least for the RNA sequence described in this study, recognition of siRNA seems to be conserved in mouse and man. Upon intravenous injection of immunostimulatory siRNA complexed with DOTAP we observed strong systemic immune responses including IFN-α in the serum and activation of T cells, PDC and myeloid dendritic cells. The level of immune activation was in the same range as with the TLR9 ligand CpG. Activation of myeloid dendritic cells and T cells by siRNA in vivo may be due to secondary effects mediated by IFN-α as has been demonstrated in the human system (Krug, A. et al. *J Immunol* 170, 3468-77 (2003), Rothenfusser, S. et al. *Blood* 103, 2162-9 (2004), Rothenfusser, S. et al. *Eur J Immunol* 31, 3525-34 (2001)). As a consequence cationic lipid-complexed siRNA, similar to CpG, may elicit potent therapeutic activity against viral (Dittmer, U. & Olbrich, A. R. *Curr Opin Microbiol* 6, 472-7 (2003)) and bacterial infection (Wagner, H., *Springer Semin Immunopathol* 22, 147-52 (2000)) and tumors (Heckelsmiller, K. et al. *Eur J Immunol* 32, 3235-45 (2002), Heckelsmiller, K. et al. *J Immunol* 169, 3892-9 (2002), Weiner, G. J. *Curr Top Microbiol Immunol* 247, 157-70 (2000)). It is interesting to note that siRNA was successfully used to inhibit viral replication and transcription in a murine model of hepatitis B (Klein, C. et al. *Gastroenterology* 125, 9-18 (2003), Davidson, B. L. *N Engl J Med* 349, 2357-9 (2003)). Since IFN-α is a mainstay of hepatitis B treatment, PDC-derived IFN-α might have contributed to therapeutic effects of siRNA.

In our study, immune responses induced by siRNA both in vitro and in vivo completely depended on the presence of TLR7. However, in many cell lines, such as HEK293 cells, TLR7 is not expressed and thus immune recognition of siRNA via TLR7 is not expected. This is consistent with our in vitro observation that the supernatant of siRNA-transfected HEK293 cells, in contrast to transfection with long dsRNA molecules, shows no type I IFN response as evidenced by the lack of STAT1- or STAT2-phosphorylating activity. These results are in agreement with the concept, that in TLR7-deficient cell lines in vitro, short dsRNA of 21 bp (siRNA) lack immunostimulatory activity and are useful for sequence-specific downregulation of target genes.

Contradicting this concept is a report suggesting that transfection of siRNAs into cell lines results in PKR-dependent type I IFN-mediated activation of the STAT pathway and leads to upregulation of IFN-stimulated genes (Sledz, C. A., et al. *Nat Cell Biol* 5, 834-9 (2003)). Furthermore, siRNA was reported to induce type I IFN responses via TLR3 expressed in cell lines, including HEK293 cells (Kariko, K., et al. *J Immunol* 172, 6545-9 (2004), Kariko, K. et al. *Cells Tissues Organs* 177, 132-8 (2004)). However, the complete loss of immunostimulatory activity of siRNA in TLR7-deficient mice in our study provides evidence that PKR and TLR3 do not represent the major mechanisms by which siRNA is detected by the innate immune system. This is supported by our recent finding that the immunological activity of siRNA is not affected in TRIF-deficient mice (data not shown). TRIF is a necessary adaptor molecule for TLR3 signaling. The lack of immunological activity of siRNA in TRIF-deficient mice also indicates that the alternative TLR3- and TRIF-independent pathway of long double-stranded RNA (poly[I:C]) recognition proposed by Hoebe and colleagues Hoebe, K. et al. *Nat Immunol* 4, 1223-9 (2003). is not involved in the immune recognition of siRNA.

Non-target-specific downregulation of protein expression by siRNA-induced type I IFN production is a major issue in RNA interference technology. Ways to separate type I IFN inducing properties from the silencing activity of siRNA will advance the application of siRNA. In our study, the siRNA TLR9.2 turned out to be an excellent model to demonstrate that silencing activity and immunostimulatory activity are two unrelated functional properties of siRNA. Dissection of both functional activities was possible since the RNA sequence responsible for IFN-α induction was found to be located on the sense strand and not the anti-sense strand. By selected backbone modification (with locked nucleic acid; LNA) of certain regions on the sense or the antisense strand of siRNA TLR9.2, we were able to generate derivatives of siRNA TLR9.2 in which the immunostimulatory activity was abolished while the silencing activity was maintained, and vice versa. This demonstrated that the functional properties of siRNA can be changed to favor immunostimulation and/or target mRNA silencing. Obviously, in addition to their effects on mRNA silencing, certain siRNA can also have added therapeutic potential due to their potential immunostimulatory properties, especially as it relates to use as an anti-infective or anti-tumor therapeutic. The stimulatory sequence used in this study resulted in IFN-α induction that was approximately 30% of the maximal stimulation seen in PDC (stimulus: CpG-A ODN 2216). Although it is unlikely that this stimulatory sequence is optimal, our results with this RNA sequence in vivo highlight the potential for further development of immunostimulatory siRNA molecules.

Example 2

Synthesis of Modified Oligonucleotides for Modulating Immunostimulation (a) RNA, 2'-O-methyl-modified, 2'-deoxy-2'-fluoro-modified, and thioate-modified oligonucleotides The RNA molecules were synthesized on a 394 ABI machine using the standard cycle written by the manufacturer with modifications to a few wait steps as described below. The solid support was controlled pore glass (CPG; 500 Å, Prime Synthesis, Inc., Aston, Pa., USA). The monomers were RNA phosphoramidites or 2'-O-Methyl (2'-OMe) RNA phosphoramidites with standard protecting groups obtained from Pierce Nucleic Acid Technologies (Pierce Milwaukee LLC, Milwaukee, Wis., USA) used at concentrations of 0.15 M in $CH_3CN$ unless otherwise stated. Specifically the RNA phosphoramidites were 5'-O-dimethoxytrityl-$N^6$-benzoyl-2'-O-tbutyldimethylsilyl-adenosine-3'-O-(β-cyanoethyl-N,N'-diisopropyl)phosphoramidite, 5'-O-dimethoxytrityl-$N^2$-isobutyryl-2'-O-tbutyldimethylsilyl-guanosine-3'-O-(β-cyanoethyl-N,N'-diisopropyl) phosphoramidite, 5'-O-dimethoxytrityl-$N^4$-acetyl-2'-O-tbutyldimethylsilyl-cytidine-3'-O-(β-cyanoethyl-N,N'-diisopropyl) phosphoramidite, 5'-O-dimethoxytrityl-2'-O-tbutyldimethylsilyl-uridine-3'-O-(β-cyanoethyl-N,N'-diisopropyl)phosphoramidite, 5'-O-dimethoxytrityl-$N^6$-benzoyl-2'-O-methyl-adenosine-3'-O-(β-cyanoethyl-N,N'-diisopropyl)phosphoramidite, 5'-O-dimethoxytrityl-$N^2$-isobutyryl-2'-O-methyl-guanosine-3'-O-(β-cyanoethyl-N,N'-diisopropyl)phosphoramidite, 5'-O-dimethoxytrityl-$N^4$-acetyl-2'-O— methyl-cytidine-3'-O-(β-cyanoethyl-N,N'-diisopropyl) phosphoramidite, and 5'-O-dimethoxytrityl-2'-O-methyl-uridine-3'-O-(β-cyanoethyl-N,N'-diisopropyl) phosphoramidite. The 2'-deoxy-2'-fluoro (2'-F) phosphoramidites, 5'-O-dimethoxytrityl-N-4-acetyl-2'-deoxy-2'-fluoro-cytidine-3'-O-N,N'-diisopropyl-2-cyanoethyl-phosphoramidite and 5'-O-dimethoxytrityl-2'-deoxy-2'-fluoro-uridine-3'-O-N,N'-diisopropyl-2-cyanoethyl-phosphoramidite were obtained from Promega Corp. (Madison, Wis., USA). 5'-O-dimethoxytrityl-N6-benzoyl-2'-deoxy-2'-fluoro-adenosine-3'-O-N,N'-diisopropyl-2-cyano-ethyl-phosphoramidite and 5'-O-dimethoxytrityl-N-2-isobutyryl-2'-deoxy-2'-fluoro-guanosine-3'-O-N,N'-diisopropyl-2-cyanoethyl-phosphoramidite were synthesized according to literature protocols (citations?). The coupling times were 10 min for all monomers. Details of the other reagents are as follows: activator, 5-ethyl thiotetrazole (0.25 M, Glen Research, Sterling, VI, USA); Cap A, 5% acetic anhydride/THF/pyridine (Glen Research, Sterling, VI, USA); Cap B: 10% N-methylimidazole/THF (Glen Research, Sterling, VI, USA); PO oxidation involved 0.02 M $I_2$/THF/$H_2O$ (Glen Research, Sterling, VI, USA). For the PS-oxidation a solution of the Beaucage reagent (Chruachem Ltd, Glasgow, UK) in acetonitrile (1%) was used. The trityl group was removed on the synthesizer with 3% TCA/dichloromethane (Glen Research, Sterling, VI, USA).

(b) Synthesis of Oligonucleotides with LNA linkages

The RNA molecules were synthesized on a 394 ABI machine using the standard cycle written by the manufacturer with modifications to a few wait steps as described below. The solid support was rA CPG (2 μmole, 520 Å, Prime Synthesis, Inc., Aston, Pa., USA, batch #CPG60N11RASN), rU CPG (G311103 is this a Prime Synthesis, Inc., Aston, Pa., USA batch number as well?), LocA (2 μmole, Proligo LLC, Boulder, Colo., USA, 40.0 μmoles/g, batch #225401), or LocT (2 μmole, Proligo LLC, Boulder, Colo., USA, 39.0 μmoles/g, batch #224597). Loc designates an LNA building block. The monomers were either RNA phosphoramidites (Pierce Nucleic Acid Technologies, Pierce Milwaukee LLC, Milwaukee, Wis., USA) or LNA phosphoramidites Loc$A^{Bz}$ (Proligo LLC, Boulder, Colo., USA, cat. no. 223917), $^{5'DMT}_{CE}$Loc$^{5me}C^{Bz}$ (Proligo LLC, Boulder, Colo., USA, cat. no. 223816), $^{5'DMT}_{CE}$Loc$^{5me}G^{iBu}$ (Proligo LLC, Boulder, Colo., USA, cat. no. 223817), $^{5'DMT}_{CE}$LocT (Proligo LLC, Boulder, Colo., USA, cat. no. 22818). All had standard protecting groups and were used at concentrations of 0.15 M in $CH_3CN$ unless otherwise stated. Specifically the RNA phosphoramidites were 5'-O-dimethoxytrityl-$N^6$-benzoyl-2'-O-tbutyldimethylsilyl-adenosine-3'-O-(β-cyanoethyl-N,N'-diisopropyl) phosphoramidite (batch #FG0082), 5'-O-dimethoxytrityl-$N^2$-isobutyryl-2'-O-tbutyldimethylsilyl-guanosine-3'-O-(β-cyanoethyl-N,N'-diisopropyl)phosphoramidite (batch #FE0031), 5'-O-dimethoxytrityl-$N^4$-acetyl-2'-O-tbutyldimethylsilyl-cytidine-3'-O-(β-cyanoethyl-N,N'-diisopropyl) phosphoramidite (batch #FF0046), and 5'-O-dimethoxytrityl-2'-O-tbutyldimethylsilyl-uridine-3'-O-(β-cyanoethyl-N,N'-diisopropyl) phosphoramidite (batch #FF0036). The LNA phosphoramidites were 5'-O-dimethoxytrityl-$N^6$-benzoyl-adenosine-3'-O-(β-cyanoethyl-N,N'-diisopropyl) LNA phosphoramidite, 5'-O-dimethoxytrityl-$N^2$-isobutyryl-guanosine-3'-O-(β-cyanoethyl-N,N'-diisopropyl) LNA phosphoramidite, 5'-O-dimethoxytrityl-$N^4$-acetyl-5-methyl-cytidine-3'-O-(β-cyanoethyl-N,N'-diisopropyl) LNA phosphoramidite, and 5'-O-dimethoxytrityl-5-methyl-thymidine-3'-O-(β-cyanoethyl-N,N'-diisopropyl) LNA phosphoramidite.

The coupling times were 10 mins for all monomers. Details of the other reagents are as follows: activator: 5-ethyl thiotetrazole (0.25 M, Glen Research, Sterling, VI, USA); Cap A, 5% acetic anhydride/THF/pyridine (Glen Research, Sterling, VI, USA); & Cap B, 10% N-methylimidazole/THF (Glen Research, Sterling, VI, USA); PO oxidation involved 0.02M $I_2$/THF/$H_2O$ (Glen Research, Sterling, VI, USA). The trityl group was removed on the synthesizer with 3% TCA/dichloromethane (Glen Research, Sterling, VI, USA).

Deprotection

After completion of synthesis the controlled pore glass (CPG) was transferred to a screw cap sterile microfuge tube. The oligonucleotide was cleaved and simultaneously the base and phosphate groups deprotected with 1.0 mL of a mixture of ethanolic ammonia (1:3) for 5 hours at 55° C. The tube was cooled briefly on ice and then the solution was transferred to a 5 mL centrifuge tube. The solid support was washed three times using 0.25 mL of 50% $CH_3CN$ in water and the washes were added to the original solution. The tubes were cooled at −80° C. for 15 min and the solution was dried in a lyophilizer.

The white residue obtained was resuspended in 200 μL of triethylamine trihydrofluoride and heated at 65° C. for 1.5 h to remove the TBDMS groups at the 2'-position. The oligonucleotide was then precipitated in dry methanol (400 μL). The liquid was removed carefully to yield a pellet at the bottom of the tube. Residual methanol was removed in the speed vacuum to give the crude RNA as a white fluffy material.

Purification

Samples were dissolved in 1 mL RNase free water and quantitated at 260 nm. The crude oligonucleotides were purified by denaturing gel electrophoresis (20% acrylamide, 6 M urea). The purified oligonucleotides were desalted using Sephadex G25M (Amersham Biosciences Corp, Piscataway, N.J., USA).

Tables 3-6 show the sequences of the so modified oligonucleotides that were synthesized.

Determination of Activity

Modified oligonucleotides were incubated with PDC as described above in Example 1, and IFN-α production was measured. Table 7 shows the results obtained for oligonucleotides having a base sequence identical to TLR9.2s except for the terminal thymidines, but containing 2'-fluoro or 2'-O-methyl-modifications in positions 1 and 2, 1, 2, 18, and 19, 1 through 4 and 16 through 19, and 16 through 19, or a fully phosphorothioate-substituted backbone, respectively, expressed in % of the IFN-α production measured for TLR9.2s. It is evident that the 2'-fluoro modification generally has less effect on the immunostimulating activity of these oligonucleotides, while 2'-O-methyl modifications almost completely abolish this activity. For the 2'-fluoro modification, modifying only those nucleotides at the 5'-end, farthest away from the 5'-GUCCUUCAA-3' (SEQ ID NO:1) motif, had the least effect, while modifying 4 nucleotides on both ends severely diminished the immunostimulatory activity of the oligonucleotide. Phosphorothioates moderately diminished the IFN-α inducing activity.

Hence, if it seems desirable to modify an immunostimulatory oligonucleotide of the invention, e.g. in order to protect it against nucleolytic degradation, this may be achieved by introducing 2'-fluoro modifications, and preferably by introducing these modifications in such a manner that the nucleotides of SEQ ID NO:1 remain unmodified. However, if it is desired to generate an oligonucleotide comprising SEQ ID NO:1, or 4 or more, 5 or more, 6 or more, 7 or more or 8 or more contiguous nucleotides from SEQ ID NO:1, e.g. 5'-GUCC-3' (SEQ ID NO:2), 5'-GUCCU-3' (SEQ ID NO:3), 5'-GUCCUU-3' (SEQ ID NO:4), 5'-GUCCUUC-3' (SEQ ID NO:5), or 5'-GUCCUUCA-3' (SEQ ID NO:6), but immunostimulating activity is to be avoided, then this may be achieved by introducing 2'-O-methyl modifications, and preferably by introducing these modifications in such a manner that the nucleotides of SEQ ID NO:1 are modified.

TABLE 1 siRINA sequences

| Gene target (starting-base) | | Our no. | Sequence (sense/antisense) | Base composition | | | | SEQ ID NO: |
|---|---|---|---|---|---|---|---|---|
| | | | | A | G | U | C | |
| hTLR2 | (29) | TLR2.1s | 5'-AAGGAGACCUAUAGUGACUdTdT | 8 | 11 | 11 | 8 | SEQ ID NO: 8 |
| | | TLR2.1as | 5'-AGUCACUAUAGGUCUCCUUdTdT | | | | | SEQ ID NO: 9 |
| hTLR3 | (71) | TLR3.1s | 5'-GGAAAGGCUAGCAGUCAUCdTdT | 10 | 9 | 9 | 10 | SEQ ID NO: 10 |
| | | TLR3.1as | 5'-GAUGACUGCUAGCCUUUCCdTdT | | | | | SEQ ID NO: 11 |
| | (331) | TLR3.2s | 5'-ACUAGCUUGGAUGUAGGAUdTdT | 8 | 11 | 11 | 8 | SEQ ID NO: 12 |
| | | TLR3.2as | 5'-AUCCUACAUCCAAGCUAGUdTdT | | | | | SEQ ID NO: 13 |
| hTLR4 | (1039) | TLR4.1s | 5'-UACUUAGACUACUACCUCGdTdT | 8 | 11 | 11 | 8 | SEQ ID NO: 14 |
| | | TLR4.1as | 5'-CGAGGUAGUAGUCUAAGUAdTdT | | | | | SEQ ID NO: 15 |
| | (1597) | TLR4.2s | 5'-AUGGCUGGCAAUUCUUUCCdTdT | 9 | 10 | 10 | 9 | SEQ ID NO: 16 |
| | | TLR4.2as | 5'-GGAAAGAAUUGCCAGCCAUdTdT | | | | | SEQ ID NO: 17 |
| hTLR9 | (1155) | TLR9.1s | 5'-UGGACGGCAACUGUUAUUAdTdT | 8 | 11 | 11 | 8 | SEQ ID NO: 18 |
| | | TLR9.1as | 5'-UAAUAACAGUUGCCGUCCAdTdT | | | | | SEQ ID NO: 19 |
| | (1647) | TLR9.2s | 5'-AGCUUAACCUGUCCUUCAAdTdT | 8 | 11 | 11 | 8 | SEQ ID NO: 20 |
| | | TLR9.2as | 5'-UUGAAGGACAGGUUAAGCUdTdT | | | | | SEQ ID NO: 21 |
| | (1653) | TLR9.3s | 5'-ACCUGUCCUUCAAUUACCAdTdT | 8 | 11 | 11 | 8 | SEQ ID NO: 22 |
| | | TLR9.3as | 5'-UGGUAAUUGAAGGACAGGUdTdT | | | | | SEQ ID NO: 23 |
| | (2251) | TLR9.4s | 5'-CUCAUUCACGGAGCUACCAdTdT | 10 | 9 | 9 | 10 | SEQ ID NO: 24 |
| | | TLR9.4as | 5'-UGGUAGCUCCGUGAAUGAGdTdT | | | | | SEQ ID NO: 25 |
| eGFP | (435) | GFPs | 5'-CUACAACAGCCACAACGUCdTdT | 10 | 9 | 9 | 10 | SEQ ID NO: 26 |
| | | GFPas | 5'-GACGUUGUGGCUGUUGUAGdTdT | | | | | SEQ ID NO: 27 |

Numbers in parentheses indicate the nucleotide position at which the 5'- end of the sense strand of the siRINA matches the target sequence for either hTLR2 (NM_003264), hTLR3 (NM_003265), hTLR4 (NM_138554), hTLR9 (NM_017442), enhanced GFP.

TABLE 2

Single-Stranded RNA Oligonucleotides

| Original sequence | Name[1] | Sequence 5' → 3'[2] | SEQ ID NO: |
|---|---|---|---|
| TLR9.2s | | AGCUUAACCU<u>GUCCUUCAA</u> | SEQ ID NO: 28 |
| | L8A | AAAAAAAACU<u>GUCCUUCAA</u> | SEQ ID NO: 29 |
| | L9A | AAAAAAAAAU<u>GUCCUUCAA</u> | SEQ ID NO: 30 |
| | L10A | AAAAAAAAAA<u>GUCCUUCAA</u> | SEQ ID NO: 31 |
| | L11A | AAAAAAAAAAU<u>CCUUCAA</u> | SEQ ID NO: 32 |
| | L12A | AAAAAAAAAAAA<u>CCUUCAA</u> | SEQ ID NO: 33 |
| | R3A | AGCUUAACCU<u>GUCCUU</u>AAA | SEQ ID NO: 34 |
| | R4A | AGCUUAACCU<u>GUCCU</u>AAAA | SEQ ID NO: 35 |
| | R5A | AGCUUAACCU<u>GUCC</u>AAAAA | SEQ ID NO: 36 |
| | R8A | AGCUUAACCU<u>G</u>AAAAAAA | SEQ ID NO: 37 |
| | DR | U<u>GUCCUUCAA</u>U<u>GUCCUUCAA</u> | SEQ ID NO: 38 |
| | 19U | AGCUUAACCU<u>GUCCUUCA</u>U | SEQ ID NO: 39 |
| | 18/19UU | AGCUUAACCU<u>GUCCUU</u>CUU | SEQ ID NO: 40 |
| | hairpin | AGCUUAACCU<u>GUCCUUCAA</u>-CUACACAAAUUGAAGGACAGGUUAAGCU | SEQ ID NO: 41 |
| | 5'F | F-AGCUUAACCU<u>GUCCUUCAA</u> | SEQ ID NO: 42 |
| | 3'F | AGCUUAACCU<u>GUCCUUCAA</u>-F | SEQ ID NO: 43 |
| | 5'LNA | AGCUUAACCU<u>GUCCUUCAA</u> | SEQ ID NO: 44 |
| | 3'LNA | AGCUUAACCU<u>GUCC</u>UUCAA | SEQ ID NO: 45 |
| | 5'3' LNA | AGCUUAACCU<u>GUCC</u>UUCAA | SEQ ID NO: 46 |
| | 16 mer | UUAACCU<u>GUCCUUCAA</u> | SEQ ID NO: 47 |
| | 12 mer | AACCU<u>GUCCUUCA</u> | SEQ ID NO: 48 |
| TLR9.2as | | UUGAAGGACAGGUUAAGCU | SEQ ID NO: 49 |
| | 5'LNA | UUGAAGGACAGGUUAAGCU | SEQ ID NO: 50 |
| | 3'LNA | UUGAAGGACAGGUUAAGCU | SEQ ID NO: 51 |
| | 5'3' LNA | UUGAAGGACAGGUUAAGCU | SEQ ID NO: 52 |
| | polyA | AAAAAAAAAAAAAAAAAAA | SEQ ID NO: 53 |
| | polyU | UUUUUUUUUUUUUUUUUUU | SEQ ID NO: 54 |

[1]L8A: read „8 A from left" (5'end); R3A: read „3 A from right" (3'end); DR: read „double right" (sequence containing the 3' 9 mer sequence of 9.2 sense two times); 19U: read „base at position 19 replaced by U"; 18/19UU read „bases at position 18 and 19 replaced by U";
[2]underlined: 3' 9 mer sequence of TLR9.2s; F: FITC; bold: LNA modification.

TABLE 3

Oligonucleotides containing ribofluoro modifications

| Our No. | Sequence | D/tube | Mass | OD/mg | Extn coeff. e260 * 10⁻³ | SEQ ID NO: |
|---|---|---|---|---|---|---|
| 2792 | fAfGfCfUUAACCUGUCCUUCAA | 2 | 5950.57 | 29.8 | 177 | SEQ ID NO: 55 |
| 2793 | fAfGCUUAACCUGUCCUUCfAfAdT | 3 | 6254.77 | 29.6 | 185 | SEQ ID NO: 56 |
| 2794 | fAfGfCfUUAACCUGUCCUfUfCfAfAdT | 2 | 6262.77 | 29.6 | 185 | SEQ ID NO: 57 |
| 2795 | AGCUUAACCUGUCCUfUfCfAfAdT | 3 | 6254.77 | 29.6 | 185 | SEQ ID NO: 58 |
| 2796 | fUfUfGfAAGGACAGGUUAAGCU | 3 | 6133.73 | 32.5 | 199 | SEQ ID NO: 59 |
| 2797 | fUfUGAAGGACAGGUUAAGfCfUdT | 2 | 6437.93 | 32.2 | 207 | SEQ ID NO: 60 |
| 2798 | fUfUfGfAAGGACAGGUUAfAfGfCfUdT | 2 | 6445.93 | 32.1 | 207 | SEQ ID NO: 61 |
| 2799 | UUGAAGGACAGGUUAfAfGfCfUdT | 2 | 6437.93 | 32.2 | 207 | SEQ ID NO: 62 |

TABLE 4

Oligonucleotides containing phosphorothioates

| Our No. | Sequence | OD/tube | Expected Mass | OD/mg | Extn coeff. e260 * 10⁻³ | SEQ ID NO: |
|---|---|---|---|---|---|---|
| 2808 | AsGsCsUsUsAsAsCsCsUsGsUsCsCsUsUsCsAsA | 2 | 16230.57 | 28.4 | 177 | SEQ ID NO: 63 |
| 2809 | UsUsGsAsAsGsGsAsCsAsGsGsUsUsAsAsGsCsU | 2 | 6413.73 | 31.03 | 199 | SEQ ID NO: 64 |

TABLE 5

Oligonucleotides containing 2'-O-methyl modifications

| Our No. | Sequence | OD/tube | Expected Mass | OD/mg | Extn coeff. e260*10$^{-3}$ | SEQ ID NO: |
|---|---|---|---|---|---|---|
| 2800 | oAoGoCoUUAACCUGUCCUUCAA | 3 | 5998.69 | 29.6 | 177 | SEQ ID NO: 65 |
| 2801 | oAoGCUUAACCUGUCCUUCoAoA | 3 | 5998.69 | 29.6 | 177 | SEQ ID NO: 66 |
| 2802 | oAoGoCoUUAACCUGUCCUoUoCoAoA | 3 | 6054.81 | 29.28 | 177 | SEQ ID NO: 67 |
| 2803 | AGCUUAACCUGUCCUoUoCoAoA | 3 | 5998.69 | 29.55 | 177 | SEQ ID NO: 68 |
| 2804 | oUoUoGoAAGGACAGGUUAAGCU | 3 | 6181.85 | 32.20 | 199 | SEQ ID NO: 69 |
| 2805 | UoUGAAGGACAGGUUAAGoCoU | 3 | 6181.85 | 32.20 | 199 | SEQ ID NO: 70 |
| 2806 | oUoUoGoAAGGACAGGUUAoAoGoCoU | 3 | 6237.97 | 31.91 | 199 | SEQ ID NO: 71 |
| 2807 | UUGAAGGACAGGUUAoAoGoCoU | 3 | 6181.85 | 32.20 | 199 | SEQ ID NO: 72 |
| 2869 | AGoCoUoUAAoCoCoUGoUoCoCoUoUoCAA | 2 | 6110.93 | 29.2 | 177 | SEQ ID NO: 73 |
| 2870 | oAGoCUoUAoACoCUoGUoCCoUUoCAoA | 2 | 6082.87 | 29.1 | 177 | SEQ ID NO: 74 |
| 2871 | AoGCoUoAAoCCoUGoUCoCUoUCoAA | 2 | 6068.84 | 29.2 | 177 | SEQ ID NO: 75 |
| 2872 | AGCUoUAACCoUGUCCUUoCAA | 2 | 5984.66 | 29.6 | 177 | SEQ ID NO: 76 |
| 2873 | oUoUGAAGGAoCAGGoUoUAAGoCoU | 2 | 6223.94 | 32.0 | 199 | SEQ ID NO: 77 |
| 2874 | oUUoGAoAGoGAoCAoGGoUUoAAoGCU | 2 | 6251.64 | 31.8 | 199 | SEQ ID NO: 78 |
| 2875 | UoUGoAAoGGoACoAGoGUoUAoAGoCU | 2 | 6266.03 | 31.8 | 199 | SEQ ID NO: 79 |
| 2876 | UoUGAAGGAoCAGGUoUAAGCU | 2 | 6167.82 | 32.3 | 199 | SEQ ID NO: 80 |

TABLE 6

Oligonucleotides containing Locked Nucleotides

| Our No. | Sequence | Expected Mass | Experimental mass | OD/mg | SEQ ID NO: |
|---|---|---|---|---|---|
| 2784 | ALGLm5CLTLUAACCUGUCCUUCAA | 6018.82 | 6018.05 | 91.6 | SEQ ID NO: 81 |
| 2785 | AGCUUAACCUGUCCUTLm5CLALAL | 6018.32 | 6017.99 | 84.84 | SEQ ID NO: 82 |
| 2786 | ALGLm5CLTLUAACCUGUCCUTLm5CLALAL | 6095.09 | 6093.98 | 94.79 | SEQ ID NO: 83 |
| 2787 | ALGLCUUAACCUGUCCUUCALAL | 5990.63 | 5989.88 | 92.66 | SEQ ID NO: 84 |
| 2788 | TLTLGLALAGGACAGGUUAAGCU | 6201.96 | 6201.04 | 90.6 | SEQ ID NO: 85 |
| 2789 | UUGAAGGACAGGUUAALGLm5CLTL | 6201.96 | 6200.97 | 92.22 | SEQ ID NO: 86 |
| 2790 | TLTLGLALAGGACAGGUUAALGLm5CLTL | 6278.23 | 6277.1 | 93.18 | SEQ ID NO: 87 |
| 2791 | TLTLGAAGGACAGGUUAAGm5CLTL | 6230.15 | 6229.29 | 92.2 | SEQ ID NO: 88 |

In Tables 3-6, strands are shown written 5' to 3'. dT means 2'-deoxy thymidine, a leading lower case "s" indicates a 5'-phosphorothioate group. Locked nucleic acids are indicated by a trailing "L". A leading lower case "d" indicates a deoxy residue. A leading "o" indicates a 2'-O-methyl modified nucleotide. A leading "f" indicates a 2'-fluoro nucleotide. "T" indicates a 5-methyl-uridine and "m5C" indicates a 5-methyl-cytidine. Six of the sequences in the fluoro set end in "dT" overhangs as the appropriate CPG containing ribofluoro nucleosides were not available at that time. These are 2793, 2794, 2795, 2797, 2798, and 2799. Extn coeff.e260*10$^{-3}$ is the molar extinction coefficient of the oligonucleotide at 260 nm wavelength divided by (1000×1/(mol×cm)

TABLE 7

Interferon production in PDC cells incubated with modified oligonucleotides derived from RNA9.2s

| Our No. | IFN-α production (in % of control) |
|---|---|
| TLR9.2s | 100% (4.5 ng/ml IFN-α) |
| 2792 | 72% |
| 2793 | 56% |
| 2794 | 11% |
| 2795 | 26% |
| 2800 | 9% |

TABLE 7-continued

Interferon production in PDC cells incubated with modified oligonucleotides derived from RNA9.2s

| Our No. | IFN-α production (in % of control) |
|---|---|
| 2801 | 11% |
| 2802 | 12% |
| 2803 | 8% |
| 2808 | 64% |

TABLE 8

Gene transcripts comprising a sequence identical or complementary to SEQ ID NO: 1 spectrin, alpha, erythrocytic 1 (elliptocytosis 2)
spectrin, beta, non-erythrocytic 1 (SPTBN1), transcript variant 1 and 2
ryanodine receptor 1 (skeletal) (RYR1)
WD repeat domain 9 (WDR9), transcript variant 2
WD repeat domain 9 (WDR9), transcript variant 1
phosphoglycerate kinase 1 (PGK1)
SEC11-like 3 (S. cerevisiae) (SEC11L3)
SET domain, bifurcated 1 (SETDB1)
HBS1-like (S. cerevisiae) (HBS1L)
activation-induced cytidine deaminase (AICDA)
cholinergic receptor, muscarinic 3 (CHRM3)
transmembrane protein 1 (TMEM1), transcript variant 1 and 2
SFRS protein kinase 2 (SRPK2), transcript variant 1
step II splicing factor SLU7 (SLU7)
myosin, heavy polypeptide 7, cardiac muscle, beta
keratin, hair, acidic, 7 (KRTHA7)
keratin, hair, acidic, 8 (KRTHA8)
inter-alpha (globulin) inhibitor H3 (ITIH3)
integrin, alpha 4 (antigen CD49D, alpha 4 subunit of
integrin, alpha 2 (CD49B, alpha 2 subunit of VLA-2
cleavage stimulation factor, 3' pre-RNA, subunit 2
cubilin (intrinsic factor-cobalamin receptor) (CUBN)
cytochrome P450, family 2, subfamily F, polypeptide 1
UDP-N-acetyl-alpha-D-galactosamine:polypeptide-N-acetylgalactosaminyltransferase 8 (GalNAc-T8) (GALNT8)
UDP-N-acetyl-alpha-D-galactosamine:polypeptide-N-acetylgalactosaminyltransferase 7 (GalNAc-T7) (GALNT7)
E74-like factor 2 (ets domain transcription factor) (ELF2), transcript variant 1 and 2
endogenous retroviral family W, env(C7), member 1 (syncytin) (ERVWE1)
solute carrier family 7 (cationic amino acid transporter, y+ system), member 6 (SLC7A6)
AT-binding transcription factor 1 (ATBF1)
gasdermin-like (GSDML)
sodium channel, nonvoltage-gated 1, gamma (SCNN1G)
zinc finger and SCAN domain containing 1 (ZSCAN1)
ubiquitin specific protease 54 (USP54)
vitamin D (1,25-dihydroxyvitamin D3) receptor (VDR)
CD84 antigen (leukocyte antigen) (CD84)
alpha-kinase 3 (ALPK3)
interferon, alpha 2 (IFNA2)
zinc finger protein 452 (ZNF452)
SNF7 domain containing 2 (SNF7DC2)
platelet/endothelial cell adhesion molecule (CD31 antigen) (PECAM1)
hypothetical protein DKFZp547K1113 (DKFZp547K1113)
repressor of estrogen receptor activity (REA)
fibrous sheath interacting protein 1 (FSIP1)
neural cell adhesion molecule 1 (NCAM1)
immunoglobulin superfamily, member 4 (IGSF4)
protein inhibitor of activated STAT, 2 (PIAS2), transcript variant alpha and beta
F-box protein 21 (FBXO21), transcript variant 1 and 2
F-box protein 22 (FBXO22), transcript variant 2
Leucine-zipper-like transcription regulator 1 (LZTR1)
Nuclear receptor subfamily 1, group H, member 2 (NR1H2)
UDP-Gal:betaGlcNAc beta 1,4-galactosyltransferase, polypeptide 1 (B4GALT1)
CSRP2 binding protein (CSRP2BP), transcript variant 1 and 2
cleavage stimulation factor, 3' pre-RNA, subunit 1, 50 kDa (CSTF1)
solute carrier organic anion transporter family, member 4A1 (SLCO4A1)
serine/threonine kinase 6 (STK6), transcript variant 3, 4, 5 and 6
zinc finger protein 295 (ZNF295)
FLJ16231 protein (FLJ16231)
zinc finger protein 646 (ZNF646)
mediator of RNA polymerase II transcription, subunit 12 homolog (yeast)-like TABLE 8-continued Gene transcripts comprising a sequence identical or complementary to SEQ ID NO: 1

(MED12L)
olfactory receptor, family 2, subfamily W, member 1 (OR2W1)
interferon, alpha 7 (IFNA7)
apolipoprotein B (including Ag(x) antigen) (APOB)
syndecan binding protein (syntenin) (SDCBP), transcript variant 1, 2, 3, 4 and 5
erbb2 interacting protein (ERBB2IP), transcript variant 2 and 7
fibroblast growth factor 23 (FGF23)
MARCKS-like 1 (MARCKSL1)
v-src sarcoma (Schmidt-Ruppin A-2) viral oncogene homolog (avian) (SRC), transcript variant 1 and 2
v-src sarcoma (Schmidt-Ruppin A-2) viral oncogene homolog (avian) (SRC), transcript variant 2
CUB and Sushi multiple domains 2 (CSMD2)
family with sequence similarity 49, member B (FAM49B)
pyruvate dehydrogenase kinase, isoenzyme 1 (PDK1), nuclear gene encoding mitochondrial protein
neurotrophic tyrosine kinase, receptor, type 3 (NTRK3), transcript variant 3
ret finger protein 2 (RFP2), transcript variant 2, 3 and 4
KIAA1950 protein (KIAA1950)
collagen, type XIV, alpha 1 (undulin) (COL14A1)
tektin 1 (TEKT1)
zinc finger protein 31 (KOX 29) (ZNF31)
Leucine-rich repeat-containing G protein-coupled receptor 4 (LGR4)
protein kinase, DNA-activated, catalytic polypeptide (PRKDC)
scavenger receptor class B, member 1 (SCARB1)

What is claimed is:

1. A method of stimulating an immune response in a mammal comprising the steps of administering to said mammal an oligonucleotide agent comprising a sequence that differs by not more than 1 or not more than 2 nucleotides from SEQ ID NO:1, and assaying the mammal for IFNα expression prior to and after the administering step to determine that the immune response was stimulated in the mammal, wherein the oligonucleotide agent is at least 19 nucleotides in length.

2. The method of claim 1, wherein the oligonucleotide agent comprises SEQ ID NO: 1.

3. The method of claim 1, wherein said sequence comprises the sequence of any one the following: SEQ ID NO: 2, SEQ ID NO: 3, SEQ ID NO: 4, SEQ ID NO: 5, and SEQ ID NO: 6.

4. A method of concomitantly inhibiting the expression of a gene and inducing an immune response in a mammal, comprising administering to said mammal an iRNA agent comprising a sequence that differs by not more than 1 or not more than 2 nucleotides of SEQ ID NO:1 and assaying the mammal for IFNα expression prior to and after the administering step to determine that the immune response was stimulated in the mammal, wherein the iRNA agent is at least 19 nucleotides in length.

5. The method of claim 4, wherein said sequence comprises the sequence of any one the following: SEQ ID NO: 2, SEQ ID NO: 3, SEQ ID NO: 4, SEQ ID NO: 5, and SEQ ID NO: 6.

6. The method of claim 4, wherein the iRNA agent comprises SEQ ID NO:1.

7. The method of claim 1, wherein the oligonucleotide agent is an siRNA comprising a sense strand and an antisense strand, wherein the antisense strand comprises a sequence of at least 19, 20, 21 or 23 nucleotides.

8. The method of claim 7, wherein the sense strand comprises a sequence of at least 19, 20, or 21 contiguous nucleotides of SEQ ID NO: 20.

9. The method of claim 7, wherein the sense strand consists of SEQ ID NO:20.

10. The method of claim 7, wherein the sense strand comprises a sequence of at least 19, 20, or 21 contiguous nucleotides of SEQ ID NO: 22.

11. The method of claim 7, wherein the sense strand consists of SEQ ID NO:22.

12. The method of claim 7, wherein the sense strand comprises a sequence that differs by not more than 1 or not more than 2 nucleotides from SEQ ID NO:1.

13. The method of claim 1, wherein the oligonucleotide agent is single stranded.

14. The method of claim 1, wherein the oligonucleotide agent is a hybrid oligonucleotide.

15. The method of claim 1, wherein said method is used for treatment of cancer, autoimmune disorders, asthma, respiratory allergies, food allergies, bacteria infections, parasitic infections, or viral infections and wherein the mammal is in need of said treatment.

16. The method of claim 1, wherein an antigen is conjugated to the oligonucleotide agent at a position other than the accessible 5' end.

17. The method of claim 1, wherein an antigen is conjugated to the oligonucleotide by a non-nucleotidic linker.

18. The method of claim 17, wherein the antigen is conjugated to the oligonucleotide at a position other than its 3' end.

19. The method of claim 1, wherein immune recognition of the oligonucleotide requires toll-like receptor 7 (TLR7).

20. The method of claim 1, wherein the oligonucleotide comprises two repeats of SEQ ID NO:1.

21. The method of claim 20, wherein the oligonucleotide comprises SEQ ID NO:38.

22. The method of claim 7, wherein the immunostimulatory activity is maintained while abolishing the silencing activity of the siRNA.

* * * * *

SEQUENCE LISTING

<160> NUMBER OF SEQ ID NOS: 89

<210> SEQ ID NO 1
<211> LENGTH: 9
<212> TYPE: RNA
<213> ORGANISM: Artificial Sequence
<220> FEATURE:
<223> OTHER INFORMATION: Synthetically generated oligonucleotide

<400> SEQUENCE: 1 guccuucaa                                                           9

<210> SEQ ID NO 2
<211> LENGTH: 4
<212> TYPE: RNA
<213> ORGANISM: Artificial Sequence
<220> FEATURE:
<223> OTHER INFORMATION: Synthetically generated oligonucleotide

<400> SEQUENCE: 2 gucc                                                                4

<210> SEQ ID NO 3
<211> LENGTH: 5
<212> TYPE: RNA
<213> ORGANISM: Artificial Sequence
<220> FEATURE:
<223> OTHER INFORMATION: Synthetically generated oligonucleotide

<400> SEQUENCE: 3 guccu                                                               5

<210> SEQ ID NO 4
<211> LENGTH: 6
<212> TYPE: RNA
<213> ORGANISM: Artificial Sequence
<220> FEATURE:
<223> OTHER INFORMATION: Synthetically generated oligonucleotide -continued

```
<400> SEQUENCE: 4 guccuu                                                                    6

<210> SEQ ID NO 5
<211> LENGTH: 7
<212> TYPE: RNA
<213> ORGANISM: Artificial Sequence
<220> FEATURE:
<223> OTHER INFORMATION: Synthetically generated oligonucleotide

<400> SEQUENCE: 5 guccuuc                                                                   7

<210> SEQ ID NO 6
<211> LENGTH: 8
<212> TYPE: RNA
<213> ORGANISM: Artificial Sequence
<220> FEATURE:
<223> OTHER INFORMATION: Synthetically generated oligonucleotide

<400> SEQUENCE: 6 guccuuca                                                                  8

<210> SEQ ID NO 7
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 7
gggggacgat cgtcgggggg                                                    20

<210> SEQ ID NO 8
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 8
aaggagaccu auagugacun n                                                  21

<210> SEQ ID NO 9
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 9
agucacuaua ggucuccuun n                                                  21

<210> SEQ ID NO 10
<211> LENGTH: 21
<212> TYPE: DNA
<213> ORGANISM: Artificial Sequence
<220> FEATURE:
<223> OTHER INFORMATION: Synthetically generated oligonucleotide
```

```
<220> FEATURE:
<221> NAME/KEY: misc_feature
<222> LOCATION: 20, 21
<223> OTHER INFORMATION: n = 2'-deoxy thymidine

<400> SEQUENCE: 10
ggaaaggcua gcagucaucn n                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 11
gaugacugcu agccuuuccn n                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 12
acuagcuugg auguaggaun n                                              21

<210> SEQ ID NO 13
<211> LENGTH: 21
<212> TYPE: DNA
<213> ORGANISM: Artificial Sequence
<220> FEATURE:
<221> NAME/KEY: misc_feature
<222> LOCATION: 20, 21
<223> OTHER INFORMATION: n = 2'-deoxy thymidine
<220> FEATURE:
<223> OTHER INFORMATION: Synthetically generated oligonucleotide

<400> SEQUENCE: 13
auccuacauc caagcuagun n                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 14
uacuuagacu acuaccucgn n                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetically generated oligonucleotide
```

```
<220> FEATURE:
<221> NAME/KEY: misc_feature
<222> LOCATION: 20, 21
<223> OTHER INFORMATION: n = 2'-deoxy thymidine

<400> SEQUENCE: 15
cgagguagua gucuaaguan n                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 16
auggcuggca auucuuuccn n                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 17
ggaaagaauu gccagccaun n                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 18
uggacggcaa cuguuauuan n                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 19
uaauaacagu ugccguccan n                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetically generated oligonucleotide
```

-continued

```
<220> FEATURE:
<221> NAME/KEY: misc_feature
<222> LOCATION: 20, 21
<223> OTHER INFORMATION: n = 2'-deoxy thymidine

<400> SEQUENCE: 20
agcuuaaccu guccuucaan n                                               21

<210> SEQ ID NO 21
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 21
uugaaggaca gguuaagcun n                                               21

<210> SEQ ID NO 22
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 22
accuguccuu caauuaccan n                                               21

<210> SEQ ID NO 23
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 23
ugguaauuga aggacaggun n                                               21

<210> SEQ ID NO 24
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 24
cucauucacg gagcuaccan n                                               21

<210> SEQ ID NO 25
<211> LENGTH: 21
<212> TYPE: DNA
<213> ORGANISM: Artificial Sequence
<220> FEATURE:
<223> OTHER INFORMATION: Synthetically generated oligonucleotide
```

```
<220> FEATURE:
<221> NAME/KEY: misc_feature
<222> LOCATION: 20, 21
<223> OTHER INFORMATION: n = 2'-deoxy thymidine

<400> SEQUENCE: 25
ugguagcucc gugaaugagn n                                          21

<210> SEQ ID NO 26
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 26
cuacaacagc cacaacgucn n                                          21

<210> SEQ ID NO 27
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = 2'-deoxy thymidine

<400> SEQUENCE: 27
gacguugugg cuguuguagn n                                          21

<210> SEQ ID NO 28
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 28
agcuuaaccu guccuucaa                                             19

<210> SEQ ID NO 29
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 29
aaaaaaaacu guccuucaa                                             19

<210> SEQ ID NO 30
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 30
aaaaaaaaau guccuucaa                                             19

<210> SEQ ID NO 31
<211> LENGTH: 19
```

<210> SEQ ID NO 32
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 31
aaaaaaaaaa guccuucaa                                              19

<210> SEQ ID NO 32
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 32
aaaaaaaaaa auccuucaa                                              19

<210> SEQ ID NO 33
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 33 aaaaaaaaa aaccuucaa                                               19

<210> SEQ ID NO 34
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 34
agcuuaaccu guccuuaaa                                              19

<210> SEQ ID NO 35
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 35
agcuuaaccu guccuaaaa                                              19

<210> SEQ ID NO 36
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 36
agcuuaaccu guccaaaaa                                              19

<210> SEQ ID NO 37
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 37
agcuuaaccu gaaaaaaaa                                              19

<210> SEQ ID NO 38
<211> LENGTH: 20
<212> TYPE: RNA
<213> ORGANISM: Artificial Sequence
<220> FEATURE:
<223> OTHER INFORMATION: Synthetically generated oligonucleotide

<400> SEQUENCE: 38
uguccuucaa uguccuucaa                                                 20

<210> SEQ ID NO 39
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 39
agcuuaaccu guccuucau                                                  19

<210> SEQ ID NO 40
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 40
agcuuaaccu guccuucuu                                                  19

<210> SEQ ID NO 41
<211> LENGTH: 47
<212> TYPE: RNA
<213> ORGANISM: Artificial Sequence
<220> FEATURE:
<223> OTHER INFORMATION: Synthetically generated oligonucleotide

<400> SEQUENCE: 41
agcuuaaccu guccuucaac uacacaaauu gaaggacagg uuaagcu                   47

<210> SEQ ID NO 42
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 42
agcuuaaccu guccuucaa                                                  19

<210> SEQ ID NO 43
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 43
agcuuaaccu guccuucaa                                                  19

<210> SEQ ID NO 44
<211> LENGTH: 19
<212> TYPE: RNA
<213> ORGANISM: Artificial Sequence
<220> FEATURE:
<223> OTHER INFORMATION: Synthetically generated oligonucleotide -continued

<400> SEQUENCE: 44
agcuuaaccu guccuucaa					19

<210> SEQ ID NO 45
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 45
agcuuaaccu guccuucaa					19

<210> SEQ ID NO 46
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 46
agcuuaaccu guccuucaa					19

<210> SEQ ID NO 47
<211> LENGTH: 16
<212> TYPE: RNA
<213> ORGANISM: Artificial Sequence
<220> FEATURE:
<223> OTHER INFORMATION: Synthetically generated oligonucleotide

<400> SEQUENCE: 47
uuaaccuguc cuucaa					16

<210> SEQ ID NO 48
<211> LENGTH: 13
<212> TYPE: RNA
<213> ORGANISM: Artificial Sequence
<220> FEATURE:
<223> OTHER INFORMATION: Synthetically generated oligonucleotide

<400> SEQUENCE: 48
aaccuguccu uca					13

<210> SEQ ID NO 49
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 49
uugaaggaca gguuaagcu					19

<210> SEQ ID NO 50
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 50
uugaaggaca gguuaagcu					19

<210> SEQ ID NO 51
<211> LENGTH: 19

```
<212> TYPE: RNA
<213> ORGANISM: Artificial Sequence
<220> FEATURE:
<223> OTHER INFORMATION: Synthetically generated oligonucleotide

<400> SEQUENCE: 51
uugaaggaca gguuaagcu                                                      19

<210> SEQ ID NO 52
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 52
uugaaggaca gguuaagcu                                                      19

<210> SEQ ID NO 53
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 53
aaaaaaaaaa aaaaaaaaa                                                      19

<210> SEQ ID NO 54
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 54
uuuuuuuuuu uuuuuuuuu                                                      19

<210> SEQ ID NO 55
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 2'-fluoro adenine
<220> FEATURE:
<221> NAME/KEY: misc_feature
<222> LOCATION: 2
<223> OTHER INFORMATION: n = 2'-fluoro guanosine
<220> FEATURE:
<221> NAME/KEY: misc_feature
<222> LOCATION: 3
<223> OTHER INFORMATION: n = 2'-fluoro cytidine
<220> FEATURE:
<221> NAME/KEY: misc_feature
<222> LOCATION: 4
<223> OTHER INFORMATION: n = 2'-fluoro  uridine

<400> SEQUENCE: 55
nnnnuaaccu guccuucaa                                                      19

<210> SEQ ID NO 56
<211> LENGTH: 20
<212> TYPE: DNA
<213> ORGANISM: Artificial Sequence
<220> FEATURE:
<223> OTHER INFORMATION: Synthetically generated oligonucleotide
```

```
<220> FEATURE:
<221> NAME/KEY: misc_feature
<222> LOCATION: 1, 18, 19
<223> OTHER INFORMATION: n = 2'-fluoro adenine
<220> FEATURE:
<221> NAME/KEY: misc_feature
<222> LOCATION: 2
<223> OTHER INFORMATION: n = 2'-fluoro guanosine
<220> FEATURE:
<221> NAME/KEY: misc_feature
<222> LOCATION: 20
<223> OTHER INFORMATION: n = 2'-deoxy thymidine

<400> SEQUENCE: 56
nncuuaaccu guccuucnnn                                           20

<210> SEQ ID NO 57
<211> LENGTH: 20
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 18, 19
<223> OTHER INFORMATION: n = 2'-fluoro adenine
<220> FEATURE:
<221> NAME/KEY: misc_feature
<222> LOCATION: 2
<223> OTHER INFORMATION: n = 2'-fluoro guanosine
<220> FEATURE:
<221> NAME/KEY: misc_feature
<222> LOCATION: 3, 17
<223> OTHER INFORMATION: n = 2'-fluoro cytidine
<220> FEATURE:
<221> NAME/KEY: misc_feature
<222> LOCATION: 4, 16
<223> OTHER INFORMATION: n = 2'-fluoro uridine
<220> FEATURE:
<221> NAME/KEY: misc_feature
<222> LOCATION: 20
<223> OTHER INFORMATION: n = 2'-deoxy thymidine

<400> SEQUENCE: 57
nnnnuaaccu guccunnnnn                                           20

<210> SEQ ID NO 58
<211> LENGTH: 20
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 16
<223> OTHER INFORMATION: n = 2'-fluoro uridine
<220> FEATURE:
<221> NAME/KEY: misc_feature
<222> LOCATION: 17
<223> OTHER INFORMATION: n = 2'-fluoro cytidine
<220> FEATURE:
<221> NAME/KEY: misc_feature
<222> LOCATION: 18, 19
<223> OTHER INFORMATION: n = 2'-fluoro adenine
<220> FEATURE:
<221> NAME/KEY: misc_feature
<222> LOCATION: 20
<223> OTHER INFORMATION: n = 2'-deoxy thymidine

<400> SEQUENCE: 58
agcuuaaccu guccunnnnn                                           20

<210> SEQ ID NO 59
<211> LENGTH: 19
```

```
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2
<223> OTHER INFORMATION: n = 2'-fluoro  uridine
<220> FEATURE:
<221> NAME/KEY: misc_feature
<222> LOCATION: 3
<223> OTHER INFORMATION: n = 2'-fluoro guanosine
<220> FEATURE:
<221> NAME/KEY: misc_feature
<222> LOCATION: 4
<223> OTHER INFORMATION: n = 2'-fluoro adenine

<400> SEQUENCE: 59
nnnnaggaca gguuaagcu                                              19

<210> SEQ ID NO 60
<211> LENGTH: 20
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 19
<223> OTHER INFORMATION: n = 2'-fluoro  uridine
<220> FEATURE:
<221> NAME/KEY: misc_feature
<222> LOCATION: 18
<223> OTHER INFORMATION: n = 2'-fluoro cytidine
<220> FEATURE:
<221> NAME/KEY: misc_feature
<222> LOCATION: 20
<223> OTHER INFORMATION: n = 2'-deoxy thymidine

<400> SEQUENCE: 60
nngaaggaca gguuaagnnn                                             20

<210> SEQ ID NO 61
<211> LENGTH: 20
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 19
<223> OTHER INFORMATION: n = 2'-fluoro  uridine
<220> FEATURE:
<221> NAME/KEY: misc_feature
<222> LOCATION: 3, 17
<223> OTHER INFORMATION: n = 2'-fluoro guanosine
<220> FEATURE:
<221> NAME/KEY: misc_feature
<222> LOCATION: 4, 16
<223> OTHER INFORMATION: n = 2'-fluoro adenine
<220> FEATURE:
<221> NAME/KEY: misc_feature
<222> LOCATION: 18
<223> OTHER INFORMATION: n = 2'-fluoro cytidine
<220> FEATURE:
<221> NAME/KEY: misc_feature
<222> LOCATION: 20
<223> OTHER INFORMATION: n = 2'-deoxy thymidine

<400> SEQUENCE: 61
nnnnaggaca gguuannnn                                              20

<210> SEQ ID NO 62
<211> LENGTH: 20
```

```
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 16
<223> OTHER INFORMATION: n = 2'-fluoro adenine
<220> FEATURE:
<221> NAME/KEY: misc_feature
<222> LOCATION: 17
<223> OTHER INFORMATION: n = 2'-fluoro guanosine
<220> FEATURE:
<221> NAME/KEY: misc_feature
<222> LOCATION: 18
<223> OTHER INFORMATION: n = 2'-fluoro cytidine
<220> FEATURE:
<221> NAME/KEY: misc_feature
<222> LOCATION: 19
<223> OTHER INFORMATION: n = 2'-fluoro  uridine
<220> FEATURE:
<221> NAME/KEY: misc_feature
<222> LOCATION: 20
<223> OTHER INFORMATION: n = 2'-deoxy thymidine

<400> SEQUENCE: 62
uugaaggaca gguuannnnn                                                   20

<210> SEQ ID NO 63
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 7, 8, 9, 10, 11, 12, 13, 14, 15, 16,
      17, 18
<223> OTHER INFORMATION: mod_base = 5'-phosphorothioate linkage
      corresponding base

<400> SEQUENCE: 63
agcuuaaccu guccuucaa                                                    19

<210> SEQ ID NO 64
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 5, 6, 7, 8, 9, 10, 11, 12, 13, 14, 15, 16,
      17, 18
<223> OTHER INFORMATION: mod_base = 5'-phosphorothioate linkage
      corresponding base

<400> SEQUENCE: 64
uugaaggaca gguuaagcu                                                    19

<210> SEQ ID NO 65
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4
<223> OTHER INFORMATION: /mod_base = 2'-O-methyl  modification
      corresponding base

<400> SEQUENCE: 65
```
agcuuaaccu guccuucaa                                          19

<210> SEQ ID NO 66
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 18, 19
<223> OTHER INFORMATION: /mod_base = 2'-O-methyl modification
      corresponding base

<400> SEQUENCE: 66
agcuuaaccu guccuucaa                                          19

<210> SEQ ID NO 67
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 16, 17, 18, 19
<223> OTHER INFORMATION: /mod_base = 2'-O-methyl modification
      corresponding base

<400> SEQUENCE: 67
agcuuaaccu guccuucaa                                          19

<210> SEQ ID NO 68
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 16, 17, 18, 19
<223> OTHER INFORMATION: /mod_base = 2'-O-methyl modification
      corresponding base

<400> SEQUENCE: 68
agcuuaaccu guccuucaa                                          19

<210> SEQ ID NO 69
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4
<223> OTHER INFORMATION: /mod_base = 2'-O-methyl modification
      corresponding base

<400> SEQUENCE: 69
uugaaggaca gguuaagcu                                          19

<210> SEQ ID NO 70
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 18, 19

```
<223> OTHER INFORMATION: /mod_base = 2'-O-methyl modification
      corresponding base

<400> SEQUENCE: 70
uugaaggaca gguuaagcu                                                    19

<210> SEQ ID NO 71
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 3, 4, 16, 17, 18, 19
<223> OTHER INFORMATION: /mod_base = 2'-O-methyl modification
      corresponding base

<400> SEQUENCE: 71
uugaaggaca gguuaagcu                                                    19

<210> SEQ ID NO 72
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 16, 17, 18, 19
<223> OTHER INFORMATION: /mod_base = 2'-O-methyl modification
      corresponding base

<400> SEQUENCE: 72
uugaaggaca gguuaagcu                                                    19

<210> SEQ ID NO 73
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 3, 4, 5, 8, 9, 10, 12, 13, 14, 15, 16, 17,
<223> OTHER INFORMATION: /mod_base = 2'-O-methyl modification
      corresponding base

<400> SEQUENCE: 73
agcuuaaccu guccuucaa                                                    19

<210> SEQ ID NO 74
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 5, 7, 9, 11, 13, 15, 17, 19
<223> OTHER INFORMATION: /mod_base = 2'-O-methyl modification
      corresponding base

<400> SEQUENCE: 74
agcuuaaccu guccuucaa                                                    19

<210> SEQ ID NO 75
<211> LENGTH: 19
<212> TYPE: RNA
<213> ORGANISM: Artificial Sequence
```

```
<220> FEATURE:
<223> OTHER INFORMATION: Synthetically generated oligonucleotide
<220> FEATURE:
<221> NAME/KEY: modified_base
<222> LOCATION: 2, 4, 6, 8, 10, 12, 14, 16, 18
<223> OTHER INFORMATION: /mod_base = 2'-O-methyl modification
      corresponding base

<400> SEQUENCE: 75
agcuuaaccu guccuucaa                                                       19

<210> SEQ ID NO 76
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 5, 10, 17,
<223> OTHER INFORMATION: /mod_base = 2'-O-methyl modification
      corresponding base

<400> SEQUENCE: 76
agcuuaaccu guccuucaa                                                       19

<210> SEQ ID NO 77
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 9, 13, 14, 18, 19
<223> OTHER INFORMATION: /mod_base = 2'-O-methyl modification
      corresponding base

<400> SEQUENCE: 77
uugaaggaca gguuaagcu                                                       19

<210> SEQ ID NO 78
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 3, 5, 7, 9, 11, 13, 15, 17,
<223> OTHER INFORMATION: /mod_base = 2'-O-methyl modification
      corresponding base

<400> SEQUENCE: 78
uugaaggaca gguuaagcu                                                       19

<210> SEQ ID NO 79
<211> LENGTH: 19
<212> TYPE: RNA
<213> ORGANISM: Artificial Sequence
<220> FEATURE:
<221> NAME/KEY: modified_base
<222> LOCATION: 1, 3, 5, 7, 9, 11, 13, 15, 17, 19
<223> OTHER INFORMATION: /mod_base = 2'-O-methyl modification
      corresponding base
<220> FEATURE:
<223> OTHER INFORMATION: Synthetically generated oligonucleotide
<220> FEATURE:
<221> NAME/KEY: modified_base
<222> LOCATION: 2, 4, 6, 8, 10, 12, 14, 16, 18
<223> OTHER INFORMATION: /mod_base = 2'-O-methyl modification
      corresponding base
```

<400> SEQUENCE: 79
uugaaggaca gguuaagcu                                                    19

<210> SEQ ID NO 80
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 2, 9, 14,
<223> OTHER INFORMATION: /mod_base = 2'-O-methyl modification
      corresponding base

<400> SEQUENCE: 80
uugaaggaca gguuaagcu                                                    19

<210> SEQ ID NO 81
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = locked adenine
<220> FEATURE:
<221> NAME/KEY: misc_feature
<222> LOCATION: 2
<223> OTHER INFORMATION: n = locked guanosine
<220> FEATURE:
<221> NAME/KEY: modified_base
<222> LOCATION: 3
<223> OTHER INFORMATION: m5c = locked 5-methyl-cytidine
<220> FEATURE:
<221> NAME/KEY: misc_feature
<222> LOCATION: 4
<223> OTHER INFORMATION: n = locked 5-methyl-uridine

<400> SEQUENCE: 81
nncnuaaccu guccuucaa                                                    19

<210> SEQ ID NO 82
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 16
<223> OTHER INFORMATION: n = n = locked 5-methyl-uridine
<220> FEATURE:
<221> NAME/KEY: modified_base
<222> LOCATION: 17
<223> OTHER INFORMATION: m5c = locked 5-methyl-cytidine
<220> FEATURE:
<221> NAME/KEY: misc_feature
<222> LOCATION: 18, 19
<223> OTHER INFORMATION: n = locked adenine

<400> SEQUENCE: 82
agcuuaaccu guccuncnn                                                    19

<210> SEQ ID NO 83
<211> LENGTH: 19
<212> TYPE: RNA
<213> ORGANISM: Artificial Sequence
<220> FEATURE:

<223> OTHER INFORMATION: Synthetically generated oligonucleotide
<220> FEATURE:
<221> NAME/KEY: misc_feature
<222> LOCATION: 1, 18, 19
<223> OTHER INFORMATION: n = locked adenine
<220> FEATURE:
<221> NAME/KEY: misc_feature
<222> LOCATION: 2
<223> OTHER INFORMATION: n = locked guanosine
<220> FEATURE:
<221> NAME/KEY: modified_base
<222> LOCATION: 3, 17
<223> OTHER INFORMATION: m5c = locked 5-methyl-cytidine

<400> SEQUENCE: 83
nncnuaaccu guccuncnn                                                    19

<210> SEQ ID NO 84
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 18, 19
<223> OTHER INFORMATION: n = locked adenine
<220> FEATURE:
<221> NAME/KEY: misc_feature
<222> LOCATION: 2
<223> OTHER INFORMATION: n = locked guanosine

<400> SEQUENCE: 84
nncuuaaccu guccuucnn                                                    19

<210> SEQ ID NO 85
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2
<223> OTHER INFORMATION: n = locked 5-methyl-uridine
<220> FEATURE:
<221> NAME/KEY: misc_feature
<222> LOCATION: 3
<223> OTHER INFORMATION: n = locked guanosine
<220> FEATURE:
<221> NAME/KEY: misc_feature
<222> LOCATION: 4
<223> OTHER INFORMATION: n = locked adenine

<400> SEQUENCE: 85
nnnnaggaca gguuaagcu                                                    19

<210> SEQ ID NO 86
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 16
<223> OTHER INFORMATION: n = locked adenine
<220> FEATURE:
<221> NAME/KEY: misc_feature
<222> LOCATION: 17
<223> OTHER INFORMATION: n = locked guanosine
<220> FEATURE:
<221> NAME/KEY: modified_base
<222> LOCATION: 18

```
<223> OTHER INFORMATION: m5c = locked 5-methyl-cytidine
<220> FEATURE:
<221> NAME/KEY: misc_feature
<222> LOCATION: 19
<223> OTHER INFORMATION: n = locked 5-methyl-uridine

<400> SEQUENCE: 86
uugaaggaca gguuanncn                                                19

<210> SEQ ID NO 87
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 19
<223> OTHER INFORMATION: n = locked 5-methyl-uridine
<220> FEATURE:
<221> NAME/KEY: misc_feature
<222> LOCATION: 3, 17
<223> OTHER INFORMATION: n = locked guanosine
<220> FEATURE:
<221> NAME/KEY: misc_feature
<222> LOCATION: 4, 16
<223> OTHER INFORMATION: n = locked adenine
<220> FEATURE:
<221> NAME/KEY: modified_base
<222> LOCATION: 18
<223> OTHER INFORMATION: m5c = locked 5-methyl-cytidine

<400> SEQUENCE: 87
nnnnaggaca gguuanncn                                                19

<210> SEQ ID NO 88
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 19
<223> OTHER INFORMATION: n = locked 5-methyl-uridine
<220> FEATURE:
<221> NAME/KEY: modified_base
<222> LOCATION: 18
<223> OTHER INFORMATION: m5c = locked 5-methyl-cytidine

<400> SEQUENCE: 88
nngaaggaca gguuaagcn                                                19

<210> SEQ ID NO 89
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 89
tccatgacgt tcctgacgtt                                               20
```